US011332477B2

(12) United States Patent
Huang et al.

(10) Patent No.: US 11,332,477 B2
(45) Date of Patent: May 17, 2022

(54) NITROGEN CONTAINING HETEROCYCLE SUBSTITUTED BENZOXAZINE OXAZOLIDINONE COMPOUND AND PREPARATION METHOD AND USE THEREOF

(71) Applicant: INSTITUTE OF MATERIA MEDICA, CHINESE ACADEMY OF MEDICAL SCIENCES, Beijing (CN)

(72) Inventors: Haihong Huang, Beijing (CN); Dongfeng Zhang, Beijing (CN); Hongyi Zhao, Beijing (CN)

(73) Assignee: Institute of Materia Medica, Chinese Academy of Medical Sciences, Beijing (CN)

(*) Notice: Subject to any disclaimer, the term of this patent is extended or adjusted under 35 U.S.C. 154(b) by 106 days.

(21) Appl. No.: 16/498,876

(22) PCT Filed: Mar. 28, 2018

(86) PCT No.: PCT/CN2018/080777
§ 371 (c)(1),
(2) Date: Sep. 27, 2019

(87) PCT Pub. No.: WO2018/177302
PCT Pub. Date: Oct. 4, 2018

(65) Prior Publication Data
US 2021/0188871 A1    Jun. 24, 2021

(30) Foreign Application Priority Data

Mar. 28, 2017  (CN) .......................... 201710191791.4

(51) Int. Cl.
*C07D 498/04* (2006.01)
*A61P 31/06* (2006.01)
*C07D 519/00* (2006.01)

(52) U.S. Cl.
CPC ............ *C07D 498/04* (2013.01); *A61P 31/06* (2018.01); *C07D 519/00* (2013.01)

(58) Field of Classification Search
CPC ...... C07D 498/04; C07D 519/00; A61P 31/06
See application file for complete search history.

(56) References Cited

U.S. PATENT DOCUMENTS

| 8,293,734 B2 | 10/2012 | Thompson et al. |
| 8,507,481 B2 | 8/2013 | Yang et al. |
| 9,382,265 B2 | 7/2016 | Yang et al. |
| 10,550,092 B2* | 2/2020 | Cooper ................ C07D 263/24 |
| 2005/0070580 A1* | 3/2005 | Gordeev ................ C07D 413/10 514/340 |
| 2013/0123249 A1 | 5/2013 | Yang et al. |

FOREIGN PATENT DOCUMENTS

| CN | 102260277 A | 11/2011 |
| CN | 105218564 A | 1/2016 |
| CN | 105593232 A | 5/2016 |
| EP | 2578591 A1 | 4/2013 |
| RU | 2012107180 A | 9/2013 |
| WO | 96/35691 A1 | 11/1996 |
| WO | 2011-147259 A1 | 12/2011 |
| WO | WO-2017015106 A1 * | 1/2017 ........... C07D 413/06 |

OTHER PUBLICATIONS

Williams; Antimicrobial Agents and Chemotherapy, 2009, 53, 1314-1319. DOI: 10.1128/AAC.01182-08 (Year: 2009).*
Ai; Emerging Microbes & Infections 2016, 5, 1-8. (Year: 2016).*
Gadekar; European Journal of Medicinal Chemistry 2016, 122, 475-487. (Year: 2016).*
Xue; J. Med. Chern. 2014, 57, 7770-7791. (Year: 2014).*
Zhao; J. Med. Chern. 2020, 63, 17, 9316-9339. (Year: 2020).*
Zhao; ACS Med. Chem. Lett. 2017, 8, 5, 533-537. (Year: 2017).*
International Search Report and Written Opinion from International Application No. PCT/CN2018/080777, dated Jun. 1, 2018.
International Preliminary Report on Patentability from International Application No. PCT/CN2018/080777, dated Oct. 1, 2019.
Third Party Observation from International Application No. PCT/CN2018/080777, dated Jul. 29, 2019.
Qisheng Xin et al., "Design, Synthesis, and Structure—Activity Relationship Studies of Highly Potent Novel Benzoxazinyl-Oxazolidinone Antibacterial Agents," Journal of Medicinal Chemistry, 54, 7493-7502 (2011).
Tao Xue et al., "Synthesis and structure-activity relationship studies of novel [6,6,5] tricyclic oxazolidinone derivatives as potential antibacterial agents," Bioorganic & Medicinal Chemistry Letters, 25, 2203-2210 (2015).
Goncalves, Ivone et al., "Tuberculosis and Venous Thromboembolism: a case series", Cases Journal, 2009, 4 pages, vol. 2, No. 9333.

* cited by examiner

*Primary Examiner* — Daniel R Carcanague
(74) *Attorney, Agent, or Firm* — Merchant & Gould P.C.

(57) ABSTRACT

The present invention discloses a nitrogen-containing heterocyclic substituted benzoxazine oxazolidinone compound, a preparation method and use thereof in the manufacture of a medicament for treating and/or preventing infectious diseases caused by *Mycobacterium tuberculosis*. Specifically, the present invention relates to a compound represented by formula (I) and stereoisomer thereof, pharmaceutically acceptable salt thereof, and a pharmaceutical composition comprising the compounds of the present invention, use thereof, a method for preparing the compound, in which $X_1$, $X_2$, $R_1$ and $R_2$ are described in the specification.

17 Claims, No Drawings

NITROGEN CONTAINING HETEROCYCLE SUBSTITUTED BENZOXAZINE OXAZOLIDINONE COMPOUND AND PREPARATION METHOD AND USE THEREOF

This application is a National Stage Application of International Application No. PCT/CN2018/080777, filed 28 Mar. 2018, which claims benefit of Serial No. 201710191791.4, filed 28 Mar. 2017 in China and which applications are incorporated herein by reference. To the extent appropriate, a claim of priority is made to each of the above disclosed applications.

FIELD OF THE INVENTION

The invention belongs to the field of pharmacy, specifically relates to the nitrogen-containing heterocyclic substituted benzoxazine oxazolidinone compounds of formula (I), their preparation method, pharmaceutical composition comprising the compounds as active ingredients, and use in manufacture of a medicament for treating and/or preventing infectious diseases caused by *Mycobacterium tuberculosis*.

BACKGROUND OF THE INVENTION

Tuberculosis (TB) is a chronic fatal disease caused by *Mycobacterium tuberculosis*, as well as a serious infectious diseases threatening human's health and leading to death. Tuberculosis, like AIDS, is one of the leading causes of death worldwide. According to the report (Global tuberculosis report 2015) from the world health organization (WHO), it is estimated that worldwide 9.6 million people suffered from TB in 2014, including 5.4 million men, 3.2 million women and 1 million children. In 2014, TB killed 1.5 million people (1.1 million HIV-negative and 0.4 million HIV-positive) including 890,000 men, 480,000 women and 140,000 children.

Chemotherapy is the major method for treating tuberculosis. The use of streptomycin in 1944 created a new era of anti-TB medication. The development of isoniazid, rifampicin and pyrazinamide made the tuberculosis treatment duration reduce to six months, creating the era of "short course chemotherapy". However, it is difficult to adhere to the regular medication for patients as the occurrence of adverse effects resulting from long-term combined medicine. Furthermore, most of the drugs was developed in the fifties and sixties of the last century, long-term, extensive, and non-standard drug use aggravated the development of drug-resistant bacteria and prompted the emergence of multidrug-resistant tuberculosis (MDR-TB), extensively drug-resistant tuberculosis (XDR-TB), totally drug-resistant tuberculosis (TDR-TB), which need to use expensive and more toxic second-line or even third-line anti-TB drugs.

Compared with the existing anti-TB drugs, the oxazolidinones have novel structure and unique action mechanism. Linezolid, approved by the FDA in US in 2000, was used for treating Gram-positive bacterial infection with the longest treatment period of 28 days. Linezolid is clinically used for treating tuberculosis in an off-label manner, because its action mechanism is different from anti-TB drugs in clinic, and it does not produce cross-resistance with anti-TB drugs in clinic. Linezolid shows advantages in the treatment of refractory MDR-TB/XRD-TB. However, the long period for treating tuberculosis (more than or equal to 6 months) and serious side effects greatly limit the application of linezolid in treatment of tuberculosis (Linezolid in the treatment of drug-resistant tuberculosis: the challenge of its narrow therapeutic index. Expert Review of Anti-infective Therapy. 2016, 14 (10): 901-915). Blood toxicity (leukocytopenia, hemocytopenia, thrombocytopenia and anemia) is the symptom of the bone marrow toxicity among the side effects, which was considered to be related to mitochondrial protein synthesis (MPS) inhibition (Inhibition of Mammalian Mitochondrial Protein Synthesis by Oxazolidinones. Antimicrobial Agents and Chemotherapy, 2006, 50(6): 2042-2049). Sutezolid, currently in phase II clinical trials, showed better anti-TB activity in vitro than that of Linezolid, and showed higher safety in the clinical research (without hemocytopenia and peripheral neuropathy). However, some patients had ALT elevations in clinical research, so there was some concern about hepatic toxicity of sutezolid. Posizolid (AZD5847) developed by Astrazeneca company had entered phase II clinical trials, however it was interrupted due to the problem of safety and effectiveness.

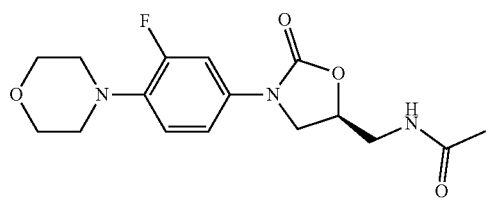

Linezolid

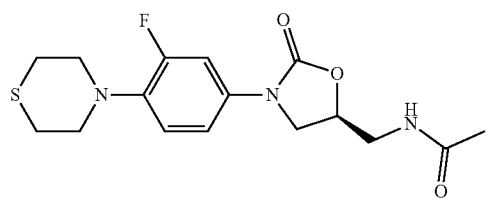

Sutezolid

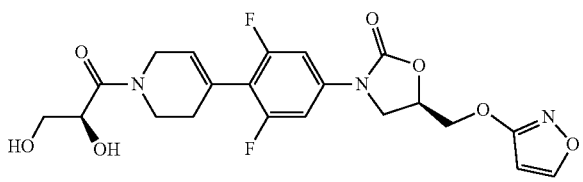

Posizolid

In view of the above situations, there is still a need for researching and developing new oxazolidinones with novel structure, much stronger anti-TB activity and fewer side effects.

The International patent application WO2011/147259 A1 disclosed the compounds represented by the following general formula (IV) on Dec. 1, 2011, which was used for treating infectious diseases, especially infectious diseases caused by multi-drug resistant bacteria selected from the group consisting of *Enterococcus, Staphylococcus aureus, Staphylococcus epidermidis*, and *pneumococcus*:

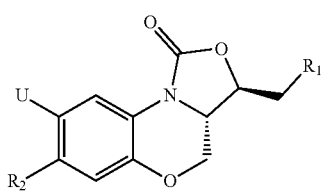

wherein, U is H or F, R₁ is

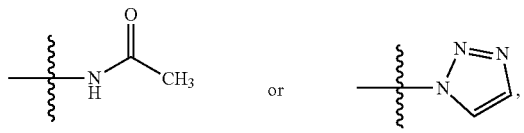

R₂ is a phenyl group, or a five membered or six membered aromatic or non-aromatic heterocyclic group.

The patent CN102260277 B which was granted on Jul. 24, 2013 disclosed the compounds represented by the formula (IV), wherein, R₂ is a phenyl group, or a five membered or six membered aromatic heterocyclic group.

In document WO2011/147259 A1, multi-drug resistant bacteria selected from the group consisting of *Enterococcus, Staphylococcus aureus, Staphylococcus epidermidis,* and *pneumococcus* belongs to the *Firmicutes*. However, *Mycobacterium tuberculosis* belongs to *Actinobacteria*. Taxonomically, they are different. There is no teaching that the compounds represented by formula (IV) from the document WO2011/147259 A1 have the activity of treating *Mycobacterium tuberculosis*.

Additionally, another document (J. Med. Chem. 2011, 54, 7493-7502) disclosed the following compound:

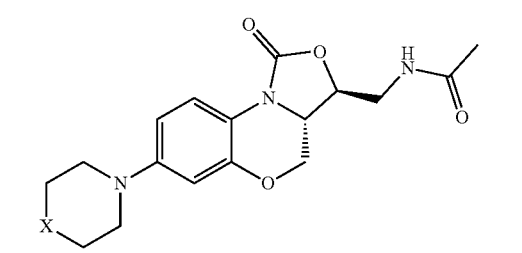

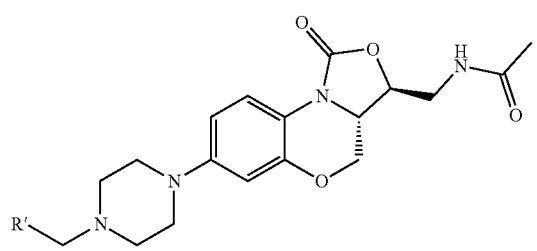

wherein, X is N or O, R' is 3-nitrophenyl, 2-nitrophenyl, 4-pyridinyl, 3-pyridinyl, 2-pyridinyl, 2-furanyl, 3-furanyl and 2-nitro-5-furanyl. The document disclosed their activity against *Staphylococcus aureus*, Methicillin-resistant *Staphylococcus aureus*, Methicillin-resistant *Staphylococcus epidermis*, penicillin-resistant *Streptococcus pneumoniae* and *enterococcus*. There is no teaching that the compound from the document has the activity of treating *Mycobacterium tuberculosis*.

SUMMARY OF THE INVENTION

An objective of the present invention is to provide nitrogen-containing heterocyclic substituted benzoxazine oxazolidinone compounds with new structure, low toxicity, potent activity against *Mycobacterium tuberculosis* and excellent pharmacokinetic properties. The inventors have found that the compounds have potent activity against *Mycobacterium tuberculosis* and low cytotoxicity, especially, the compounds in the present invention have a very low inhibitory effect on mitochondrial protein synthesis, which can greatly reduce the toxicity of bone marrow suppression. Thus, the invention provides a class of benzoxazine oxazolidinone compounds with new structure, strong anti-TB activity, high safety and excellent pharmacokinetic properties, which can be used for treating TB. The inventors completed the present invention on such basis.

The first aspect of the present invention is to provide a compound represented by formula (I), or isomers, or a pharmaceutically acceptable salt thereof,

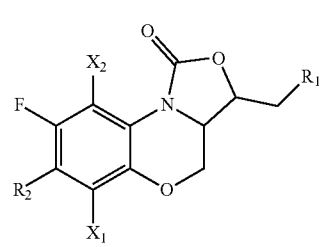

wherein,
$X_1$ and $X_2$ are each independently selected from H or F;
$R_1$ is —$OR_3$, —$NHR_3$, —$NHCOR_3$, —$NHCSR_3$, —$NHSO_2R_3$, —$NHCOOR_3$, —$NHCSOR_3$, —$NHCONHR_3$, —$NHCSNHR_3$, substituted or unsubstituted 5- to 6-membered heteroaryl;
$R_3$ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl, substituted or unsubstituted phenyl;
said substituted or unsubstituted 5- to 6-membered heteroaryl in $R_1$ or $R_3$ and substituted or unsubstituted 3- to 6-membered heterocyclic group in $R_3$ contain at least one heteroatom selected from N, O or S;
substituents on $R_1$ or $R_3$ are each independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino;
$R_2$ is substituted or unsubstituted

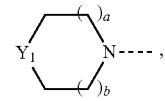

substituted or unsubstituted

substituted or unsubstituted

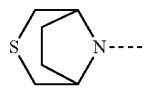

or substituted or unsubstituted

$Y_1$ is —S—, —S(=O)—, —S(O$_2$)—, —C(HF)—, —C(F$_2$)— or —C(=O)—;

$Y_2$ is —O—, —S—, —S(=O)—, —S(O$_2$)—, —C(HF)—, —C(F$_2$)— or —C(=O)—;

a and b are each 0, 1 or 2;

c and d are each 0, 1 or 2, and c and d are not 0 at the same time;

e and f are each 1 or 2;

substituents on $R_2$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

In a preferred embodiment, the present invention provides a compound represented by formula (II), or isomers, or a pharmaceutically acceptable salt thereof,

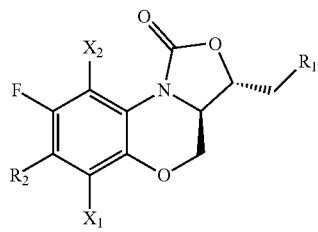

(II)

wherein, $X_1$, $X_2$, $R_1$ and $R_2$ are the same as those defined in the first aspect.

In another preferred embodiment, the present invention provides a compound represented by formula (III), or isomers, or a pharmaceutically acceptable salt thereof, (III)

wherein, $X_1$, $X_2$, $R_1$ and $R_2$ are the same as those defined in the first aspect.

In a further preferred embodiment, the present invention provides a compound represented by formula (II) or (III), or isomers, or a pharmaceutically acceptable salt thereof, wherein, $X_1$ and $X_2$ are each H;

$R_1$ is —NHR$_3$, —NHCOR$_3$, —NHSO$_2$R$_3$, —NHCOOR$_3$ or substituted or unsubstituted 5- to 6-membered heteroaryl;

$R_3$ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl;

said substituted or unsubstituted 5- to 6-membered heteroaryl in $R_1$ or $R_3$ and substituted or unsubstituted 3- to 6-membered heterocyclic group in $R_3$ contain at least one heteroatom from N, O or S;

substituents on $R_1$ or $R_3$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino;

$R_2$ is substituted or unsubstituted

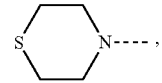

substituted or unsubstituted

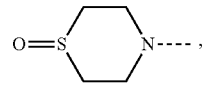

substituted or unsubstituted

substituted or unsubstituted

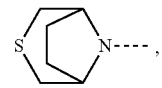

substituted or unsubstituted

substituted or unsubstituted

or substituted or unsubstituted

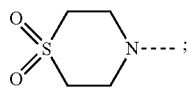

substituents on $R_2$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

In one aspect, compound represented by formula (II) is selected from formula (II-A),

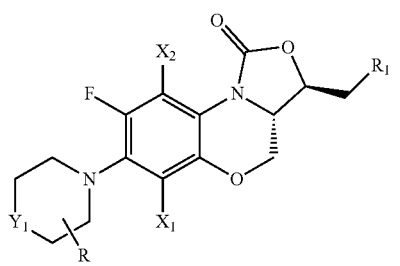

(II-A)

wherein, $X_1$ and $X_2$ are each H;

$Y_1$ is S, S=O, $CF_2$, $SO_2$;

$R_1$ is —$NHR_3$, —$NHCOR_3$, —$NHSO_2R_3$, —$NHCOOR_3$ or substituted or unsubstituted 5- to 6-membered heteroaryl;

$R_3$ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl;

said substituted or unsubstituted 5- to 6-membered heteroaryl in $R_1$ or $R_3$ and substituted or unsubstituted 3- to 6-membered heterocyclic group in $R_3$ contain at least one heteroatom selected from N, O or S;

substituents on $R_1$ or $R_3$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino;

R represents one or more substituents, which are the same or different, and which are each independently selected from the group consisting of H, F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

In another aspect, compound represented by formula (II) is selected from formula (II-B),

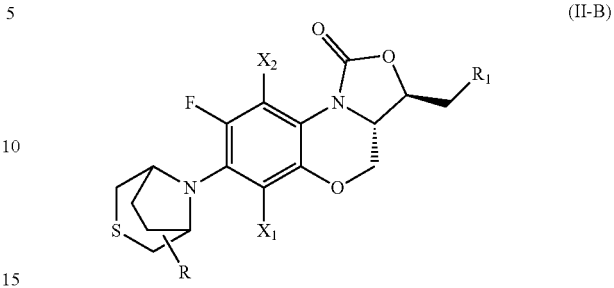

(II-B)

wherein, $X_1$ and $X_2$ are each H;

$R_1$ is —$NHR_3$, —$NHCOR_3$, —$NHSO_2R_3$, —$NHCOOR_3$ or substituted or unsubstituted 5- to 6-membered heteroaryl;

$R_3$ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl;

said substituted or unsubstituted 5- to 6-membered heteroaryl in $R_1$ or $R_3$ and substituted or unsubstituted 3- to 6-membered heterocyclic group in $R_3$ contain at least one heteroatom selected from N, O or S;

substituents on $R_1$ or $R_3$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino;

R represents one or more substituents, which are the same or different, and which are each independently selected from the group consisting of H, F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

In another aspect, compound represented by formula (II) is selected from formula (II-C),

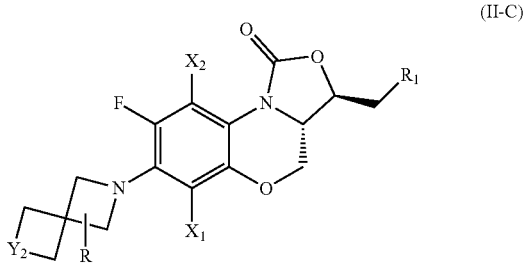

(II-C)

$X_1$ and $X_2$ are each H;

$Y_2$ is O or S;

$R_1$ is —$NHR_3$, —$NHCOR_3$, —$NHSO_2R_3$, —$NHCOOR_3$ or substituted or unsubstituted 5- to 6-membered heteroaryl;

$R_3$ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl;

said substituted or unsubstituted 5- to 6-membered heteroaryl in $R_1$ or $R_3$ and substituted or unsubstituted 3- to 6-membered heterocyclic group in $R_3$ contain at least one heteroatom selected from N, O or S;

substituents on $R_1$ or $R_3$ are independently selected from the group consisting of F, Cl, Br, hydroxyl, amino, nitro, cyano, trifluoromethyl, trifluoromethoxy, C₁-C₃ alkyl, halogenated C₁-C₃ alkyl, C₁-C₃ alkoxy and C₁-C₃ alkyl amino;

R represents one or more substituents, which are the same or different, and which are each independently selected from the group consisting of H, F, Cl, Br, hydroxyl, amino, nitro, cyano, trifluoromethyl, trifluoromethoxy, C₁-C₃ alkyl, halogenated C₁-C₃ alkyl, C₁-C₃ alkoxy and C₁-C₃ alkyl amino.

In one embodiment, compound represented by formula (III) is selected from formula (III-A),

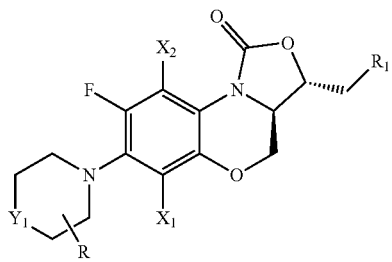

(III-A)

wherein,
X₁ and X₂ are each H;
Y₁ is S, S═O, CF₂, SO₂;
R₁ is —NHR₃, —NHCOR₃, —NHSO₂R₃, —NHCOOR₃, substituted or unsubstituted 5- to 6-membered heteroaryl;
R₃ is independently selected from the group consisting of hydrogen, substituted or unsubstituted C₁-C₄ alkyl, substituted or unsubstituted 3- to 6-membered cycloalkyl, substituted or unsubstituted 3- to 6-membered heterocyclic group, substituted or unsubstituted 5- to 6-membered heteroaryl;
said substituted or unsubstituted 5- to 6-membered heteroaryl in R₁ or R₃ and substituted or unsubstituted 3- to 6-membered heterocyclic group in R₃ contain at least one heteroatom selected from N, O or S;
substituents on R₁ or R₃ are independently selected from the group consisting of F, Cl, Br, hydroxyl, amino, nitro, cyano, trifluoromethyl, trifluoromethoxy, C₁-C₃ alkyl, halogenated C₁-C₃ alkyl, C₁-C₃ alkoxy and C₁-C₃ alkyl amino;
R represents one or more substituents, which are the same or different, and which are each independently selected from the group consisting of H, F, Cl, Br, hydroxyl, amino, nitro, cyano, trifluoromethyl, trifluoromethoxy, C₁-C₃ alkyl, halogenated C₁-C₃ alkyl, C₁-C₃ alkoxy and C₁-C₃ alkyl amino.

In another embodiment, compound represented by formula (III) is selected from formula (III-B),

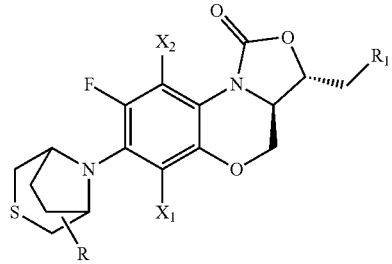

(III-B)

wherein,
X₁ and X₂ are each H;
R₁ is —NHR₃, —NHCOR₃, —NHSO₂R₃, —NHCOOR₃ or substituted or unsubstituted 5- to 6-membered heteroaryl;

R₃ is independently selected from the group consisting of hydrogen, substituted or unsubstituted C₁-C₄ alkyl, substituted or unsubstituted 3- to 6-membered cycloalkyl, substituted or unsubstituted 3- to 6-membered heterocyclic group, substituted or unsubstituted 5- to 6-membered heteroaryl;
said substituted or unsubstituted 5- to 6-membered heteroaryl in R₁ or R₃ and substituted or unsubstituted 3- to 6-membered heterocyclic group in R₃ contain at least one heteroatom selected from N, O or S;
substituents on R₁ or R₃ are independently selected from the group consisting of F, Cl, Br, hydroxyl, amino, nitro, cyano, trifluoromethyl, trifluoromethoxy, C₁-C₃ alkyl, halogenated C₁-C₃ alkyl, C₁-C₃ alkoxy and C₁-C₃ alkyl amino;
R represents one or more substituents, which are the same or different, and which are each independently selected from the group consisting of H, F, Cl, Br, hydroxyl, amino, nitro, cyano, trifluoromethyl, trifluoromethoxy, C₁-C₃ alkyl, halogenated C₁-C₃ alkyl, C₁-C₃ alkoxy and C₁-C₃ alkyl amino.

In another embodiment, compound represented by formula (III) is selected from formula (III-C),

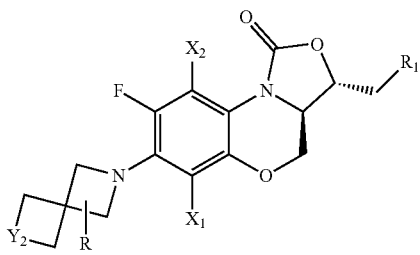

(III-C)

wherein,
X₁ and X₂ are each H;
Y₂ is O or S;
R₁ is —NHR₃, —NHCOR₃, —NHSO₂R₃, —NHCOOR₃, substituted or unsubstituted 5- to 6-membered heteroaryl;
R₃ is independently selected from the group consisting of hydrogen, substituted or unsubstituted C₁-C₄ alkyl, substituted or unsubstituted 3- to 6-membered cycloalkyl, substituted or unsubstituted 3- to 6-membered heterocyclic group, substituted or unsubstituted 5- to 6-membered heteroaryl;
said substituted or unsubstituted 5- to 6-membered heteroaryl in R₁ or R₃ and substituted or unsubstituted 3- to 6-membered heterocyclic group in R₃ contain at least one heteroatom selected from N, O or S;
substituents on R₁ or R₃ are independently selected from the group consisting of F, Cl, Br, hydroxyl, amino, nitro, cyano, trifluoromethyl, trifluoromethoxy, C₁-C₃ alkyl, halogenated C₁-C₃ alkyl, C₁-C₃ alkoxy and C₁-C₃ alkyl amino;
R represents one or more substituents, which are the same or different, and which are each independently selected from the group consisting of H, F, Cl, Br, hydroxyl, amino, nitro, cyano, trifluoromethyl, trifluoromethoxy, C₁-C₃ alkyl, halogenated C₁-C₃ alkyl, C₁-C₃ alkoxy and C₁-C₃ alkyl amino.

Preferably,
X₁ is H;
X₂ is H;
R₁ is amino, methylamino,

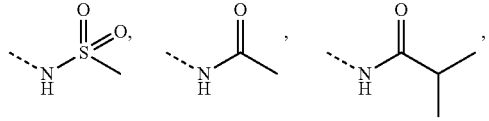

-continued

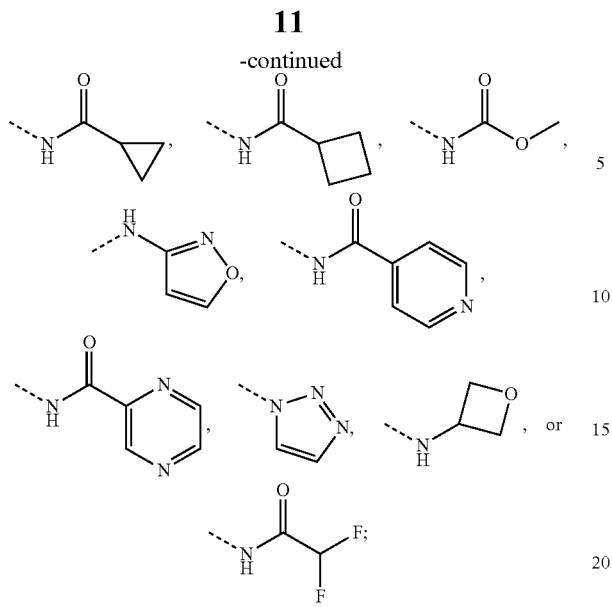

R₂ is

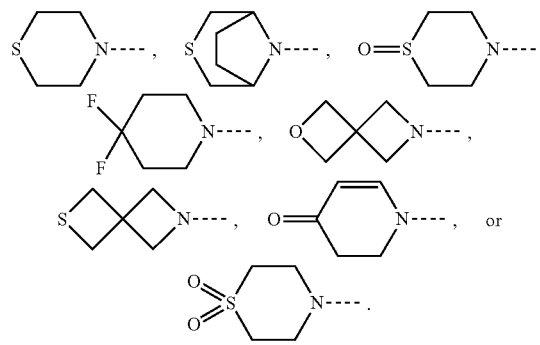

The pharmaceutically acceptable salt of the compounds of the invention is a salt formed with the following acids respectively: hydrochloric acid, p-toluenesulfonic acid, tartaric acid, maleic acid, lactic acid, methanesulfonic acid, sulfuric acid, phosphoric acid, citric acid, acetic acid or trifluoroacetic acid; preferably hydrochloric acid, p-toluenesulfonic acid or trifluoroacetic acid.

According to any one of the first aspect, the compound of this invention refers to the target compounds (represented by a formula or named after system description) in the examples, or stereoisomer thereof or the pharmaceutically acceptable salt thereof.

The compounds preferred according to any one of the first aspect are as follows:

Compound 1

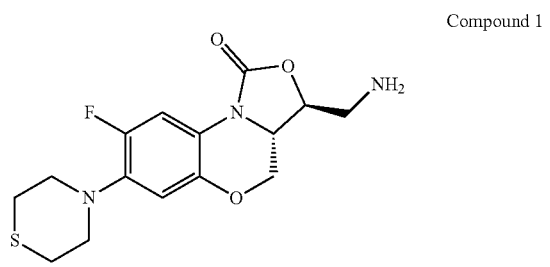

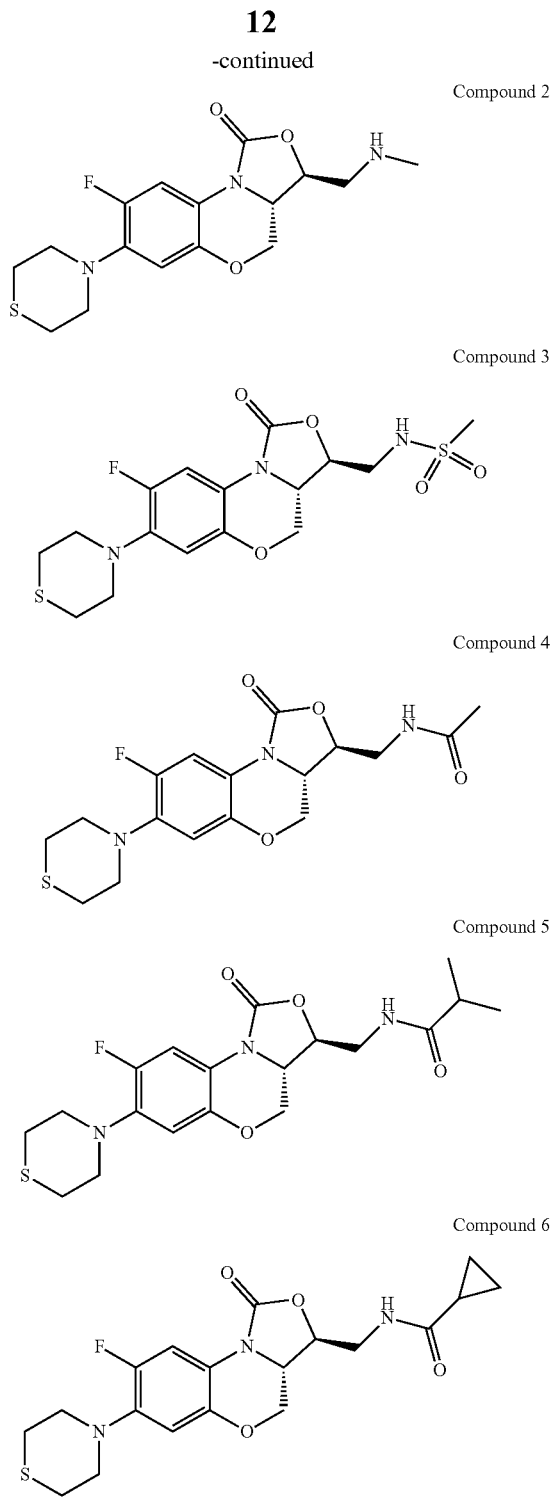

Compound 2

Compound 3

Compound 4

Compound 5

Compound 6

Compound 7

Compound 8
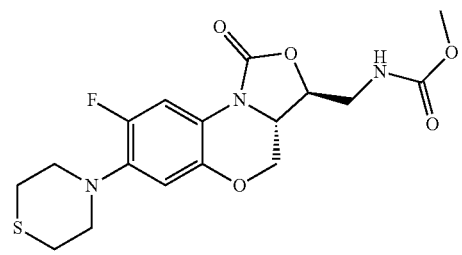
Compound 9
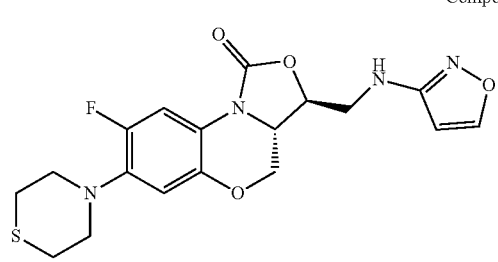
Compound 10
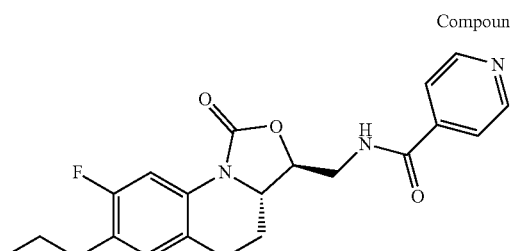
Compound 11
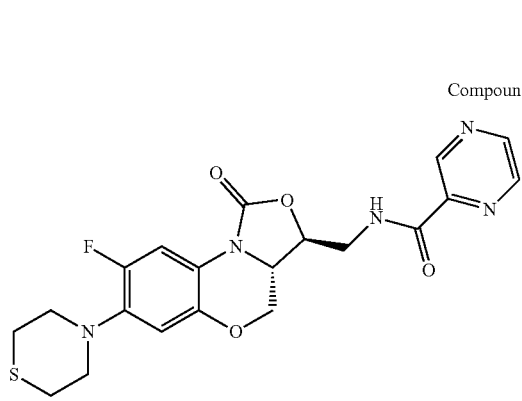
Compound 12
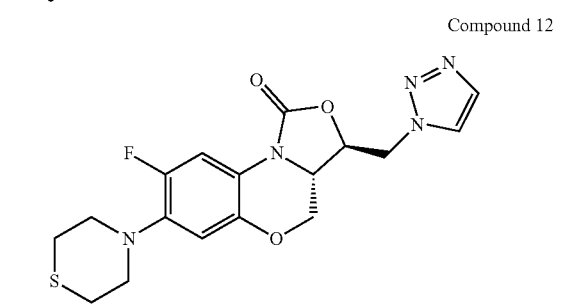
Compound 13
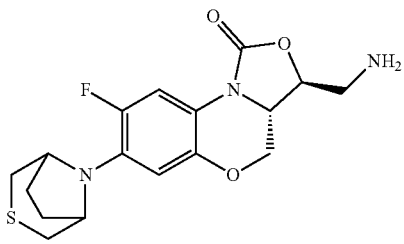
Compound 14
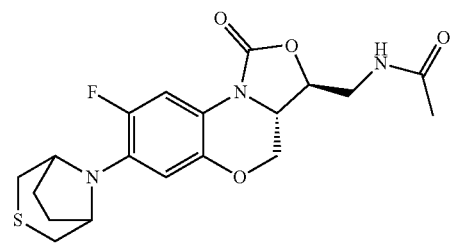
Compound 15
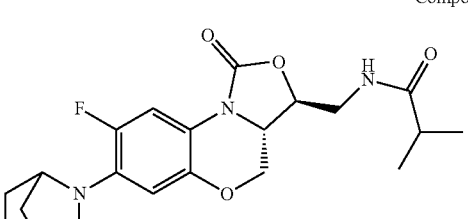
Compound 16
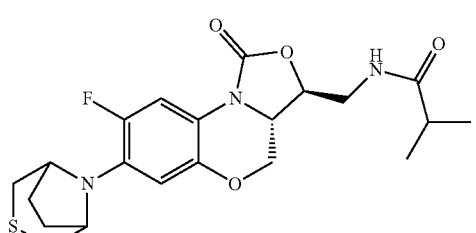
Compound 17
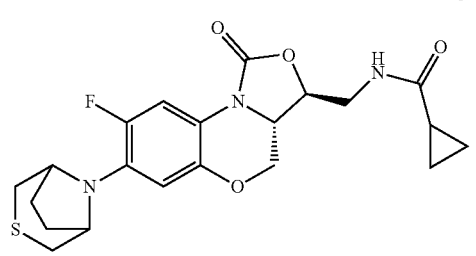
Compound 18
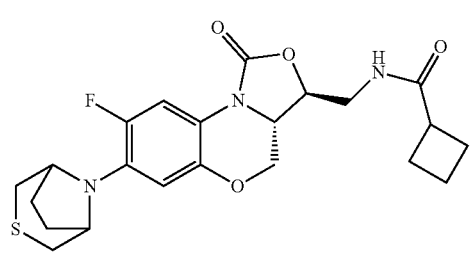

Compound 19
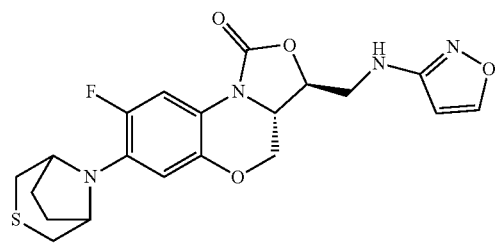
Compound 20
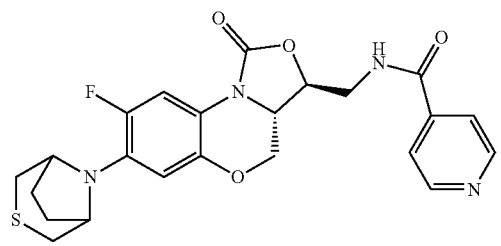
Compound 21
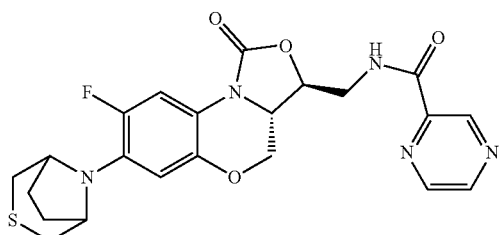
Compound 22
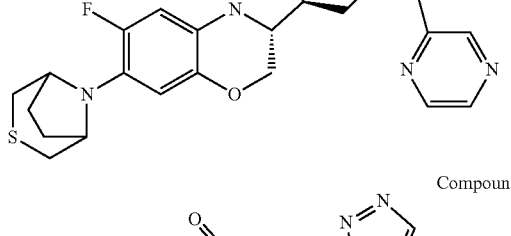
Compound 23
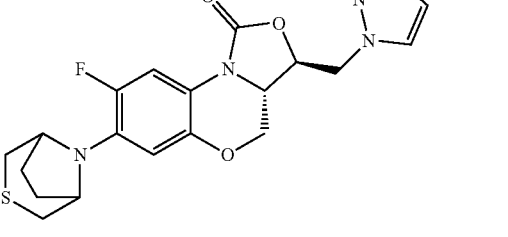
Compound 24
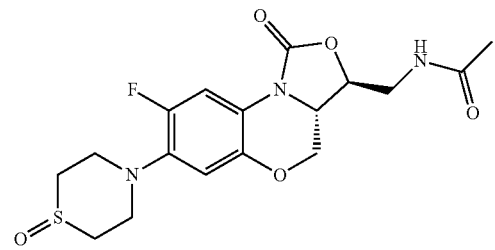
Compound 25
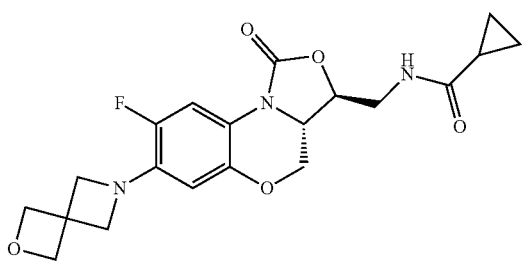
Compound 26
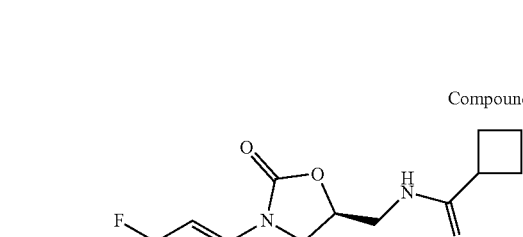
Compound 27
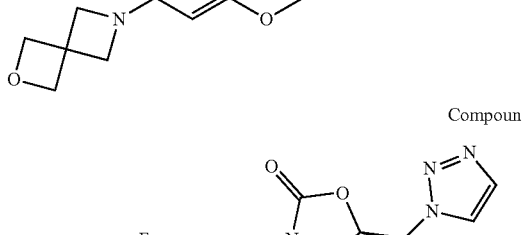
Compound 28
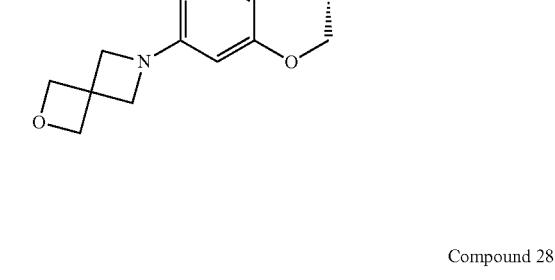
Compound 29
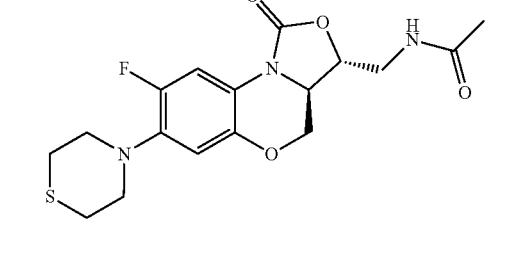

Compound 30
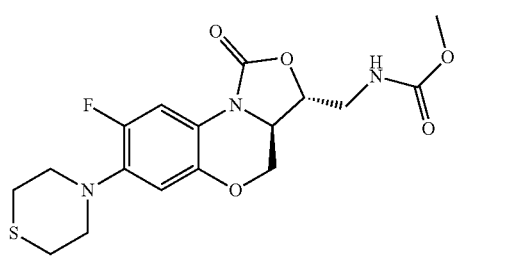
Compound 31
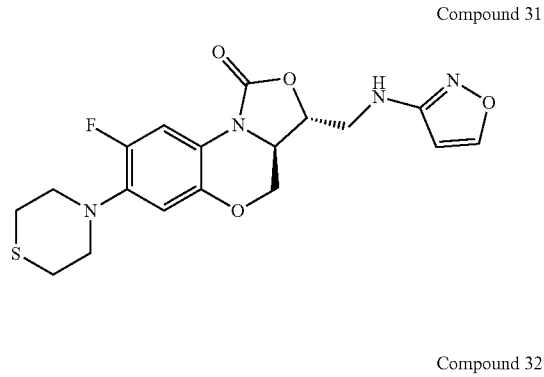
Compound 32
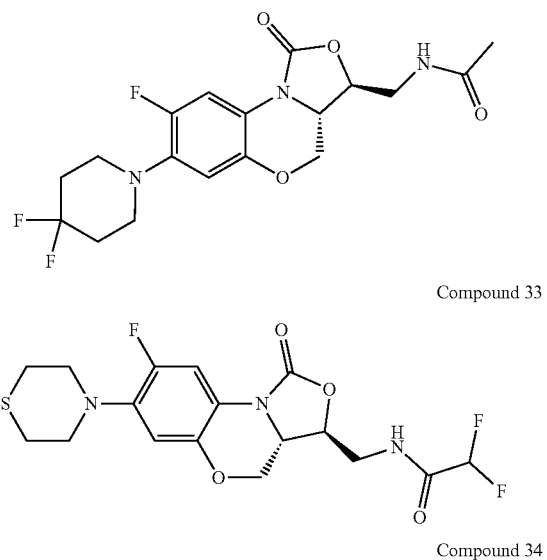
Compound 33
Compound 34
Compound 35
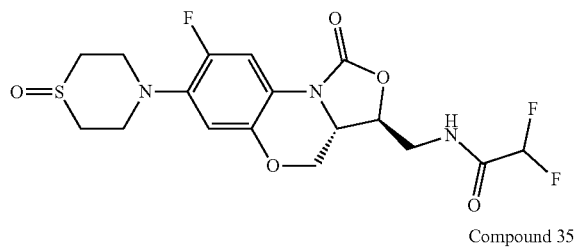
Compound 36
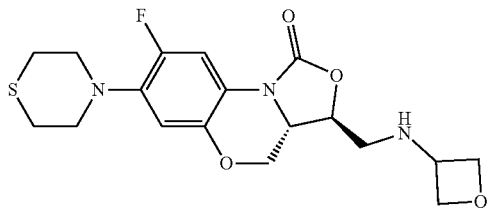
The second aspect of the present invention provides a method for preparing the compounds described in any one of the first aspect, which includes the following steps:
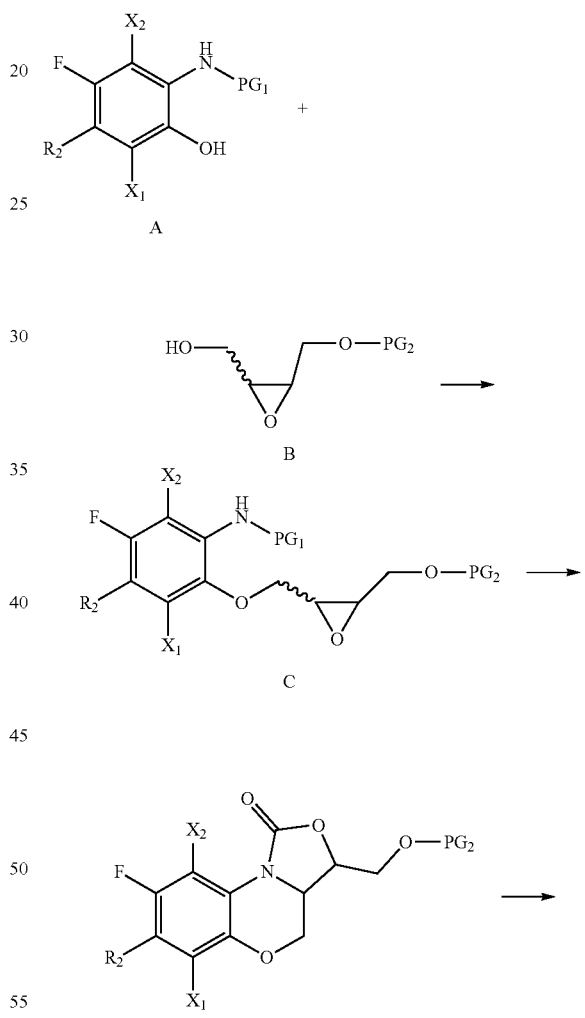
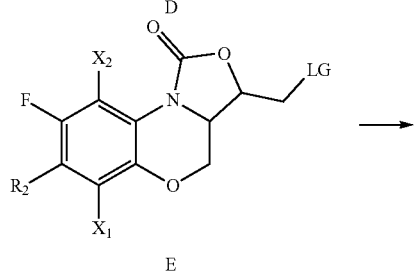

-continued

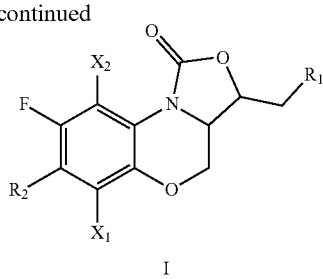

I

Compound A reacts with compound B via a Mitsunobu reaction (referring to the book "Modern Organic Reactions", chemical industry press, Yuefei Hu, Guoqiang Lin ed., in 2008 the first edition, volume 3, 187-244) to obtain compound C. Cyclization of compound C in the presence of lithium-containing base provides compound D. The protection group $PG_2$ of the hydroxyl in compound D is removed to obtain hydroxyl product (referring to the book "Protection Group in Organic Synthesis", East China University of Science and Technology press, translated by East China University of Science and Technology of organic chemistry, in October 2004, the first edition), and then the hydroxyl product is converted to compound E containing a leaving group LG (e.g., halogen, pseudohalogen). Compounds represented by formula (I) can be synthesized from compound E according to the known synthetic method in the field of the oxazolidinones.

Specifically,
1) Compound A is prepared according to the following scheme:

Compound e is obtained from compound d under reduction conditions (e.g. Raney nickel-$H_2$, Pd/C—$H_2$, zinc powder-acetic acid, zinc powder-ammonium formate or iron powder-hydrochloric acid).

Compound e reacts with the chloroformates (such as methyl chloroformate, ethyl chloroformate, tert-butyl chloroformate or benzyl chloroformate) or anhydride (e.g. $(Boc)_2$ O) in the presence of base (such as sodium carbonate, sodium bicarbonate, potassium carbonate, triethylamine or diisopropylethylamine) in the solvent (such as tetrahydrofuran, water or mixed solvent of both) at a temperature from 0° C. to 30° C., to obtain compound A containing amino protecting group $PG_1$.

Compound d can be obtained by mixing compound f and nitrogen-containing $R_2H$ under alkaline condition (e.g. organic base: triethylamine, diisopropylethylamine, DBU, N-methylmorpholine or inorganic base: sodium bicarbonate, cesium carbonate, potassium carbonate), at a temperature from –10° C. to 20° C., in a suitable solvent (e.g. tetrahydrofuran, acetonitrile, DMF, NMP or water);

2) Protecting group $PG_2$ in compound B includes silyl ethers (e.g. tert-butyl dimethyl silyl ether or tert-butyl diphenyl silyl ether), benzyl ethers (p-bromobenzyl ether, p-methoxybenzyl ether or trityl ether), benzoates (e.g. benzoates or p-nitrobenzoates), and racemic compound B can be prepared by oxidation of 3-chloroperoxybenzoic acid. Optically active compound B can be obtained via the Sharpless epoxidation reaction.

3) Compound C can be obtained by mixing compound A and compound B in solvents (e.g. dichloromethane, toluene, tetrahydrofuran or tert-butyl methyl ether) in the presence of phosphine reagents (e.g. triphenylphosphine or tributylphos-

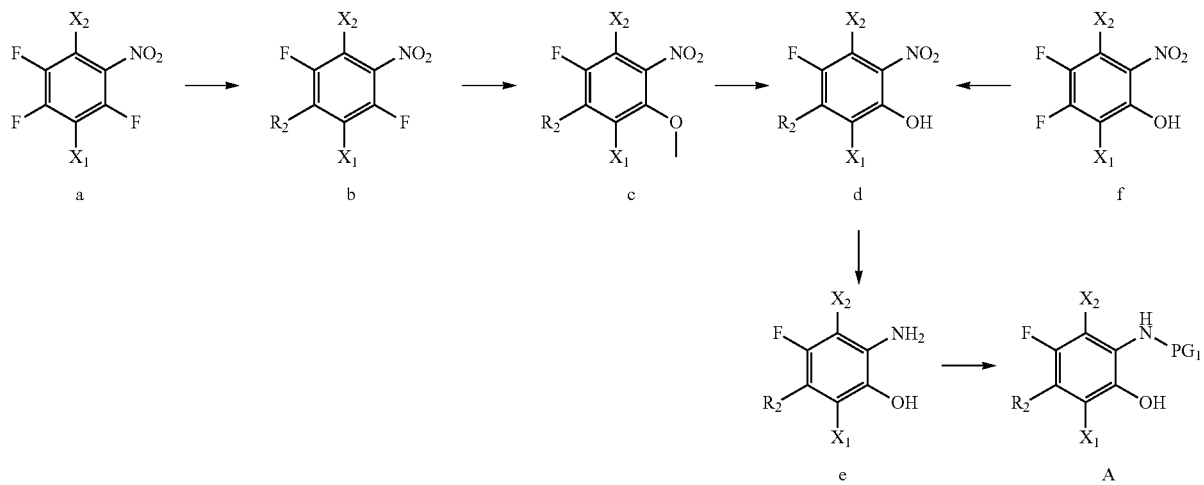

Compound a reacts with nitrogen-containing $R_2H$ under alkaline condition (e.g. organic base: triethylamine, diisopropylethylamine, DBU, or inorganic base: sodium bicarbonate, cesium carbonate, potassium carbonate), in a suitable solvent (e.g. tetrahydrofuran, acetonitrile, DMF, NMP, water), at a temperature from –10° C. to 20° C., to obtain compound b.

Compound b reacts with sodium methylate in methanol to obtain compound c.

Compound c reacts with demethylating reagents (e.g. HBr, HI, $BBr_3$ or LiCl) in a suitable solvent (e.g. dichloromethane or DMF) to obtain compound d.

phine) and azodicarbonate compounds (e.g. diethyl azodicarbonate or diisopropyl azodicarbonate) or azodicarbonamides (e.g. 1,1'-(azodicarbonyl)-dipiperidine) via Mitsunobu reaction.

4) Compound D can be obtained by cyclization of compound C in solvents (e.g. tetrahydrofuran or tert-butyl methyl ether) in the presence of lithium metal bases (e.g. tert-butoxylithium, butyllithium, LiHMIDS, LDA).

5) Removing the protecting group from compound D by appropriate methods (e.g. silyl ether protecting group can be removed by tetrabutylammonium fluoride or acid, benzyl ether protecting group can be removed by hydrogenation or acid, and benzoate protecting group can be removed by inorganic base) can give alcohol intermediate, and then converting alcohol into the leaving group LG (e.g. chlorine, bromine, iodine or pseudohalogen) can produce a compound represented by formula E.

6) According to the prior art, compound E can be converted to a compound represented by formula (I) with different $R_1$ group;

replacing compound B with

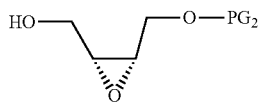

in the above synthetic steps can obtain the corresponding compound represented by formula (II);

replacing compound B with

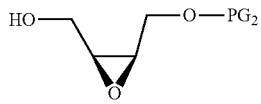

in the above synthetic steps can obtain the corresponding compound represented by formula (III);

wherein, the definition of $X_1$, $X_2$, $R_1$ and $R_2$ are as described in the first aspect of the invention.

The third aspect of the present invention provides a pharmaceutical composition comprising a therapeutically effective amount of the compound of any one of the first aspect, isomers thereof or a pharmaceutically acceptable salt thereof, and one or more pharmaceutically acceptable adjuvant.

The fourth aspect of the present invention provides the use of the compound of any one of the first aspect, isomers thereof or a pharmaceutically acceptable salt thereof according to the first aspect or the pharmaceutical composition according to any one of the third aspect in the manufacture of a medicament for treating and/or preventing microbial infectious diseases caused by *Mycobacterium tuberculosis*.

The feature of any aspect or any one of the aspects of the present invention can also be applied to any other aspect or any one of the other aspect, provided that they do not contradict each other and, of course, when applicable to each other, the corresponding features can be modified appropriately if necessary. In the present invention, for example, when referring to "any one of the first aspect of the present invention", the term "any one" refers to any one sub-aspect of the first aspect of the present invention and has similar meaning when referred to in a similar way in other aspects.

DETAIL DESCRIPTION OF THE INVENTION

The various aspects and features of the present invention are further described below.

All references cited by the present invention are incorporated herein by reference in their entirely. If the meanings expressed by these references are inconsistent with those of the present invention, the expression of the present invention shall prevail. In addition, the various terms and phrases used by the present invention have general meanings understood by one skilled in the art. Even so, the present invention still wants to describe and explain these terms and phrases in more detail herein. If the terms and phrases mentioned are inconsistent with the known meanings, the meanings expressed by the present invention shall prevail. The following are definitions of various terms used in the present invention, which are applicable to the terms used throughout the specification of this application, unless otherwise specified in specific situation.

Compounds of the invention have asymmetric centers. Compounds containing asymmetric substituted atoms in the invention can be separated into optical active or racemic forms. One skilled in the art knows how to prepare optical active forms, such as resolution of racemic forms or synthesis from the optical active starting material. Unless otherwise specified, the present invention includes all chiral isomers, diastereomers and racemic isomers. The method for preparing the compounds of the invention and their intermediates belongs to a part of the invention. All tautomers of the compounds of the invention also belong to one part of the invention.

The term "stereoisomers" refers to compounds which have identical chemical constitution, but differ with regard to the arrangement of atoms or groups in space. Stereoisomers include enantiomers, diastereomers, conformational isomers (rotamer), geometric isomers, atropisomer, etc.

"Chiral molecules" refer to molecules which have the property of non-superimposability of the mirror image partner, while the term "achiral molecules" refer to molecules which are of superimposability on their mirror image partner.

"Enantiomers" refer to two stereoisomers of a compound which are non-superimposable mirror images of one another.

"Diastereomer" refers to a stereoisomer with two or more centers of chirality and whose molecules are not mirror images of one another. Diastereomers have different physical properties, e.g. melting point, boiling point, spectral properties and reactivity. Mixture of diastereomers may be separated under high resolution analytical procedures such as electrophoresis and chromatography such as HPLC.

Many organic compounds exist in optical active forms, i.e., they have the ability to rotate the plane of plane-polarized light. In describing an optically active compound, the prefixes D and L, or R and S, are used to denote the absolute configuration of the molecule about its chiral center(s). The prefixes D and L, or (+) and (−) are employed to designate the sign of rotation of plane-polarized light by the compound, with (−) or L meaning that the compound is levorotatory. A compound prefixed with (+) or D is dextrorotatory. A specific stereoisomer may refer to as an enantiomer, and a mixture of such stereoisomers is called an enantiomeric mixture. A 50:50 mixture of enantiomers is referred to as a racemic mixture or a racemate, which may occur when there is no stereoselection or stereospecificity in a chemical reaction or process.

Any asymmetric atom (e.g. carbon or the like) of the compound(s) disclosed herein can be present in a racemic form or an enantiomerically enriched form, for example the (R)-, (S)-, (R,S)-, (S,R)-, (R,R)- or (S,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active isomers may be prepared using chiral synthons or chiral reagents, or resolved using conventional techniques.

The resulting mixture of any stereoisomers can be separated into pure or substantially pure geometric isomers, enantiomers, diastereomers, for example by chromatography and/or fractional crystallization, depending on the difference in physicochemical properties of the components.

The term "substituted" refers to the substitution of one or more hydrogen atoms in a given structure by a specific substituent group, provided that the valence state of a particular atom is normal and the resulting compound is stable after substitution. Unless otherwise indicated, each substitutable position of the group can be substituted by an optional substituent. When more than one position in a given structure can be substituted by one or more substituents selected from a specific group, each position can be substituted same or differently by the substituent. Substituents described herein include, but are not limited to, hydrogen, deuterium, oxo (=O), halogen, cyano, nitro, hydroxyl, mercapto, amino (—NH$_2$), aromatic amino, aminoalkyl, alkyl, alkylthio, hydroxylalkyl, haloalkyl, cycloalkyl, heterocyclyl, aryl, heteroaryl, —C(=O)R$^a$, —OR$^b$, —COOR$^b$, —SO$_2$R$^b$, —NR$^c$R$^d$, —CONR$^c$R$^d$, —SO$_2$NR$^c$R$^d$, —C(NR$^c$R$^d$), wherein R$^a$, R$^b$, R$^c$ and R$^d$ are each independently hydrogen, cyano, amino, alkylamino, aromatic amino, alkylthio, alkoxy, aryloxy, hydroxyl, mercapto, alkyl, haloalkyl, cycloalkyl, heterocyclyl, aryl, heteroaryl, alkylsulfonyl, aminosulfonyl, hydroxylalkyl, aminoalkylcarbonyl or alkylcarbonyl.

The content of carbon atoms in various hydrocarbon-containing moieties is expressed by the prefix indicating the minimum and maximum number of carbon atoms in the corresponding moiety. $C_i$-$C_j$ denotes the moiety with an integer "i" (containing i) to an integer "j" (containing j) of carbon atoms. Therefore, for example, $C_1$-$C_4$ alkyl refers to alkyl with 1 to 4 (containing 1 and 4) carbon atoms, especially methyl, ethyl, $C_3$ alkyl and $C_4$ alkyl.

As described herein, the term "alkyl" refers to an alkyl with a specified number of carbon atoms, which is a straight-chain or branched-chain alkyl, and may include its subgroups. For example, the term "$C_1$-$C_4$ alkyl" refers a subrange of group represented by $C_1$-$C_3$ alkyl, $C_1$-$C_2$ alkyl, $C_2$-$C_4$ alkyl, $C_3$-$C_4$ alkyl, etc., and specific groups such as methyl, ethyl, n-propyl, isopropyl. The terms "alkoxy" and "alkylamino" belong to common expressions, referring to alkyl groups attached to the rest of the molecule via an oxygen atom or an amino group, wherein alkyl groups are as described herein. Alkoxy includes, but is not limited to, methoxy, ethoxy, isopropoxy, n-propoxy, etc. Alkylamino includes, but is not limited to, methylamino, ethylamino, isopropylamino, n-propylamino, and the like.

The term "haloalkyl" means that the alkyl is substituted with one or more halogen atoms, including, but not limited to, trifluoromethyl, difluoromethyl, and the like.

As described herein, the terms "halo", "halogen", "halogen atom" and "halogenated" denote fluorine (F), chlorine (Cl), bromine (Br) or iodine (I).

As described herein, the term "pseudohalogen" refers to sulfonyloxy, especially trifluoromethyl sulfonyloxy, p-methylphenyl sulfonyloxy, methyl sulfonyloxy and p-nitrophenyl sulfonyloxy.

As described herein, the term "cycloalkyl" refers to a cyclic alkyl with a specified number of carbon atoms, and it also includes its subgroups, for example, the term "3-6-membered cycloalkyl" refers a subrange of group represented by 3-5-membered cycloalkyl, 4-6-membered cycloalkyl, and the like, and specific groups such as cyclopropyl and cyclobutyl, cyclopentyl and cyclohexyl.

As described herein, the term "heterocyclyl" refers to a cyclic heteroalkyl group with a specified number of ring atoms, including a single or fused ring group. In a ring, there are 4 to 10 ring atoms, one or two of which are selected from a heteroatom of nitrogen, oxygen or sulfur, and the remaining ring atoms are carbon. These rings can also have one or more double bonds, but they do not have a fully conjugated π-electron system. Heterocyclic group includes, but is not limited to, oxetanyl, azatidinyl, pyrrolidinyl, pyrazolidinyl, dihydrothienyl, 1,3-dioxolanyl, dithiolanyl, tetrahydropyranyl, tetrahydrothiopyranyl, piperidinyl, 1,2-dihydropyridyl, morpholinyl, thiomorpholinyl, hexahydropyrimidyl, piperazinyl, homopiperazinyl, 1,3-benzoxazinyl, oxazolidinyl, homoperidinyl, and the like.

As described herein, the term "heteroaryl" refers to aromatic groups with 1 to 3 heteroatoms selected from oxygen, sulfur and nitrogen as ring atoms and the remaining ring atoms are carbon. Example of "5- to 6-membered heteroaryl" includes 5-membered heteroaryl and 6-membered heteroaryl. 5-membered heteroaryl includes but is not limited to imidazolyl, furanyl, thienyl, triazolyl, tetrazolyl, pyrazolyl (e.g. 2-pyrazolyl), thiazolyl, oxazolyl and isoxazolyl. The 6-membered heteroaryl includes pyridyl, pyridazinyl, pyrimidinyl, pyrazinyl or 1,3,5-triazinyl. In the embodiments, the heteroaryl is triazolyl, pyrazinyl, isoxazolyl or pyridinyl.

As described herein, the term "ring" denotes the substituted or non-substituted cycloalkyl, substituted or non-substituted heterocyclyl, substituted or non-substituted aryl, or substituted or non-substituted heteroaryl. Said ring includes fused ring. The number of atoms in a ring is usually defined as the number in a ring. For example, "3- to 6-membered ring" refers to the circle arrangement of 3 to 6 atoms in a ring.

As described herein, the ring system formed by the substituent R$^e$ with one bond connected to the central ring represents that one or more identical or different substituents R$^e$ can be substituted at any substitutable position on the ring. For example, formula (a) represents that any substitutable position on A ring or B ring can be substituted by one or more R$^e$.

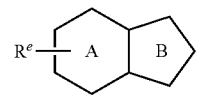

(a)

"Leaving group" or "LG" has the common meanings associated with synthetic organic chemistry, i.e., atoms or groups that can be replaced by nucleophilic groups, including halogens, aliphatic or aromatic sulfonyloxyl, such as chlorine atom, bromine atom, iodine atom, methylsulfonyloxy group, tolylsulfonyloxy group, trifluoromethyl sulfonyloxy group, and the like.

"Protective group" or "PG" refers to a substituent that is commonly employed to block or protect a particular functionality of a functional group while reacting with other functional groups on the compound. For example, an "amino-protective group" refers to a substituent attached to an amino group to block or protect the amino functionality in the compound. Suitable amino-protective groups include tert-butoxycarbonyl (Boc), benzyloxycarbonyl (Cbz), methoxycarbonyl and ethoxycarbonyl. Similarly, a "hydroxyl-protective group" refers to a substituent of a hydroxyl group that blocks or protects the hydroxyl functionality.

As described herein, the term "effective amount" refers to the amount of drug that can be used in a subject to achieve the desired treatment of the disease or symptoms described herein.

As described herein, the term "pharmaceutically acceptable", for example, when describing "pharmaceutically acceptable salt", indicates that the salt not only is physiologically acceptable to the subject, but also refers to synthetic substance of pharmaceutical value, such as a salt formed as intermediates in chiral resolution, although in this case, the intermediate salt cannot be directly given to the subjects, it can play a role in obtaining the final product of the invention.

As described herein, the term "pharmaceutical composition" may also refer to "composition", which can be used to treat diseases or symptoms described herein in subjects, especially in mammals.

"Treatment" of diseases includes:

(1) preventing the disease, i.e. preventing the clinical symptoms of the disease from occurring in mammals exposed to or susceptible to the disease but without experience or manifestation of its symptoms, (2) inhibiting the disease, i.e. preventing or reducing the progression of the disease or its clinical symptoms.

(3) alleviating the disease, that is, causing the recovery of the disease or its clinical symptoms.

"Therapeutically effective amount" refers to the amount of a compound sufficient to treat a disease when applied to mammals. Therapeutically effective amount varies according to the compound, the disease to be treated and its severity, as well as the age, weight and sex of mammals. Therapeutically effective amount also refers to any amount of a compound sufficient to achieve the desired beneficial effect, which includes preventing disease, inhibiting disease or alleviating disease as described in (1) to (3) above. For example, the amount of the compound may be 0.1-250 mg/kg, or preferably, 0.5-100 mg/kg, or more preferably, 1-50 mg/kg, or even more preferably, 2-20 mg/kg. Preferably, the amount of the compound is applied to mammals twice a day. More preferably, the amount of compound is applied to mammals once a day. More preferably, the amount of the compound is applied to mammals once a week or twice a week.

As described herein, the term "disease and/or symptoms" refers to a physical state of the subject, which is related to the disease and/or symptoms described in the present invention. For example, the diseases and/or symptoms described in the present invention refer to infectious diseases caused by tuberculosis *bacillus.*

As described herein, the term "subject" may refer to a patient or other animals, in particular a mammal, such as a human, dog, monkey, cattle, horse, etc., that receives the compound represented by formula (I) or its pharmaceutical composition to treat the disease or symptoms described herein.

On the one hand, the invention also relates to a pharmaceutical composition in which compounds herein are used as active ingredients. The pharmaceutical composition can be prepared in accordance with a method known in the art. Any formulation suitable for human or animal can be prepared by combining the compound of the invention with one or more pharmaceutically acceptable solid or liquid excipients and/or adjuvants.

The compounds in the invention or pharmaceutical compositions containing them can be administered in a unit dose form through intestinal or parenteral way, such as orally, intravenously, intramuscularly, subcutaneously, nasally, or via oral mucosa, eyes, lungs and respiratory tracts, skin, vagina, rectum, and the like.

The dosage forms can be liquid dosage forms, solid dosage forms or semi-solid dosage forms. The liquid dosage forms can be solution (including true solution and colloidal solution), emulsion (including o/w, w/o and multiple emulsion), suspension, injection (including water injection, powder for injection and infusion), eye drops, nasal drops, lotion and liniment, etc. The solid formulation can be tablet (including normal tablets, enteric-coated tablets, buccal tablets, dispersible tablets, chewable tablets, effervescent tablets, orally disintegrating tablets), capsules (including hard capsules, soft capsules, enteric capsules), granules, powders, pellets, pills drops, suppositories, membrane, transdermal patch, aerosol, sprays, etc. Semi-solid formulations can be ointment, gelatin, paste, etc.

The compound of the invention can be made into normal preparation, sustained-release preparation, controlled-release preparation, targeted preparation and various particle delivery systems.

In order to prepare the compound of the invention into tablets, various excipients known in the art can be widely used, including diluents, adhesives, wetting agents, disintegrants, lubricants and cosolvents. Dilutants can be starch, dextrin, sucrose, glucose, lactose, mannitol, sorbitol, xylitol, microcrystalline cellulose, calcium sulfate, calcium hydrogen phosphate, calcium carbonate, etc. Wetting agents can be water, ethanol, isopropanol, etc. Adhesives can be starch syrup, dextrin, syrup, honey, glucose solution, microcrystalline cellulose, arabic gum, gelatin, sodium carboxymethyl cellulose, methyl cellulose, hydroxypropyl methyl cellulose, ethyl cellulose, acrylic resin, carbomer, polyvinyl pyrrolidone, polyethylene glycol, etc. Disintegrants can be dry starch, microcrystalline cellulose, low substituted hydroxypropyl cellulose, crosslinked polyvinylpyrrolidone, crosslinked sodium carboxymethyl cellulose, sodium carboxymethyl starch, sodium bicarbonate and citric acid, polyoxyethylene sorbitol fatty acid ester, lauryl sodium sulfonate, etc. Lubricants and cosolvents can be talcum powder, silicon dioxide, stearate, tartaric acid, liquid paraffin, polyethylene glycol, etc.

Tablets can also be further prepared into coated tablets, such as sugar coated tablets, film coated tablets, enteric coated tablets, or bilayer tablets and multilayer tablets.

In order to make the drug delivery unit into capsule, the compound of the present invention as the active ingredient can be mixed with diluents and cosolvents, and the mixture can be directly placed in the hard capsule or soft capsule. The compound of the invention as the active ingredient can also be prepared into granules or pellets with diluents, adhesives and disintegrants, and then placed in hard capsules or soft capsules. The various diluents, adhesives, wetting agents, disintegrants and cosolvents used for preparing the tablets of the compound herein can also be used for preparing capsules of the compound herein.

In order to make the compound of the invention into injection, water, ethanol, isopropanol, propylene glycol or their mixture can be used as solvent, and appropriate amount of commonly used solubilizers, cosolvents, pH regulators and osmotic pressure regulators in the art can be added. Solubilizers or cosolvents can be poloxamer, lecithin, hydroxypropyl-beta-cyclodextrin, etc. pH regulators can be phosphate, acetate, hydrochloric acid, sodium hydroxide, etc. Osmotic pressure regulators can be sodium chloride, mannitol, glucose, phosphate, acetate, etc. If freeze-dried powder injection is prepared, mannitol and glucose can also be added as supporting agents.

Additionally, colorants, preservatives, perfumes, flavouring agents or other additives can also be added to the pharmaceutical preparations if necessary.

In order to achieve the purpose of medication and enhance the therapeutic effect, the compound or pharmaceutical composition of the present invention can be administered by any known method.

Compounds or compositions of the invention may be administered alone or in combination with other therapeutic drugs or symptomatic drugs. When the compound of the invention has synergistic effect with other therapeutic drugs, its dosage should be adjusted according to the actual situation.

Beneficial Technical Effects

The inventors have found that the compounds of the present invention have very strong anti-tuberculosis activity in vitro. The minimum inhibitory concentration (MIC) of seven compounds against *Mycobacterium tuberculosis* in vitro is less than 0.1 μg/mL, which is obviously superior to Linezolid, and has reached or exceeded the anti-tuberculosis activity of Sutezolid. In addition, they display good safety for Vero cells with low cytotoxicity ($IC_{50}$ greater than 30 μg/mL). It is noteworthy that the mitochondrial protein synthesis inhibition of the compounds in the present invention is much weaker than that of the positive control drugs such as Linezolid and Sutezolid, reflecting their higher safety. The compounds of the invention not only demonstrate strong anti-tuberculosis activity and high safety in vitro, but also superior pharmacokinetic properties and excellent in vivo anti-tuberculosis activity. The invention provides a class of benzoxazine oxazolidinone compounds with novel structure, strong activity, low toxicity and excellent pharmacokinetic properties, which can be used for the treatment and prevention of infectious diseases caused by *Mycobacterium tuberculosis*, and even sensitive- or drug-resistant *Mycobacterium tuberculosis*.

The patent WO2011/147259 A1 disclosed on Dec. 1, 2011 the compounds represented by formula (IV) for the treatment of infectious diseases, especially infectious diseases caused by multidrug-resistant bacteria, said infectious diseases are caused by multidrug-resistant bacteria including *Enterococcus, Staphylococcus aureus, Staphylococcus epidermidis* and *Pneumococcus*:

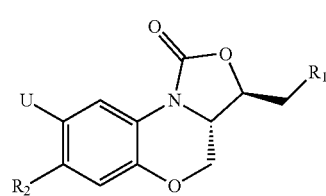

(IV)

wherein, U is H or F, $R_1$ is

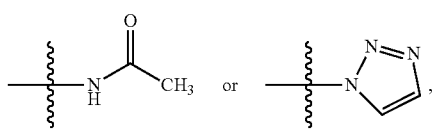

$R_2$ is a phenyl group, or a five membered or six membered aromatic or non-aromatic heterocyclic group.

The patent CN102260277 B which was granted on Jul. 24, 2013 disclosed the compounds represented by the formula (IV), wherein, the $R_2$ is a phenyl group, or a five membered or six membered aromatic heterocyclic group.

Additionally, another document (J. Med. Chem. 2011, 54, 7493-7502) disclosed the following compound:

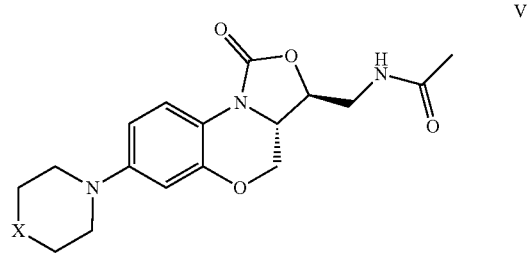

V

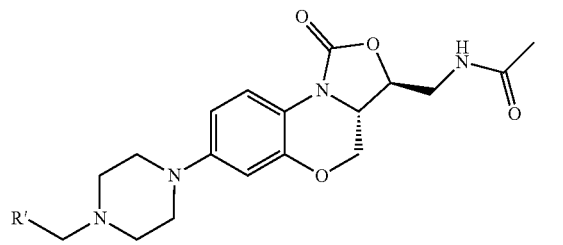

VI wherein, X is N or O, R' is 3-nitrophenyl, 2-nitrophenyl, 4-pyridinyl, 3-pyridinyl, 2-pyridinyl, 2-furanyl, 3-furanyl and 2-nitro-5-furanyl. The document disclosed their activity against *Staphylococcus aureus*, Methicillin-resistant *Staphylococcus aureus*, Methicillin-resistant *Staphylococcus epidermis*, penicillin-resistant *Streptococcus pneumoniae* and *enterococcus*. There is no teaching from the document that the compound has the activity against *Mycobacterium tuberculosis*.

The inventors synthesized the compound represented by formula (VII), i.e. compound when X is oxygen as shown in formula (V) according to the reported synthetic schemes (J. Med. Chem. 2011, 54, 7493-7502) and determined the anti-tuberculosis activity in vitro and mitochondrial protein synthesis inhibition thereof.

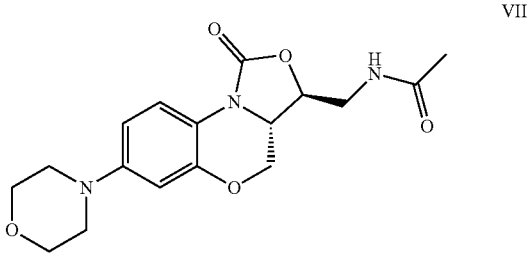

VII

Compound 4

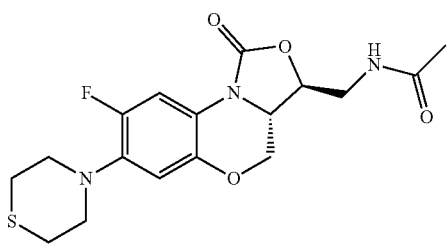

For the compound represented by formula (VII), the MIC value against *Mycobacterium tuberculosis* and the $IC_{50}$ value of mitochondrial protein synthesis inhibition are 1.546 ug/mL and 35.82 μM, respectively. However, for compound 4 in the present invention the MIC value is 0.044 μg/mL, and its anti-tuberculosis activity is significantly stronger than the compound represented by formula (VII) (MIC=1.546 μg/mL). At the same time, for compound 4 the inhibitory effect on mitochondrial protein synthesis is obviously weaker than the compound represented by formula (VII), showing higher safety. The anti-tuberculosis activity of the compound represented by formula (VII) is weaker than that of the compound of the invention, and the anti-drug-resistant tuberculosis activity of the compound represented by formula (VII) is weaker than that of the compound of the invention. In addition, the inhibitory effect of the compound of the invention on mitochondrial protein synthesis is weaker than that of the compound represented by formula (VII), and thus the compound of the present invention has better safety profile.

EXAMPLES

The present invention can be described in detail by the following embodiments, but which does not mean any adverse limitation to the invention. The present invention has been described in detail, and its specific embodiments are also disclosed. For those skilled in the art, it is obvious to make various changes and improvements to the specific embodiments of the invention without departing from the spirit and scope of the invention.

Standard operations and purification methods known to those skilled in the art could be used for all the following examples. Unless otherwise specified, all temperatures are expressed as ° C. (Celsius). The structures of the compounds are determined by nuclear magnetic resonance (NMR) and/or mass spectrometry (MS). Melting point (Mp) is expressed as ° C., and the temperature is not corrected.

PREPARATION EXAMPLE SECTION

The structure of the compounds was determined by $^1$H NMR or MS. The chemical shift (δ) of nuclear magnetic resonance Hydrogen spectrum ($^1$H-NMR) is given in units of one millionth (ppm). The coupling constants (J) are reported in Hertz (Hz). NMR spectra were determined on Mercury-400 or Brucker-500 NMR spectrometer, using $CDCl_3$ or DMSO-$d_6$ as solvents and tetramethylsilane (TMS) as the reference standard.

The melting point was determined by Yanaco M.P-500D melting point apparatus made in Japan, and the temperature was not corrected.

High resolution mass spectrometry was determined by Agilent 1100 series LC/MSD trap mass spectrometer.

The electronic balance was Japanese Yanaco LY-300.

200-300 mesh silica gel is generally used in Column chromatography as carrier.

Anhydrous solvents were obtained by standard methods. The other reagents are all commercially available with analytical purity.

The following abbreviations are used in the invention:

ADDP is 1,1'-(azodicarbonyl)-dipiperidine.

DMF is N, N-dimethylformamide.

EDCI is 1-(3-dimethylaminopropyl)-3-ethylcarbodiimide hydrochloride.

HOBt is 1-hydroxybenzotriazole.

TPP is triphenylphosphine.

PREPARATION EXAMPLES

Preparation Example 1

Preparation of ((2R,3S)-3-(((tert-butyldimethylsilyl)oxy)methyl)oxiran-2-yl)methanol (Intermediate 1)

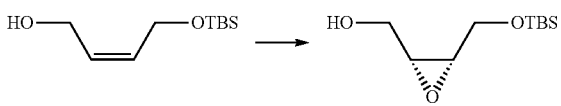

Intermediate 1

To a 500 mL three-necked flask were added 4A molecular sieve (7.2 g) and anhydrous dichloromethane (180 mL). The mixture was cooled to −20° C. under the protection of argon. D-(−)-diethyl tartrate (7.8 mL, 45.7 mmol) was added, followed by titanium tetraisopropanolate (12 mL, 39.8 mmol), and the reaction mixture turned to yellow. After stirring for 0.5 h, (Z)-4-((tert-butyldimethylsilyl)oxy)but-2-en-1-ol (12 g, 59.4 mmol) was added to the mixture and stirred for 1 h with temperature unchanged. tert-Butyl hydroperoxide solution (in toluene, 5 M, 28.5 mL, 142 mmol) was added and stirred overnight with temperature unchanged. After the reaction was complete by TLC monitoring, tartaric acid solution (10%, 192 mL) containing $FeSO_4 \cdot 7H_2O$ (23.4 g, 84 mmol) was added and stirred at 0° C. for 5 h before the reaction stood and layered. The mixture was filtered and the organic phase was separated, the aqueous phase was extracted with dichloromethane for once. The organic phases were combined and concentrated to give an oil. After the oil was dissolved in 100 mL diethyl ether, 1 N sodium hydroxide solution (50 mL) was added dropwise to the mixture in ice-water bath, stirred for 10 minutes, then the diethyl ether layer was separated, which was washed sequentially with water and brine, dried over anhydrous sodium sulfate, filtered to give a pale yellow oil. Column chromatography (petroleum ether/ethyl acetate=9/1) afforded 8.1 g of intermediate 1 as a pale yellow oil, yield: 62.8%.

Preparation Example 2

Preparation of ((2S,3R)-3-(((tert-butyldimethylsilyl)oxy)methyl)oxiran-2-yl)methanol (Intermediate 2)

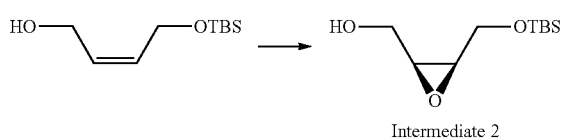 [SMILES: CC(C)(C)[Si](C)(C)OC/C=C\CO ; CC(C)(C)[Si](C)(C)OC[C@H]1O[C@H]1CO]

Intermediate 2

The procedure was the same as in that for preparing intermediate 1, except that L-(+)-diethyl tartrate was used in place of D-(−)-diethyl tartrate to afford 3.0 g of intermediate 2 as a pale yellow oil, yield: 55.6%.

Preparation Example 3

Preparation of ((2R,3S)-3-((trityloxy)methyl)oxiran-2-yl)methanol (Intermediate 3)

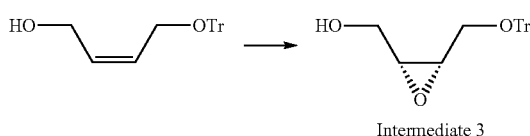

Intermediate 3

To a 1 L four-necked flask were added 4A molecular sieve (12 g) and anhydrous dichloromethane (330 mL). The mixture was cooled to −40° C. under the protection of argon. D-(−)-diethyl tartrate (13.6 mL, 79.2 mmol) was added, followed by titanium tetraisopropanolate (18.8 mL, 63.4 mmol), and the reaction mixture turned to yellow. After stirring for 0.5 h with temperature unchanged, a solution of (Z)-4-(trityloxy)but-2-en-1-ol (26.1 g, 79.2 mmol) in dichloromethane (120 mL) was added to the mixture and stirred for 0.5 h with temperature unchanged. A solution of tert-butyl hydroperoxide in toluene (3.8 M, 50 mL, 190 mmol) was added, stirred for 2 h with temperature unchanged and stirred overnight at −20° C. After the reaction was complete by TLC monitoring, tartaric acid solution (10%, 200 mL) containing $FeSO_4 \cdot 7H_2O$ (30 g) was added and stirred at 0° C. for 1 h before the reaction stood and layered. The organic phase was separated, the aqueous phase was extracted with dichloromethane for twice. The organic phases were combined and washed with brine for twice, filtered, and evaporated to give a solid, which was triturated with n-hexane to obtain 30 g of off-white solid, followed by recrystallization with petroleum ether/ethyl acetate to obtain 15 g of intermediate 3 as an off-white solid with a yield of 57.5%.

Example 1

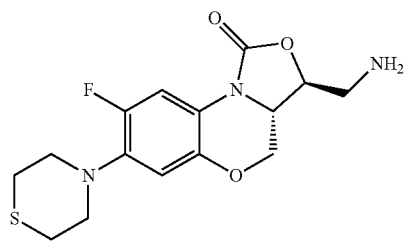 [SMILES: NC[C@@H]1OC(=O)N2c3cc(F)c(N4CCSCC4)cc3OC[C@@H]12]

(3S,3aS)-3-(Aminomethyl)-8-fluoro-7-thiomorpholino-3a, 4-dihydro-1H,3H-benzo[b]ox azolo[3,4-d][1,4]oxazin-1-one (compound 1)

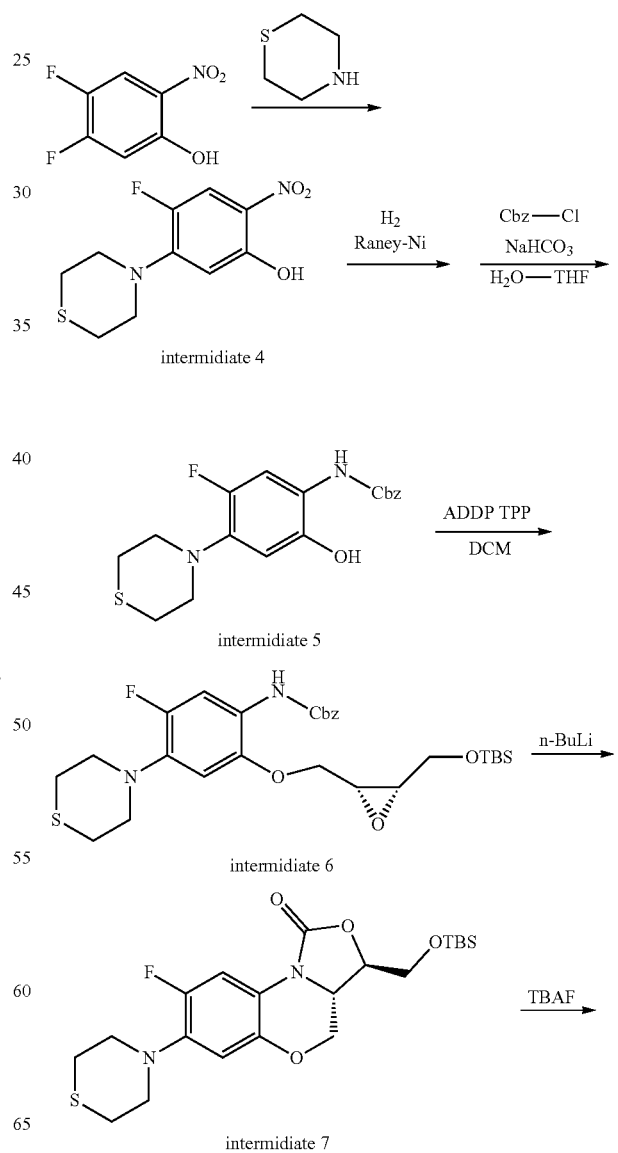

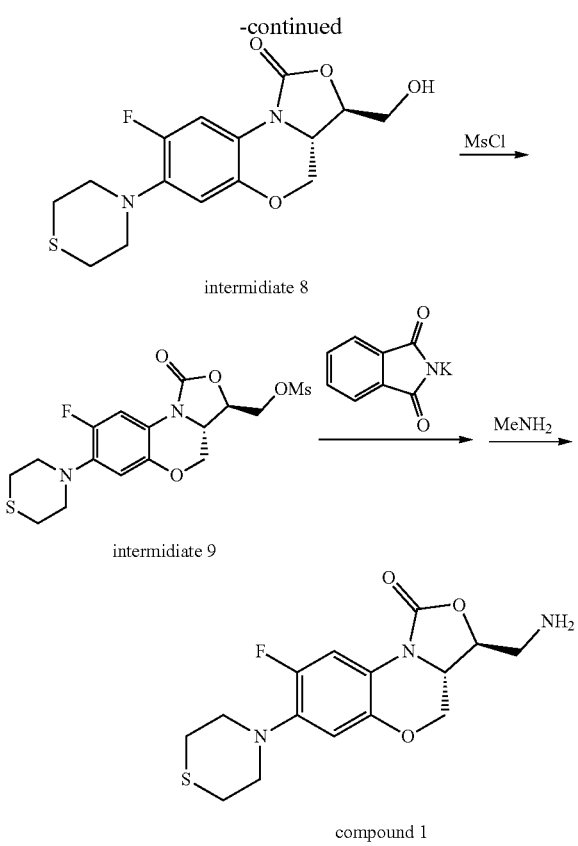

Step 1: Preparation of 4-fluoro-2-nitro-5-thiomorpholinophenol (intermediate 4)

To a solution of 4,5-difluoro-2-nitrophenol (1.75 g, 10 mmol) in acetonitrile (20 mL) was added N-methylmorpholine (1.5 mL), followed by thiomorpholine (11 mL, 11 mmol). The reaction mixture was heated at 80° C. for 3 h. After cooling, water (20 mL) was added to form a solid precipitate which was filtered and washed with water, dried under infrared lamp to give 2.53 g of intermediate 4 as an orange solid with a yield of 98.1%.

$^1$H NMR (400 MHz, CDCl$_3$) δ: 11.20 (s, 1H), 7.64 (d, J=12.4H, 1H), 5.82 (d, J=7.6 Hz, 1H), 4.24 (s, 4H), 3.43 (s, 4H). LC-MS (ESI): m/z [M+H]$^+$: 271.0744.

Step 2: Preparation of benzyl(5-fluoro-2-hydroxy-4-thiomorpholinophenyl)carbamate (intermediate 5)

Intermediate 4 (4 g, 15.5 mmol) was suspended in a mixture of ethanol and tetrahydrofuran (1:1, 40 mL). Raney nickel (1 g) was added and hydrogenated at medium pressure for 2 hours. The reaction mixture was filtered into a flask containing sodium bicarbonate (2.6 g, 31 mmol) and water (10 mL), protected by argon. Benzyl chloroformate (1.95 mL, 14.4 mmol) was added dropwise under ice bath, and stirred for 20 minutes with temperature unchanged. The organic phase was washed with brine, dried over anhydrous sodium sulfate, filtered and concentrated to give a red solid. The crude product was purified by silica gel column chromatography eluted with petroleum ether/ethyl acetate=7/3 to give intermediate 5 (4.5 g, 80.4%) as a pink solid.

LC-MS (ESI): m/z [M+H]$^+$: 363.1905.

Step 3 Preparation of benzyl (2-(((2R,3S)-3-(((tert-butyldimethylsilyl)oxy)methyl)oxiran-2-yl)methoxy)-5-fluoro-4-thiomorpholinophenyl)carbamate (intermediate 6)

To a 50 mL two-necked flask were added intermediate 5 (1 g, 2.76 mmol), intermediate 1 (0.9 g, 4.14 mmol), triphenylphosphine (1.45 g, 5.52 mmol) and anhydrous dichloromethane (20 mL), and then ADDP (1.39 g, 5.52 mmol) was added in four batches. After the reaction was complete by TLC monitoring, n-hexane was added for dilution, the reaction was filtered, and the filtrate was concentrated. The crude product was purified by silica gel column chromatography eluted with petroleum ether/ethyl acetate=92/8 to give a pale yellow oil which was solidified at room temperature to obtain intermediate 6 (1.2 g, 77.4%).

$^1$H NMR (400 MHz, CDCl$_3$) δ: 7.92 (d, J=12.4 Hz, 1H), 7.44-7.31 (m, 5H), 7.19 (brs, 1H), 6.59 (brs, 1H), 5.20 (s, 2H), 4.31 (dd, J=11.6, 3.2 Hz, 1H), 4.04 (dd, J=11.6, 7.2 Hz, 1H), 3.91-3.79 (m, 2H), 3.40-3.20 (m, 6H), 2.81 (brs, 4H), 0.90 (s, 9H), 0.10 (s, 3H), 0.09 (s, 3H). LC-MS (ESI): m/z [M+H]$^+$: 563.2954.

Step 4 Preparation of (3R,3aS)-3-(((tert-butyldimethylsilyl)oxy)methyl)-8-fluoro-7-thiomorpholino-3a,4-dihydro-1H,3H-benzo[b]oxazolo[3,4-d][1,4]oxazin-1-one (intermediate 7)

To a solution of intermediate 6 (1.7 g, 3.02 mmol) in anhydrous tetrahydrofuran (30 mL) under the protection of argon at −78° C. was added n-BuLi (1.6 M in n-hexane 2 mL, 3.3 mmol) dropwise. After addition, the resulting mixture was stirred for 1.5 h with temperature unchanged, then warmed to room temperature and stirred overnight. Saturated ammonium chloride (2 mL) was added to quench the reaction. The solvent was evaporated, and ethyl acetate and water were added. Organic phase was separated, and aqueous phase was extracted with ethyl acetate again. The combined organic phases were washed with brine, dried over anhydrous sodium sulfate, filtered, and concentrated in vacuum to give a light pink solid. The residue was purified by silica gel column chromatography eluted with petroleum ether/dichloromethane/ethyl acetate=80/10/10 to give intermediate 7 (1.29 g, 94.2%) as an off-white solid.

$^1$H NMR (400 MHz, CDCl$_3$) δ: 7.73 (d, J=12.8 Hz, 1H), 6.61 (d, J=6.8 Hz, 1H), 4.42 (dd, J=10.4, 3.2 Hz, 1H), 4.28-4.22 (m, 1H), 4.09-4.02 (m, 1H), 3.96-3.81 (m, 3H), 3.28 (m, 4H), 2.82 (t, J=4.8 Hz, 4H), 0.90 (s, 9H), 0.11 (s, 3H), 0.10 (s, 3H). LC-MS (ESI): m/z [M+H]$^+$ 455.2620.

Step 5 Preparation of (3R,3aS)-8-fluoro-3-(hydroxymethyl)-7-thiomorpholino-3a,4-dihydro-1H,3H-benzo[b]oxazolo[3,4-d][1,4]oxazin-1-one (intermediate 8)

To a solution of intermediate 7 (1.2 g 2.64 mmol) in THF (10 mL) in a 50 mL flask placed in an ice-water bath was added tetrabutylammonium fluoride (3.2 mL, 3.2 mmol, 1 M in tetrahydrofuran). After stirring for 0.5 hours, the solid can be precipitated by adding water. The mixture was filtered and the filter cake was washed with water, dried to afford intermediate 8 (0.70 g, 78.3%) as an off-white solid.

Step 6 Preparation of ((3R,3aS)-8-fluoro-1-oxo-7-thiomorpholino-3a,4-dihydro-1H,3H-benzo[b]oxazolo[3,4-d][1,4]oxazin-3-yl)methyl methanesulfonate (intermediate 9)

To a solution of intermediate 8 (1.0 g, 2.94 mmol) in dichloromethane (20 mL) in a 50 mL two-necked flask cooled to 0° C. with ice-water bath was added triethylamine (1.2 mL, 8.8 mmol), and then methanesulfonyl chloride (0.34 mL, 4.4 mmol) was added. The reaction mixture was concentrated to give a solid. The residue was added with water and filtered to give intermediate 9 (1.11 g, 90.2%) as a light red solid.

$^1$H NMR (400 MHz, CDCl$_3$) δ: 7.70 (dd, J=12.8, 1.0 Hz, 1H), 6.61 (d, J=7.9 Hz, 1H), 4.57-4.46 (m, 4H), 4.13-4.05 (m, 1H), 3.87 (t, J=10.2 Hz, 1H), 3.35-3.22 (m, 4H), 3.14 (s, 3H), 2.82 (t, J=4.8 Hz, 4H). LC-MS (ESI): m/z [M+H]$^+$ 419.1083.

Step 7 Preparation of (3S,3aS)-3-(aminomethyl)-8-fluoro-7-thiomorpholino-3a,4-dihydro-1H,3H-benzo[b]oxazolo[3,4-d][1,4]oxazin-1-one (compound 1)

Intermediate 9 (1.1 g, 2.63 mmol) was dissolved in DMF (20 mL). Phthalimide potassium (1.09 g, 5.88 mmol) was added and the mixture was allowed to react at 80° C. for 5 hours. Then, ice-water (20 mL) was added after cooling. A solid was precipitated, filtered, washed and dried to give a light pink solid. The solid was added to a sealed tube, then a solution of methylamine in methanol (5 mL) was added. The reaction mixture was heated at 80° C. for 4 hours. After cooling, water was added for dilution, and the mixture was extracted with ethyl acetate for 3 times. The combined organic phases were washed with brine for once, dried over anhydrous sodium sulfate, filtered and concentrated under reduced pressure. The residue was purified by silica gel column chromatography to obtain compound 1 (250 mg, 25.0%) as a light yellow solid. Mp: 155-157° C.

$^1$H NMR (400 MHz, CDCl$_3$) δ: 7.75 (d, J=13.0 Hz, 1H), 6.55 (d, J=7.8 Hz, 1H), 4.45 (dd, J=10.4, 3.0 Hz, 1H), 4.29-4.23 (m, 1H), 4.07-4.00 (m, 1H), 3.86 (t, J=10.2 Hz, 1H), 3.32-3.20 (m, 4H), 3.19-3.04 (m, 2H), 2.83-2.76 (m, 4H), 1.41 (brs, 2H). HR-MS (ESI): m/z [M+H]$^+$ calcd for C$_{15}$H$_{19}$FN$_3$O$_3$S: 340.1126; found: 340.1111.

Example 2

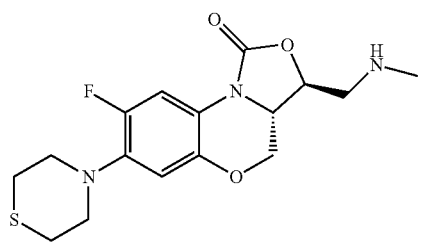 [SMILES: CNC[C@@H]1OC(=O)N2c3cc(F)c(N4CCSCC4)cc3OC[C@@H]12]

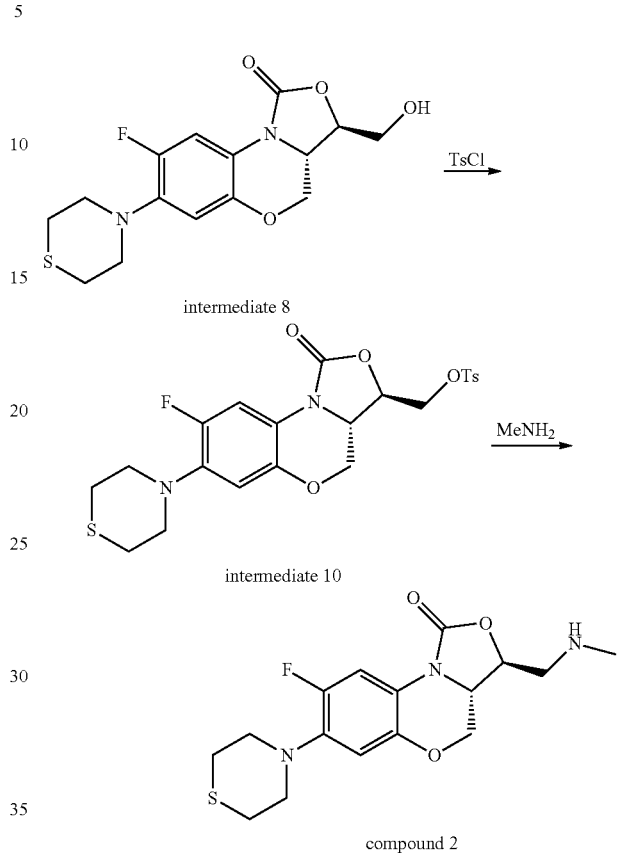

intermediate 8 intermediate 10 compound 2

Step 1 Preparation of ((3R,3aS)-8-fluoro-1-oxo-7-thiomorpholino-3a,4-dihydro-1H,3H-benzo[b]oxazolo[3,4-d][1,4]oxazin-3-yl)methyl-4-methyl benzenesulfonate (intermediate 10)

Intermediate 8 (1.2 g, 3.53 mmol) was added to a 50 mL two-necked flask and dissolved in dichloromethane (30 mL). The temperature was cooled to 0° C. with ice-water bath, and triethylamine (0.99 mL, 7.06 mmol) and DMAP (50 mg) were added, and then p-methylbenzenesulfonyl chloride (0.81 g, 4.24 mmol) was added in portions. After stirring for 1 hour with temperature unchanged, the reaction was diluted with dichloromethane, washed sequentially with water, 10% citric acid, saturated sodium bicarbonate solution and brine, dried over anhydrous sodium sulfate, filtered. The filtrate was concentrated under reduced pressure, and purified by silica gel column chromatography (dichloromethane/ethyl acetate=80/20) to give intermediate 10 (1.59 g, 85.0%) as a white solid.

Step 2 Preparation of (3S,3aS)-8-Fluoro-3-((methylamino)methyl)-7-thiomorpholino-3a,4-dihydro-1H,3H-benzo[b]oxazolo[3,4-d][1,4]oxazin-1-one (compound 2)

Intermediate 10 (0.090 g, 0.17 mmol) was added to the sealed tube, methanol solution (3 mL) of methylamine and tetrahydrofuran (3 mL) were added, heated at 100° C. for 1 h. The reaction solution was concentrated and purified by silica gel column chromatography (dichloromethane/methanol/ammonium hydroxide=100/2/1) to obtain compound 2 (30 mg, 50.0%) as an off-white solid. Mp: 155-156° C.

$^1$H NMR (400 MHz, CDCl$_3$) δ: 7.75 (d, J=13.0 Hz, 1H), 6.54 (d, J=7.9 Hz, 1H), 6.03 (brs, 1H), 4.44 (dd, J=10.4, 3.0 Hz, 1H), 4.35 (dd, J=12.2, 5.4 Hz, 1H), 4.08-3.98 (m, 1H), 3.84 (t, J=10.2 Hz, 1H), 3.33-3.20 (m, 4H), 3.04-2.91 (m, 2H), 2.83-2.75 (m, 4H), 2.51 (s, 3H). HR-MS (ESI): m/z [M+H]$^+$ calcd for C$_{16}$H$_{21}$FN$_3$O$_3$S: 354.1282; found: 354.1275.

Example 3

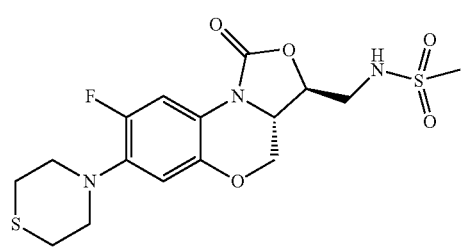 [SMILES: CS(=O)(=O)NC[C@@H]1OC(=O)N2c3cc(F)c(N4CCSCC4)cc3OC[C@@H]12]

N-(((3S,3aS)-8-Fluoro-1-oxo-7-thiomorpholino-3a, 4-dihydro-1H,3H-benzo[b]oxazolo[3,4-d][1,4]oxazin-3-yl)methyl)methanesulfonamide (compound 3)

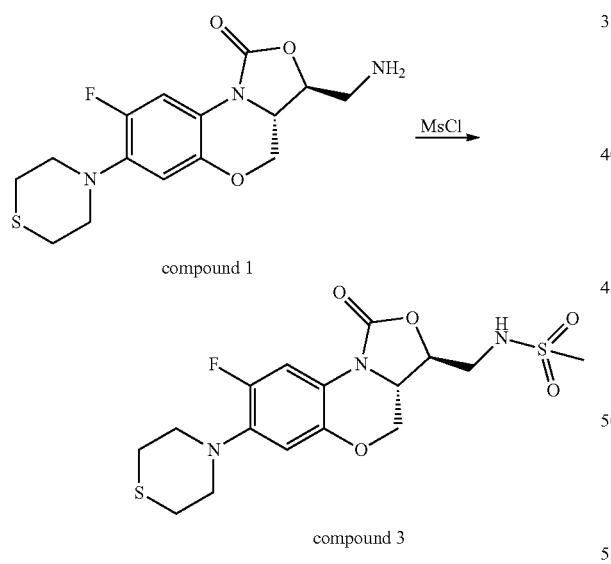

To a solution of compound 1 (0.070 g, 0.175 mmol) in dichloromethane (4 mL) was added triethylamine (0.037 mL, 0.26 mmol), cooled in ice bath. Methylsulfonyl chloride (0.016 mL, 0.21 mmol) was added. After the reaction was complete by TLC monitoring, the solvent was concentrated and removed. The residue was purified by silica gel column chromatography (dichloromethane/methanol=99/1) to give compound 3 (43 mg, 51.8%) as off-white solid. Mp: 234-235° C.

$^1$H NMR (400 MHz, DMSO-d$_6$) δ: 7.61-7.51 (m, 2H), 6.68 (d, J=8.2 Hz, 1H), 4.55-4.47 (m, 2H), 4.04-3.94 (m, 2H), 3.50-3.35 (m, 2H), 3.17 (brs, 4H), 2.96 (s, 3H), 2.77-2.69 (m, 4H). HR-MS (ESI): m/z [M+H]$^+$ calcd for C$_{16}$H$_{21}$FN$_3$O$_5$S$_2$: 418.0901; found: 418.0894.

Example 4

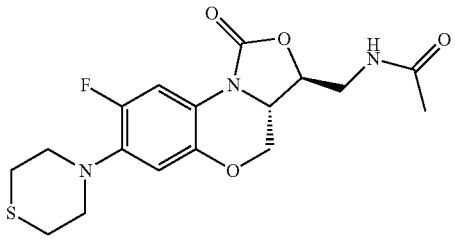 [SMILES: CC(=O)NC[C@@H]1OC(=O)N2c3cc(F)c(N4CCSCC4)cc3OC[C@@H]12]

N-(((3S,3aS)-8-Fluoro-1-oxo-7-thiomorpholino-3a, 4-dihydro-1H,3H-benzo[b]oxazolo[3,4-d][1,4]oxazin-3-yl)methyl)acetamide (compound 4)

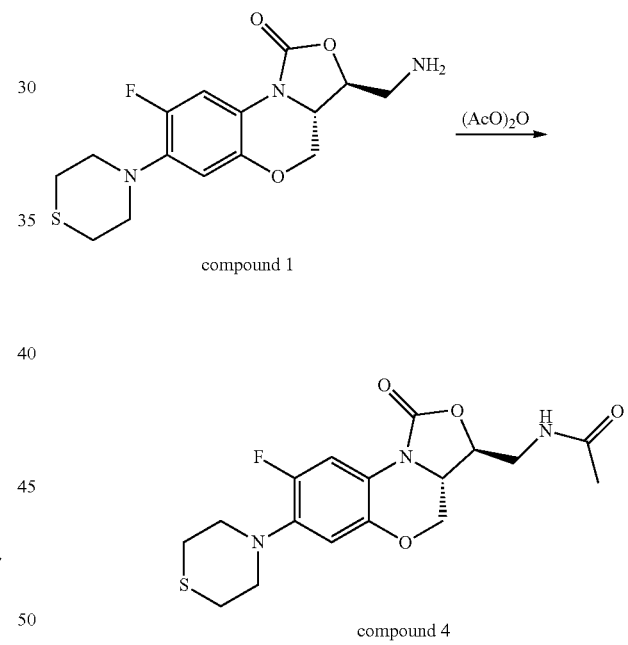

To a solution of compound 1 (0.18 g, 0.53 mmol) in dichloromethane (6 mL) was added pyridine (0.086 mL, 1.06 mmol), cooled in an ice bath. Acetic anhydride (0.076 mL, 0.8 mmol) was added and then stirred for 40 mins. The solvent was concentrated and removed. The residue was purified by silica gel column chromatography (dichloromethane/methanol=99/1) to give compound 4 (128 mg, 63.4%) as an off-white solid. Mp: 190-192° C.

$^1$H NMR (400 MHz, CDCl$_3$) δ: 7.76 (d, J=13.0 Hz, 1H), 6.83 (brs, 1H), 5.96 (t, J=6.0 Hz, 1H), 4.51 (dd, J=10.4, 2.8 Hz, 1H), 4.43-4.37 (m, 1H), 3.95-3.88 (m, 1H), 3.82 (t, J=10.2 Hz, 1H), 3.79-3.63 (m, 2H), 3.39-3.31 (m, 4H), 2.89 (brs, 4H), 2.05 (s, 3H). HR-MS (ESI): m/z [M+H]$^+$ calcd for C$_{17}$H$_{21}$FN$_3$O$_4$S: 382.1231; found: 382.1222.

Example 5

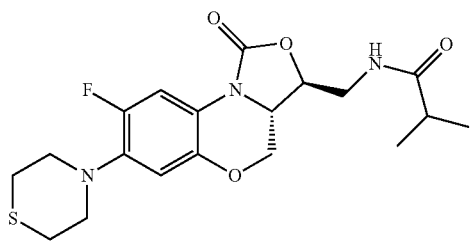 [SMILES: CC(C)C(=O)NC[C@@H]1OC(=O)N2c3cc(F)c(N4CCSCC4)cc3OC[C@@H]12]

N-(((3S,3aS)-8-Fluoro-1-oxo-7-thiomorpholino-3a, 4-dihydro-1H,3H-benzo[b]oxazolo[3,4-d][1,4] oxazin-3-yl)methyl)isobutyramide (compound 5)

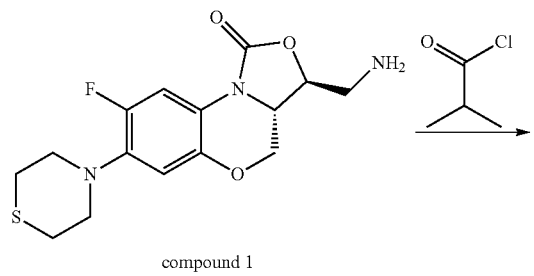

compound 1

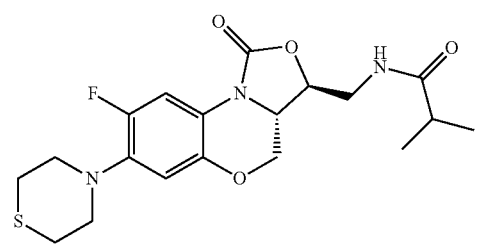

compound 5

To a solution of compound 1 (0.055 g, 0.16 mmol) in dichloromethane (6 mL) was added triethylamine (0.034 mL, 0.24 mmol), cooled in ice bath. Isobutyryl chloride (0.020 mL, 0.18 mmol) was added and then the resulting mixture was stirred for 30 min. The solvent was concentrated and removed. The residue was purified by silica gel column chromatography (dichloromethane/methanol=99/1) to give compound 5 (38 mg, 58.5%) as off-white solid. Mp: 193-195° C.

$^1$H NMR (400 MHz, CDCl$_3$) δ: 7.76 (d, J=13.0 Hz, 1H), 7.01 (brs, 1H), 6.06 (t, J=5.4 Hz, 1H), 4.51 (dd, J=10.4, 2.6 Hz, 1H), 4.45-4.36 (m, 1H), 4.00-3.87 (m, 1H), 3.86-3.62 (m, 3H), 3.41 (brs, 4H), 2.94 (brs, 4H), 2.49-2.36 (m, 1H), 1.17 (d, J=4.0 Hz, 3H), 1.16 (d, J=4.0 Hz, 3H). HR-MS (ESI): m/z [M+H]$^+$ calcd for C$_{19}$H$_{25}$FN$_3$O$_4$S: 410.1544; found: 410.1528.

Example 6

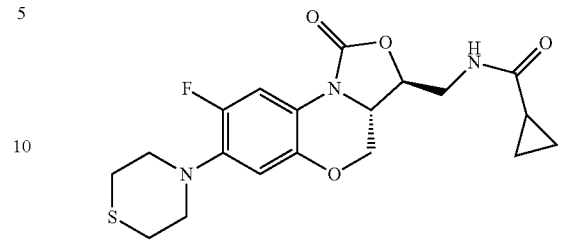

N-(((3S,3aS)-8-Fluoro-1-oxo-7-thiomorpholino-3a, 4-dihydro-1H,3H-benzo[b]oxazolo[3,4-d][1,4] oxazin-3-yl)methyl)cyclopropanecarboxamide (compound 6)

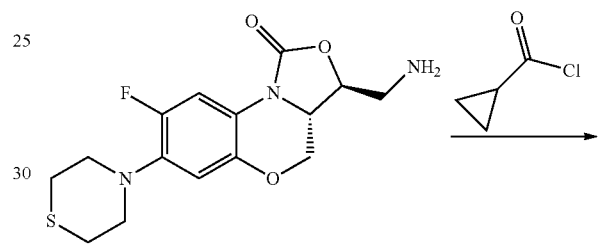

compound 1

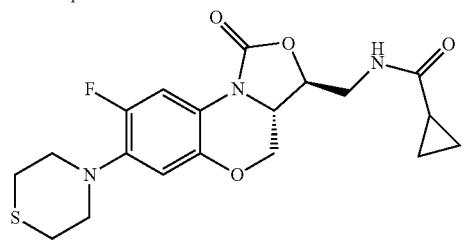

compound 6

To a solution of compound 1 (0.10 g, 0.30 mmol) in tetrahydrofuran (7 mL) was added triethylamine (0.13 mL, 0.9 mmol), cooled in ice bath. Cyclopropanecarbonyl chloride (0.035 mL, 0.39 mmol) was added and then the resulting mixture was stirred for 15 mins. The solvent was concentrated and removed. The residue was diluted with dichloromethane and washed with saturated brine, dried over anhydrous sodium sulfate, filtered and concentrated under reduced pressure. The residue was purified by silica gel column chromatography (dichloromethane/methanol=99/1) to obtain compound 6 (86 mg, 70.5%) as an off-white solid. Mp. 209-211° C.

$^1$H NMR (400 MHz, CDCl$_3$) δ: 7.74 (d, J=12.8 Hz, 1H), 6.60 (d, J=7.6 Hz, 1H), 6.16 (t, J=6.0 Hz, 1H), 4.48 (dd, J=10.2, 2.8 Hz, 1H), 4.43-4.36 (m, 1H), 3.95-3.88 (m, 1H), 3.82 (t, J=10.2 Hz, 1H), 3.79-3.65 (m, 2H), 3.32-3.23 (m, 4H), 2.86-2.76 (m, 4H), 1.45-1.36 (m, 1 H), 1.01-0.94 (m, 2H), 0.85-0.77 (m, 2H). HR-MS (ESI): m/z [M+H]$^+$ calcd for C$_{19}$H$_{23}$FN$_3$O$_4$S: 408.1388; found: 408.1379.

Example 7

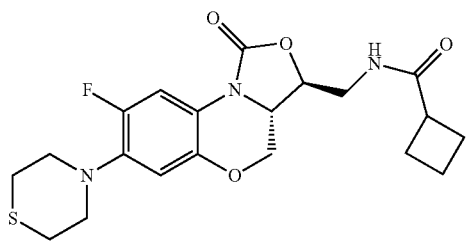 [SMILES: O=C(NC[C@@H]1OC(=O)N2c3cc(F)c(N4CCSCC4)cc3OC[C@@H]12)C1CCC1]

N-(((3S,3aS)-8-Fluoro-1-oxo-7-thiomorpholino-3a,4-dihydro-1H,3H-benzo[b]oxazolo[3,4-d][1,4]oxazin-3-yl)methyl)cyclobutanecarboxamide (compound 7)

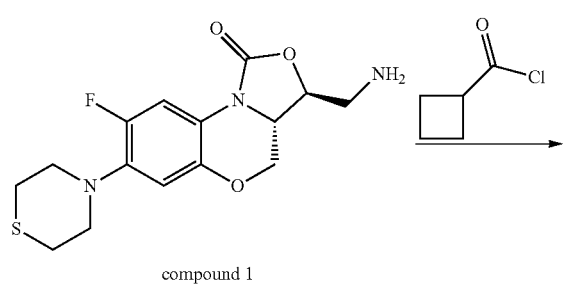

To a solution of compound 1 (0.098 g, 0.29 mmol) in dichloromethane (3 mL) was added triethylamine (0.081 mL, 0.58 mmol), cooled in an ice bath. Cyclobutanecarbonyl chloride (0.037 mL, 0.37 mmol) was added and then the resulting mixture was stirred for 2 hours. The resulting mixture was diluted with dichloromethane and washed with saturated brine, dried over anhydrous sodium sulfate, filtered and concentrated under reduced pressure. The residue was purified by silica gel column chromatography (dichloromethane/methanol=99/1) to obtain compound 7 (30 mg, 24.8%) as an off-white solid. Mp. 176-178° C.

$^1$H NMR (400 MHz, CDCl$_3$) δ: 7.71 (d, J=12.8 Hz, 1H), 6.63 (d, J=7.4 Hz, 1H), 5.83 (t, J=6.0 Hz, 1H), 4.50 (dd, J=10.2, 2.8 Hz, 1H), 4.42-4.36 (m, 1H), 3.94-3.86 (m, 1H), 3.82 (t, J=10.2 Hz, 1H), 3.78-3.71 (m, 1H), 3.71-3.62 (m, 1H), 3.36-3.22 (m, 4H), 3.11-2.97 (m, 1H), 2.89-2.76 (m, 4H), 2.34-2.11 (m, 4H), 2.07-1.81 (m, 2H). HR-MS (ESI) m/z [M+H]$^+$ calcd for C$_{20}$H$_{25}$FN$_3$O$_4$S: 422.1544; found: 422.1534.

Example 8

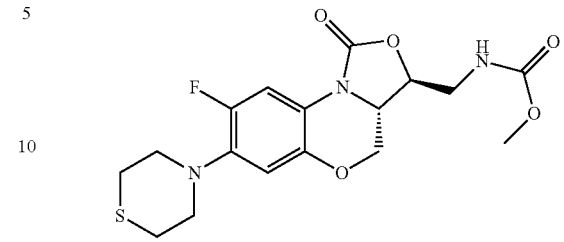

Methyl (((3S,3aS)-8-Fluoro-1-oxo-7-thiomorpholino-3a,4-dihydro-1H,3H-benzo[b]oxazolo[3,4-d][1,4]oxazin-3-yl)methyl)carbamate (compound 8)

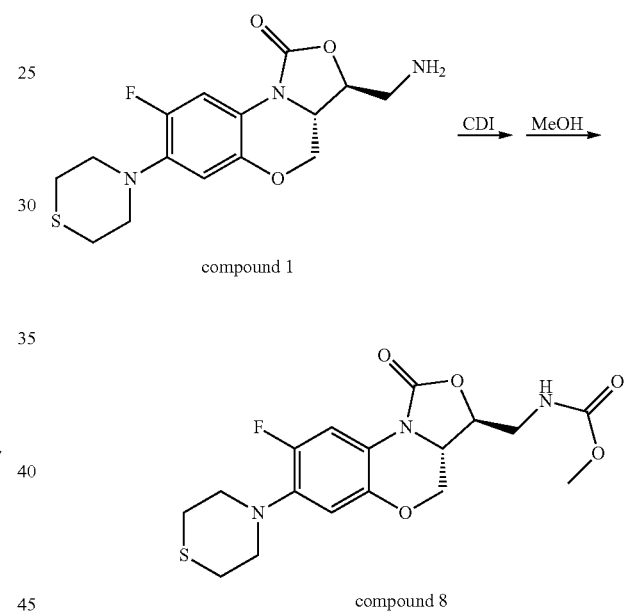

To a solution of compound 1 (0.10 g, 0.29 mmol) in tetrahydrofuran (9 mL) was added 1,1'-carbonyldiimidazole (CDI, 0.49 g, 3 mmol) and stirred at room temperature for 50 minutes. Anhydrous methanol (3 mL) was added and then the resulting mixture was stirred overnight at room temperature. The solvent was evaporated, and then the residue was diluted with dichloromethane. The resulting mixture was washed with saturated ammonium chloride solution, saturated brine, dried over anhydrous sodium sulfate, filtered, and concentrated. The residue was purified by silica gel column chromatography (petroleum ether/ethyl acetate=60/40) to obtain compound 8 (77 mg, 64.7%) as a white solid. Mp. 155-156° C.

$^1$H NMR (400 MHz, CDCl$_3$) δ: 7.74 (d, J=12.8 Hz, 1H), 6.66 (d, J=5.8 Hz, 1H), 5.16 (brs, 1H), 4.49 (dd, J=10.4, 3.0 Hz, 1H), 4.41-4.35 (m, 1H), 3.99-3.91 (m, 1H), 3.84 (t, J=10.2 Hz, 1H), 3.70 (s, 3H), 3.67-3.58 (m, 2H), 3.26-3.24 (m, 4H), 2.83 (t, J=4.8 Hz, 4H). HR-MS (ESI): m/z [M+H]$^+$ calcd for C$_{17}$H$_{21}$FN$_3$O$_5$S: 398.1180; found: 398.1172.

Example 9

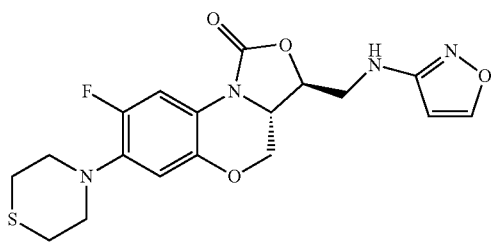 [SMILES: O=C1O[C@@H](CNc2ccon2)[C@@H]2COc3cc(N4CCSCC4)c(F)cc3N12]

(3S,3aS)-8-Fluoro-3-((isoxazol-3-ylamino)methyl)-7-thiomorpholino-3a,4-dihydro-1H,3H-benzo[b]oxazolo[3,4-d][1,4]oxazin-1-one (compound 9)

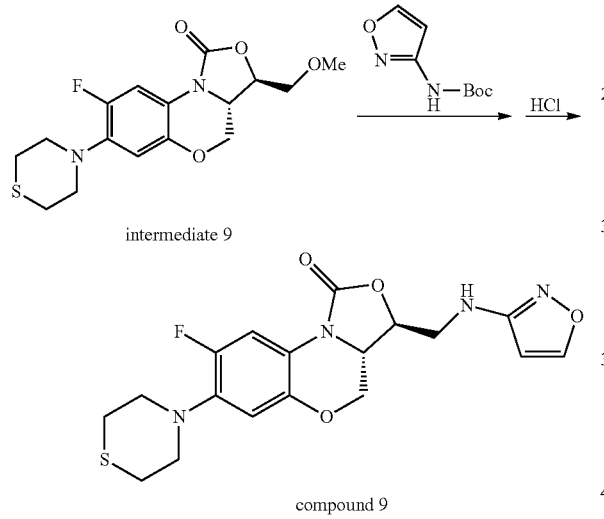

To a solution of N-Boc-3-aminoisoxazole (0.057 g, 0.31 mmol) in anhydrous DMF (2 mL) cooed with in an ice-water bath was added NaH (60%, 15 mg, 0.34 mmol). After stirring for 5 minutes, intermediate 9 (0.13 g, 0.31 mmol) was added and reacted at 70° C. for 2 hours. After cooling, ice water was added dropwise (10 mL), and the mixture was extracted with dichloromethane twice, and the organic phases were combined. The organic phase was washed with brine, dried over anhydrous sodium sulfate, filtered and concentrated. The residue was purified by silica gel column chromatography (petroleum ether/ethyl acetate=85/15) to give 141 mg oil with a yield of 89.8%.

To a solution of the above oil in ethyl acetate (2 mL) was added methanol solution of hydrogen chloride (5 N, 4 mL), and stirred at room temperature for 30 minutes. Solvent was evaporated, water (3 mL) was added, and the pH was adjusted to alkalinity using saturated sodium bicarbonate. The solid was precipitated and filtered. The filter cake was washed with water until neutral, dried to afford compound 9 (94 mg, 75.2%) as a white solid. Mp. 148-150° C.

$^1$H NMR (400 MHz, CDCl$_3$) δ: 8.08 (d, J=1.8 Hz, 1H), 7.73 (d, J=12.8 Hz, 1H), 6.55 (d, J=7.8 Hz, 1H), 5.88 (d, J=1.8 Hz, 1H), 4.61-4.54 (m, 1H), 4.51 (dd, J=10.4, 3.0 Hz, 1H), 4.35 (t, J=6.4 Hz, 1H), 4.05-3.98 (m, 1H), 3.86 (t, J=10.2 Hz, 1H), 3.82-3.74 (m, 1H), 3.74-3.65 (m, 1H), 3.31-3.20 (m, 4H), 2.79 (t, J=5.2 Hz, 4H). HR-MS (ESI): m/z [M+H]$^+$ calcd for C$_{18}$H$_{20}$FN$_4$O$_4$S: 407.1184; found: 407.1174.

Example 10

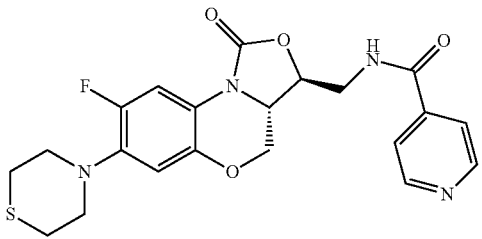 [SMILES: O=C(NC[C@@H]1OC(=O)N2c3cc(F)c(N4CCSCC4)cc3OC[C@@H]12)c1ccncc1]

N-(((3S,3aS)-8-Fluoro-1-oxo-7-thiomorpholino-3a,4-dihydro-1H,3H-benzo[b]oxazolo[3,4-d][1,4]oxazin-3-yl)methyl)isonicotinamide (compound 10)

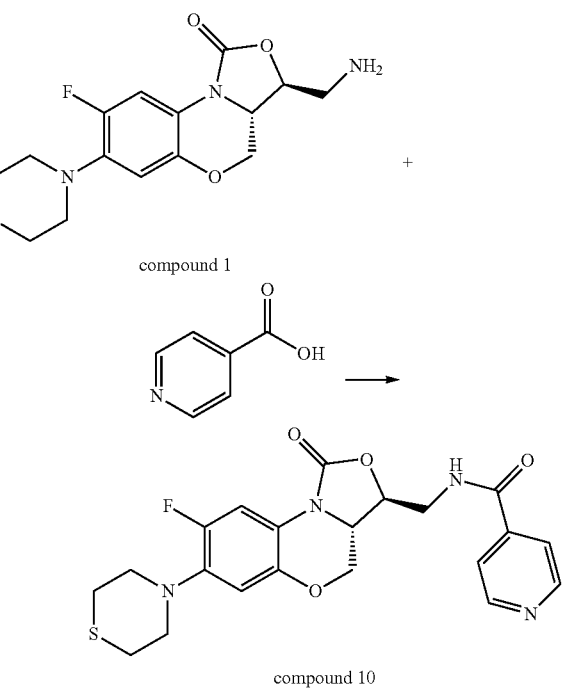

Compound 1 (60 mg, 0.18 mmol), isonicotinic acid (26 mg, 0.21 mmol), EDCI (40 mg, 0.21 mmol), HOBt (28 mg, 0.21 mmol) and triethylamine (0.050 mL, 0.35 mmol) were added to a 5 mL flask. DMF (2 mL) was added and the mixture was stirred overnight at room temperature. A solid was precipitated by adding ice water and filtered. The obtained solid was dissolved in dichloromethane and purified by silica gel (200-300 mesh) column chromatography (dichloromethane/ethyl acetate/methanol=50/50/1) to obtained compound 10 (46 mg, 59.0%) as a white solid. Mp. 135-137° C.

$^1$H NMR (400 MHz, CDCl$_3$) δ: 8.77 (d, J=4.4 Hz, 2H), 7.69 (d, J=5.6 Hz, 2H), 7.65 (d, J=12.8 Hz, 1H), 7.35 (t, J=5.8 Hz, 1H), 6.55 (d, J=7.8 Hz, 1H), 4.61-4.49 (m, 2H), 4.03-3.92 (m, 2H), 3.93-3.82 (m, 2H), 3.33-3.18 (m, 4H), 2.8-2.75 (m, 4H). HR-MS (ESI): m/z [M+H]+ calcd for $C_{21}H_{22}FN_4O_4S$: 445.1340; found: 445.1324.

Example 11

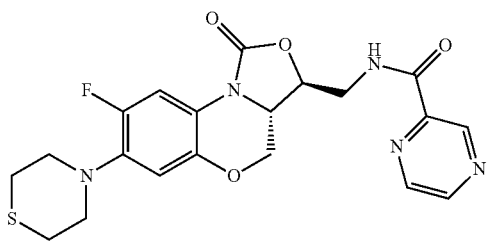 [SMILES: O=C(NC[C@@H]1OC(=O)N2c3cc(F)c(N4CCSCC4)cc3OC[C@@H]12)c1cnccn1]

N-(((3S,3aS)-8-Fluoro-1-oxo-7-thiomorpholino-3a,4-dihydro-1H,3H-benzo[b]oxazolo[3,4-d][1,4]oxazin-3-yl)methyl)pyrazine-2-carboxamide (compound 11)

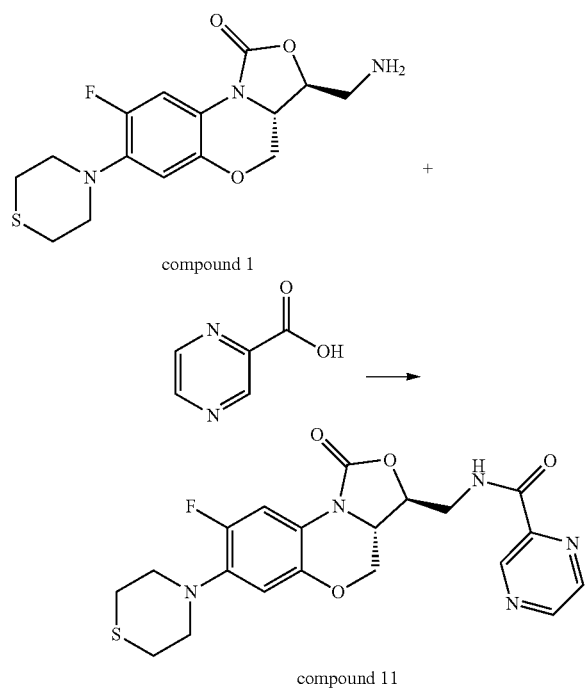

Compound 1 (60 mg, 0.18 mmol), 2-pyrazinecarboxylic acid (25 mg, 0.21 mmol), EDCI (40 mg, 0.21 mmol), HOBt (28 mg, 0.21 mmol) and triethylamine (0.050 mL, 0.35 mmol) were added to a 5 mL flask. DMF (2 mL) was added and the mixture was stirred overnight at room temperature. A solid was precipitated by adding ice water, filtered and dissolved with dichloromethane and purified by silica gel (200-300 mesh) column chromatography (dichloromethane/ethyl acetate/methanol=50/50/1) to obtain compound 11 (41 mg, 51.9%) as a pale-yellow solid. Mp. 212-214° C.

$^1$H NMR (400 MHz, CDCl$_3$) δ: 9.38 (d, J=1.2 Hz, 1H), 8.80 (d, J=2.4 Hz, 1H), 8.57 (dd, J=2.2, 1.4 Hz, 1H), 8.27 (t, J=6.0 Hz, 1H), 7.73 (d, J=12.8 Hz, 1H), 6.68 (brs, 1H), 4.60-4.46 (m, 2H), 4.08-3.81 (m, 4H), 3.37-3.22 (m, 4H), 2.83 (brs, 4H). HR-MS (ESI): m/z [M+H]+ calcd for $C_{20}H_{21}FN_5O_4S$: 446.1298; found: 445.1276.

Example 12

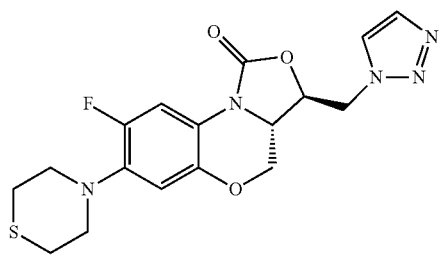 [SMILES: O=C1O[C@@H](Cn2ccnn2)[C@@H]2COc3cc(N4CCSCC4)c(F)cc3N12]

(3S,3aS)-3-((1H-1,2,3-Triazol-1-yl)methyl)-8-fluoro-7-thiomorpholino-3a,4-dihydro-1H,3H-benzo[b]oxazolo[3,4-d][1,4]oxazin-1-one (compound 12)

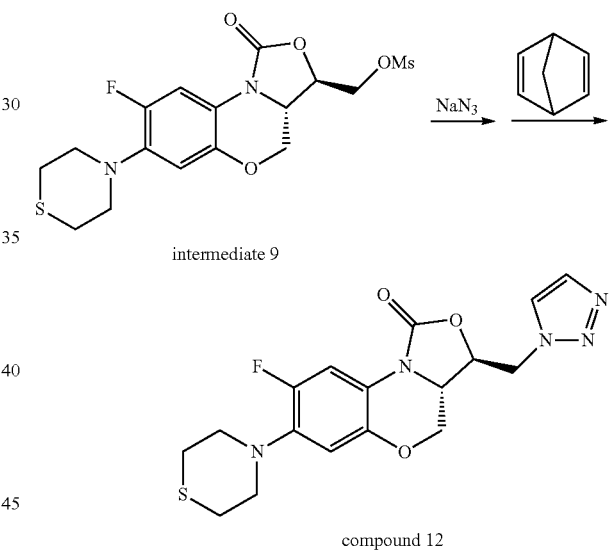

Intermediate 9 (418 mg, 1 mmol) was dissolved in DMF (10 mL). Sodium azide (130 mg, 2 mmol) was added to the solution. The reaction mixture was heated at 80° C. for 2.5 hrs and then cooled to room temperature. After adding ice water (10 mL), a solid was precipitated, filtered, washed with water, and dried under infrared lamp to give 351 mg as an off-white solid with a yield of 96.2%.

LC-MS (ESI): m/z [M+H]+: 366.8012.

The above solid (0.11 g, 0.3 mmol) was dissolved in 1,4-dioxane (3 mL), and dicycloheptadiene (0.31 mL, 3 mmol) was added. The reaction mixture was refluxed for 5 hours, and the solvent was evaporated. The resulting residue was purified by silica gel (200-300 mesh) column chromatography (dichloromethane/methanol=99/1) to give compound 12 (83 mg, 70.9%) as an off-white solid. Mp. 223-225° C.

$^1$H NMR (400 MHz, CDCl$_3$) δ: 7.80-7.77 (m, 2H), 7.64 (d, J=12.8 Hz, 1H), 6.64 (d, J=6.6 Hz, 1H), 4.84 (d, J=4.8 Hz, 2H), 4.72-4.66 (m, 1H), 4.46 (dd, J=10.6, 3.0 Hz, 1H), 4.08-4.00 (m, 1H), 3.84 (t, J=10.2 Hz, 1H), 3.35-3.23 (m, 4H), 2.83 (t, J=4.4 Hz, 4H). HR-MS (ESI): m/z [M+H]$^+$ calcd for $C_{17}H_{19}FN_5O_3S$: 392.1187; found: 392.1178.

Example 13

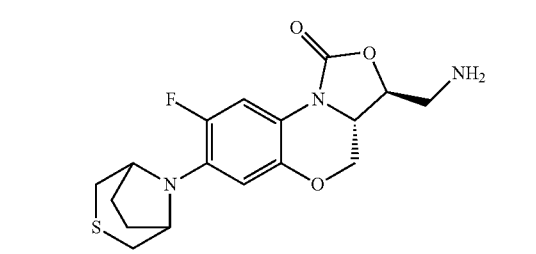 [SMILES: NC[C@@H]1OC(=O)N2c3cc(F)c(N4C5CCC4CSC5)cc3OC[C@@H]12]

(3S,3aS)-3-(Aminomethyl)-7-((1R,5S)-3-thia-8-azabicyclo[3.2.1]octan-8-yl)-8-fluoro-3a,4-dihydro-1H,3H-benzo[b]oxazolo[3,4-d][1,4]oxazin-1-one (compound 13)

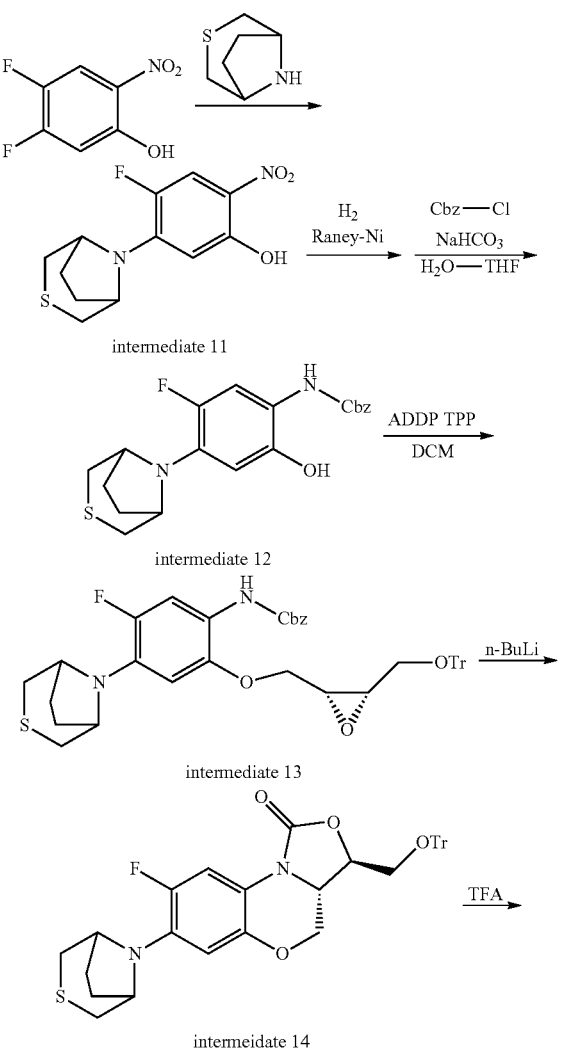

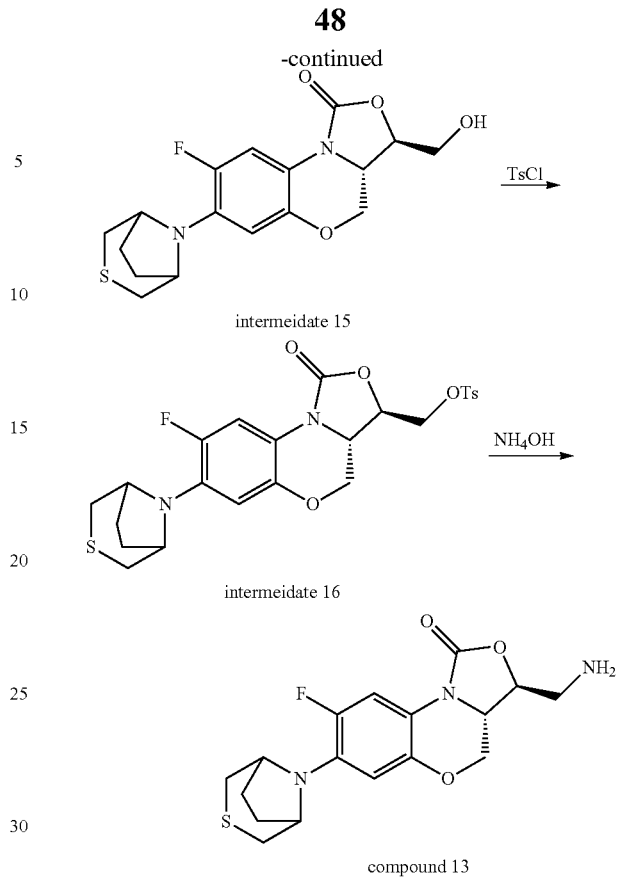

Step 1 Preparation of 5-((1R,5S)-3-thia-8-azabicyclo[3.2.1]octan-8-yl)-4-fluoro-2-nitrophenol (intermediate 11)

To a solution of 4,5-difluoro-2-nitrophenol (3.55 g, 20 mmol) in acetonitrile (40 mL) was added N-methylmorpholine (6.7 mL, 60 mmol), followed by (1R, 5S)-3-thia-8-azadicyclo [3.2.1]octane hydriodic acid (5.14 g, 20 mmol), which was reacted at 70° C. for 8 hrs before cooling. After adding water (30 mL), a solid was precipitated, filtered, washed with water, and dried under infrared lamp to obtain 4.3 g of an orange solid intermediate 11 with a yield of 75.7%.

$^1$H NMR (400 MHz, CDCl$_3$) δ: 11.05 (s, 1H), 7.74 (d, J=14.6 Hz, 1H), 6.29 (d, J=7.6 Hz, 1H), 4.72 (s, 2H), 3.28 (dd, J=13.2, 1.8 Hz, 2H), 2.20 (m, 6H).

Step 2 Preparation of benzyl (4-((1R,5S)-3-thia-8-azabicyclo[3.2.1]octan-8-yl)-5-fluoro-2-hydroxyphenyl)carbamate (intermediate 12)

Intermediate 11 (4 g, 14.1 mmol) was suspended in a mixture of ethanol and tetrahydrofuran (1:1, 40 mL). Raney nickel (1 g) was added and hydrogenated at medium pressure for 3 hours. The reaction mixture was added with tetrahydrofuran (20 mL) and filtered into a flask containing sodium bicarbonate (2.37 g, 28 mmol) and water (20 mL), protected by argon. Benzyl chloroformate (1.9 mL, 14.1 mmol) was added dropwise under ice bath, and stirred for 20 minutes with temperature unchanged. The solvent was evaporated, and water was added. The resulting mixture was extracted with ethyl acetate for twice. The combined organic phases were washed with brine, dried over anhydrous sodium sulfate, filtered and concentrated to give red solid. The residue was purified by silica gel column chromatography eluted with petroleum ether/ethyl acetate=7/3 to give intermediate 12 (4.16 g, 81.6%) as a purple solid.

Step 3 Preparation of benzyl (4-((1R,5S)-3-thia-8-azabicyclo[3.2.1]octan-8-yl)-5-fluoro-2-(((2R,3S)-3-((trityloxy)methyl)oxiran-2-yl)methoxy)phenyl)carbamate (intermediate 13)

To a 250 mL three-necked flask were added intermediate 12 (3.62 g, 10 mmol), intermediate 1 (4.5 g, 13 mmol), triphenylphosphine (5.2 g, 20 mmol) and anhydrous dichloromethane (100 mL), and then ADDP (5 g, 20 mmol) was added in two batches. After the reaction was complete by TLC monitoring, n-hexane was added for dilution, the mixture was filtered, and the filtrate was concentrated. The crude product was purified by silica gel column chromatography eluted with petroleum ether/dichloromethane/ethyl acetate=80/10/10 to give intermediate 13 (2.3 g, 33.3%) as an off-white foam solid.

$^1$H NMR (400 MHz, CDCl$_3$) δ: 7.84 (d, J=13.6 Hz, 1H), 7.47-7.19 (m, 20H), 7.07 (s, 1H), 6.34 (d, J=7.8 Hz, 1H), 5.18 (s, 2H), 4.27 (brs, 2H), 4.18 (d, J=11.8 Hz, 1H), 3.83-3.74 (m, 1H), 3.43 (dd, J=10.6, 5.4 Hz, 1H), 3.36-3.23 (m, 4H), 3.14 (dd, J=10.4, 4.8 Hz, 1H), 2.17-1.93 (m, 3H).

Step 4 Preparation of (3R,3aS)-7-((1R,5S)-3-thia-8-azabicyclo[3.2.1]octan-8-yl)-8-fluoro-3-((trityloxy)methyl)-3a,4-dihydro-1H,3H-benzo[b]oxazolo[3,4-d][1,4]oxazin-1-one (intermediate 14)

To a solution of intermediate 13 (2.1 g, 3 mmol) in anhydrous tetrahydrofuran (33 mL) under the protection of argon at −78° C. was added n-BuLi (1.6 M in n-hexane 2 mL, 3.3 mmol) dropwise. After addition, the resulting mixture was stirred for 1 h with temperature unchanged, then warmed to room temperature and stirred overnight. Saturated ammonium chloride (2 mL) was added to quench the reaction. The solvent was evaporated, and water was added while stirring. The mixture was stirred and filtered. The filter cake was washed with water until neutral, dried, and washed with n-hexane twice to give intermediate 14 (1.7 g, 94.4%) as a light purple solid.

$^1$H NMR (400 MHz, CDCl$_3$) δ: 7.70 (d, J=14.2 Hz, 1H), 7.47-7.41 (m, 6H), 7.36-7.23 (m, 9H), 6.40 (d, J=8.0 Hz, 1H), 4.38-4.31 (m, 3H), 4.27-4.20 (m, 1H), 4.01-3.93 (m, 1H), 3.81 (t, J=10.2 Hz, 1H), 3.48 (dd, J=4.8, 3.6 Hz, 2H), 3.38-3.28 (m, 2H), 2.21-1.99 (m, 6H).

Step 5 Preparation of (3R,3aS)-7-((1R,5S)-3-thia-8-azabicyclo[3.2.1]octan-8-yl)-8-fluoro-3-(hydroxymethyl)-3a,4-dihydro-1H,3H-benzo[b]oxazolo[3,4-d][1,4]oxazin-1-one (intermediate 15)

To a solution of intermediate 14 (1.64 g, 2.7 mmol) in dichloromethane (25 mL) in a 50 mL flask was added trifluoroacetic acid (2.5 mL, 32.4 mmol) under ice bath, and stirred overnight at room temperature. The reaction mixture was adjusted to weak alkalinity with a solution of 4 N sodium hydroxide, and extracted twice with dichloromethane. The combined organic phases were washed with brine, dried over anhydrous sodium sulfate, filtered and concentrated to give a solid. The solid was purified by silica gel (200-300 mesh) column chromatography (dichloromethane/methanol=98/2) to obtained intermediate 15 (0.83 g, 84.0%) as an off-white solid.

$^1$H NMR (400 MHz, CDCl$_3$) δ: 7.71 (d, J=14.2 Hz, 1H), 6.43 (d, J=8.0 Hz, 1H), 4.44 (dd, J=10.5, 3.0 Hz, 1H), 4.41-4.31 (m, 3H), 4.18-4.10 (m, 1H), 4.02 (dd, J=12.4, 3.8 Hz, 1H), 3.93-3.82 (m, 2H), 3.41-3.31 (m, 2H), 2.22-2.02 (m, 7H). LC-MS (ESI): m/z [M+H]$^+$: 367.1288.

Step 6 Preparation of ((3R,3aS)-7-((1R,5S)-3-thia-8-azabicyclo[3.2.1]octan-8-yl)-8-fluoro-1-oxo-3a,4-dihydro-1H,3H-benzo[b]oxazolo[3,4-d][1,4]oxazin-3-yl)methyl-4-methyl benzenesulfonate (intermediate 16)

To a solution of intermediate 15 (0.79 g, 2.16 mmol) and DMAP (80 mg) in dichloromethane (20 mL) in a 50 mL two-necked flask was added triethylamine (0.46 mL, 3.24 mmol). The resulting mixture was cooled to 0° C. with ice-water bath, and p-methylbenzenesulfonyl chloride (0.49 g, 2.59 mmol) was added in portions. The reaction mixture was stirred for 3 hrs with temperature unchanged and diluted with dichloromethane. The reaction was washed sequentially with water, 10% citric acid solution and saturated brine, dried over anhydrous sodium sulfate, filtered and concentrated to give intermediate 16 (1.07 g, 95.5%) as an off-white solid.

$^1$H NMR (400 MHz, CDCl$_3$) δ: 7.81 (dd, J=6.8, 1.6 Hz, 2H), 7.62 (d, J=14.0 Hz, 1H), 7.40 (dd, J=8.0, 0.4 Hz, 2H), 6.41 (d, J=7.8 Hz, 1H), 4.48-4.30 (m, 5H), 4.26 (dd, J=11.0, 5.8 Hz, 1H), 4.06-4.00 (m, 1H), 3.84 (t, J=10.2 Hz, 1H), 3.34 (t, J=11.4 Hz, 1H), 2.48 (s, 3H), 2.21-1.99 (m, 6H). LC-MS (ESI): m/z [M+H]$^+$: 521.1164.

Step 7 Preparation of (3S,3aS)-3-(aminomethyl)-7-((1R,5S)-3-thia-8-azabicyclo[3.2.1]octan-8-yl)-8-fluoro-3a,4-diydro-1H,3H-benzo[b]oxazolo[3,4-d][1,4]oxazin-1-one (compound 13)

To a solution of intermediate 16 (0.8 g, 1.54 mmol) in tetrahydrofuran (24 mL) in a sealed tube was added ammonium hydroxide (15 mL). The reaction mixture was heated at 100° C. for 7 hrs. After cooling, tetrahydrofuran was evaporated, the aqueous phase was extracted with dichloromethane for three times. The combined organic phases were washed with brine, dried over anhydrous sodium sulfate, filtered and concentrated to give a light yellow solid. The residue was purified by silica gel (200-300 mesh) column chromatography (dichloromethane/methanol/ammonium hydroxide=100/2/1) to give compound 13 (464 mg, 82.6%) as an off-white solid. Mp. 168-169° C.

$^1$H NMR (400 MHz, CDCl$_3$) δ: 7.70 (d, J=14.2 Hz, 1H), 6.41 (d, J=8.0 Hz, 1H), 4.43 (dd, J=10.4, 3.0 Hz, 1H), 4.39-4.31 (m, 2H), 4.29-4.22 (m, 1H), 4.07-3.99 (m, 1H), 3.87 (t, J=10.2 Hz, 1H), 3.38-3.28 (m, 2H), 3.19-3.04 (m, 2H), 2.23-2.00 (m, 6H), 1.39-1.22 (brs, 2H). HR-MS (ESI): m/z [M+H]$^+$ calcd for C$_{17}$H$_{21}$FN$_3$O$_3$S: 366.1282; found: 366.1265.

Example 14

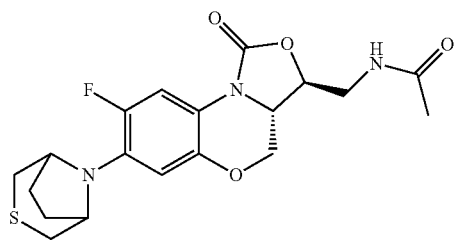 [SMILES: CC(=O)NC[C@@H]1OC(=O)N2c3cc(F)c(N4C5CCC4CSC5)cc3OC[C@@H]12]

51

N-(((3S,3aS)-7-((1R,5S)-3-thia-8-azabicyclo[3.2.1]octan-8-yl)-8-fluoro-1-oxo-3a,4-dihydro-1H,3H-benzo[b]oxazolo[3,4-d][1,4]oxazin-3-yl)methyl)acetamide (compound 14)

52

N-(((3S,3aS)-8-fluoro-1-oxo-7-thiomorpholyl-3a,4-dihydro-1H,3H-benzo[b]oxazolo[3,4-d][1,4]oxazin-3-yl)methyl)isobutyramide (compound 15)

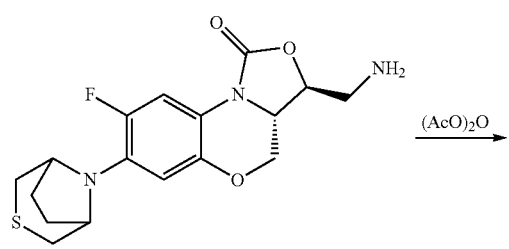

compound 13

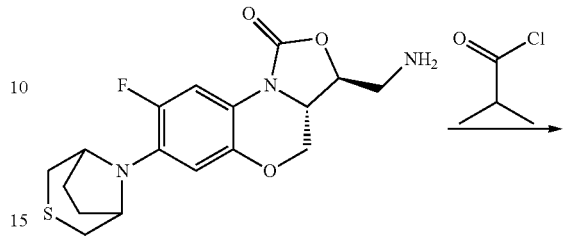

compound 13

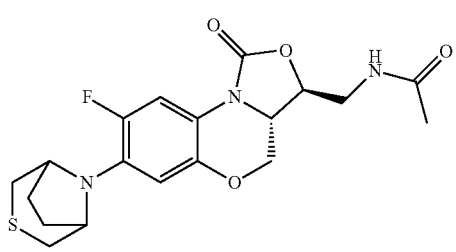

compound 14

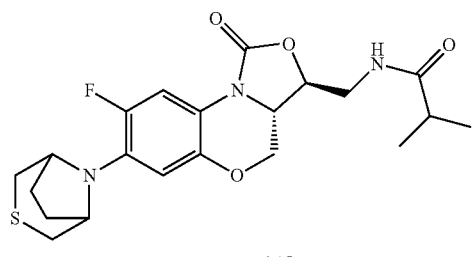

compound 15

To a solution of compound 13 (0.062 g, 0.17 mmol) in dichloromethane (4 mL) was added pyridine (0.042 mL, 0.52 mmol), cooled in ice bath. Acetic anhydride (0.024 mL, 0.26 mmol) was added and then the mixture was stirred for 1.5 hrs. The solvent was evaporated. The residue was purified by silica gel column chromatography (dichloromethane/methanol=98.5/1.5) to give compound 14 (43 mg, 62.3%) as an white solid. Mp: 235-236° C.

$^{1}$H NMR (400 MHz, CDCl$_3$) δ: 7.67 (d, J=14.2 Hz, 1H), 6.42 (d, J=8.0 Hz, 1H), 6.14 (t, J=6.0 Hz, 1H), 4.48 (dd, J=10.0, 2.6 Hz, 1H), 4.43-4.31 (m, 3H), 3.95-3.88 (m, 1H), 3.84 (t, J=10.0 Hz, 1H), 3.78-3.63 (m, 2H), 3.39-3.29 (m, 2H), 2.21-1.99 (s, 9H). HR-MS (ESI): m/z [M+H]$^{+}$ calcd for C$_{19}$H$_{23}$FN$_3$O$_4$S: 408.1388; found: 408.1368.

Example 15

To a solution of compound 13 (0.062 g, 0.17 mmol) in dichloromethane (6 mL) was added triethylamine (0.036 mL, 0.26 mmol), cooled in ice bath. Isobutyryl chloride (0.022 mL, 0.21 mmol) was added and then the mixture was stirred for 1 h. The solvent was evaporated. The residue was purified by silica gel column chromatography (dichloromethane/methanol=99.5/0.5) to give compound 15 (54 mg, 73.0%) as a white solid. Mp: 164-165° C.

$^{1}$H NMR (400 MHz, CDCl$_3$) δ: 7.65 (d, J=13.2 Hz, 1H), 6.41 (brs, 1H), 6.06 (t, J=6.0 Hz, 1H), 4.47 (dd, J=10.0, 2.6 Hz, 1H), 4.43-4.28 (m, 3H), 3.97-3.79 (m, 2H), 3.79-3.61 (m, 2H), 3.34 (t, J=11.4 Hz, 2H), 2.49-2.36 (m, 1H), 2.21-1.99 (m, 6H), 1.17 (d, J=2.8 Hz, 3H), 1.16 (d, J=2.4 Hz, 3H). HR-MS (ESI): m/z [M+H]$^{+}$ calcd for C$_{21}$H$_{27}$FN$_3$O$_4$S: 436.1701; found: 436.1680.

Example 16

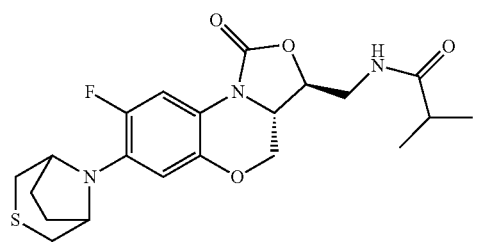 [SMILES: CC(C)C(=O)NC[C@@H]1OC(=O)N2c3cc(F)c(N4C5CCC4CSC5)cc3OC[C@@H]12]

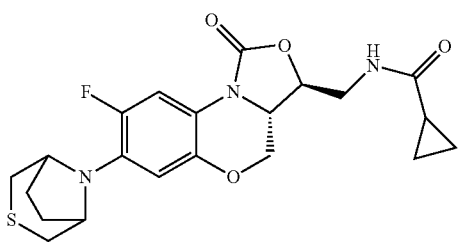 [SMILES: O=C(NC[C@@H]1OC(=O)N2c3cc(F)c(N4C5CCC4CSC5)cc3OC[C@@H]12)C1CC1]

53

N-(((3S,3aS)-7-((1R,5S)-3-thia-8-azabicyclo[3.2.1]
octan-8-yl)-8-fluoro-1-oxo-3a,4-dihydro-1H,3H-
benzo[b]oxazolo[3,4-d][1,4]oxazin-3-yl)methyl)
cyclopropanecarboxamide (compound 16)

54

N-(((3S,3aS)-7-((1R,5S)-3-thia-8-azabicyclo[3.2.1]
octan-8-yl)-8-fluoro-1-oxo-3a,4-dihydro-1H,3H-
benzo[b]oxazolo[3,4-d][1,4]oxazin-3-yl)methyl)
cyclobutanecarboxamide (compound 17)

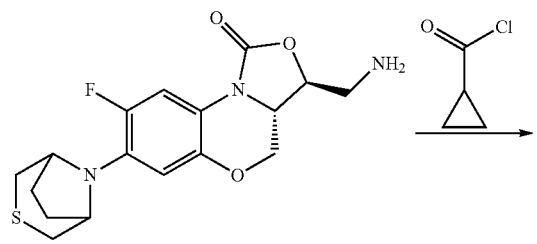

compound 13

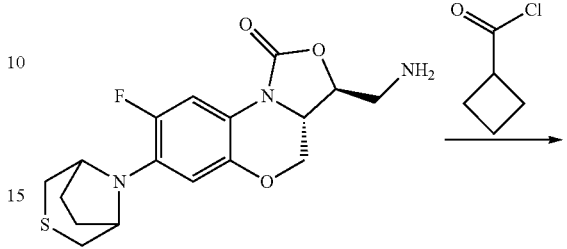

compound 13

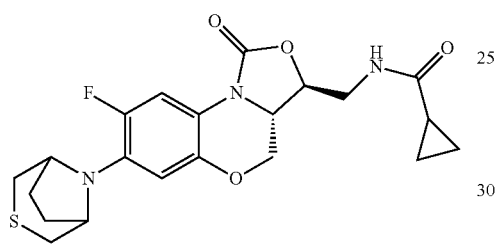

compound 16

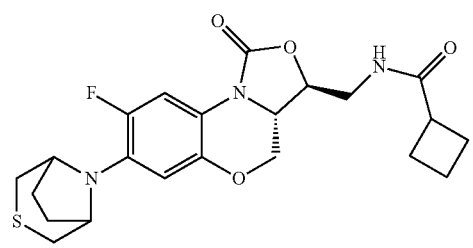

compound 17

To a solution of compound 13 (0.062 g, 0.17 mmol) in dichloromethane (6 mL) was added triethylamine (0.036 mL, 0.26 mmol), cooled in ice bath. Cyclopropanecarbonyl chloride (0.019 mL, 0.21 mmol) was added and then the mixture was stirred for 1 h. The solvent was evaporated. The residue was purified by silica gel column chromatography (dichloromethane/methanol=99.5/0.5) to obtain compound 16 (57 mg, 77.0%) as an off-white solid. Mp. 169-171° C.

$^1$H NMR (400 MHz, CDCl$_3$) δ: 7.69 (d, J=14.2 Hz, 1H), 6.41 (d, J=8.0 Hz, 1H), 6.23 (t, J=6.0 Hz, 1H), 4.46 (dd, J=10.0, 2.6 Hz, 1H), 4.43-4.28 (m, 3H), 3.96-3.63 (m, 4H), 3.39-3.25 (m, 2H), 2.23-1.95 (m, 6H), 1.47-1.35 (m, 1H), 1.02-0.92 (m, 2H), 0.84-0.74 (m, 2H). HR-MS (ESI): m/z [M+H]$^+$ calcd for C$_{21}$H$_{25}$FN$_3$O$_4$S: 434.1544; found: 434.1525.

To a solution of compound 13 (0.062 g, 0.17 mmol) in dichloromethane (6 mL) was added triethylamine (0.036 mL, 0.26 mmol), cooled in ice bath. Cyclobutanecarbonyl chloride (0.020 mL, 0.21 mmol) was added and then the mixture was stirred for 1 hour. The resulting mixture was concentrated under reduced pressure. The residue was purified by silica gel column chromatography (dichloromethane/methanol=99.5/0.5) to obtain compound 17 (65 mg, 85.5%) as a white solid. Mp. 195-196° C.

$^1$H NMR (400 MHz, CDCl$_3$) δ: 7.66 (d, J=14.0 Hz, 1H), 6.41 (d, J=7.6 Hz, 1H), 5.87 (t, J=6.2 Hz, 1H), 4.47 (dd, J=10.0, 2.6 Hz, 1H), 4.43-4.28 (m, 3H), 3.97-3.79 (m, 2H), 3.79-3.61 (m, 2H), 3.34 (t, J=11.0 Hz, 2H), 3.14-2.95 (m, 1H), 2.35-1.80 (m, 12H). HR-MS (ESI): m/z [M+H]$^+$ calcd for C$_{22}$H$_{27}$FN$_3$O$_4$S: 448.1701; found: 448.1683.

Example 17

Example 18

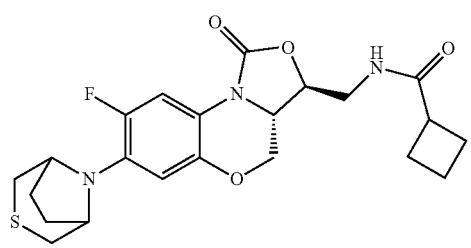 [SMILES: O=C(NC[C@@H]1OC(=O)N2c3cc(F)c(N4C5CCC4CSC5)cc3OC[C@@H]12)C1CCC1]

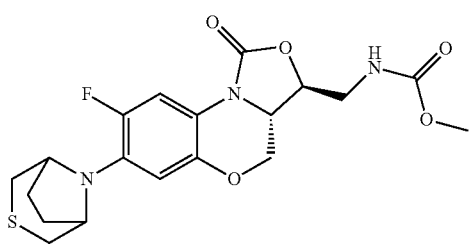 [SMILES: COC(=O)NC[C@@H]1OC(=O)N2c3cc(F)c(N4C5CCC4CSC5)cc3OC[C@@H]12]

55

Methyl (((3S,3aS)-7-((1R,5S)-3-thia-8-azabicyclo[3.2.1]octan-8-yl)-8-fluoro-1-oxo-3a,4-dihydro-1H,3H-benzo[b]oxazolo[3,4-d][1,4]oxazin-3-yl)methyl) carbamate (compound 18)

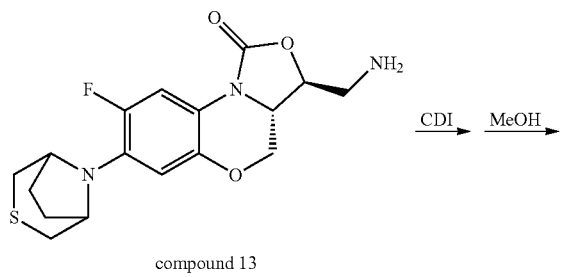

compound 13

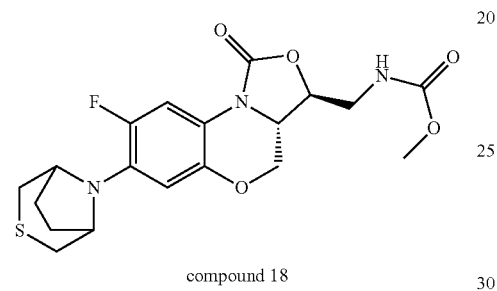

compound 18

To a solution of compound 13 (0.062 g, 0.17 mmol) in dichloromethane (4 mL) was added 1,1'-carbonyldiimidazole (CDI, 0.41 g, 2.55 mmol) and then the mixture was stirred at room temperature for 1 h. Anhydrous methanol (2 mL) was added and stirred overnight at room temperature. The mixture was added with water and dichloromethane. The resulting mixture was washed with saturated brine, dried over anhydrous sodium sulfate, filtered, and concentrated. The residue was purified by silica gel column chromatography (petroleum ether/ethyl acetate=50/50) to obtain compound 18 (25 mg, 34.7%) as an off-white solid. Mp. 149-151° C.

$^1$H NMR (400 MHz, CDCl$_3$) δ: 7.69 (d, J=14.0 Hz, 1H), 6.44 (d, J=7.4 Hz, 1H), 5.19 (s, 1H), 4.47 (dd, J=10.2, 2.6 Hz, 1H), 4.43-4.31 (m, 3H), 3.95 (brs, 1H), 3.85 (t, J=10.2 Hz, 1H), 3.71 (s, 3H), 3.67-3.56 (m, 2H), 4.43-3.32 (m, 2H), 2.22-2.00 (m, 6H). HR-MS (ESI): m/z [M+H]$^+$ calcd for C$_{19}$H$_{23}$FN$_3$O$_5$S: 424.1337; found: 424.1326.

Example 19

56

(3S,3aS)-7-((1R,5S)-3-thia-8-azabicyclo[3.2.1]octan-8-yl)-8-fluoro-3-((isoxazol-3-ylamino)methyl)-3a,4-dihydro-1H,3H-benzo[b]oxazolo[3,4-d][1,4]oxazin-1-one (compound 19)

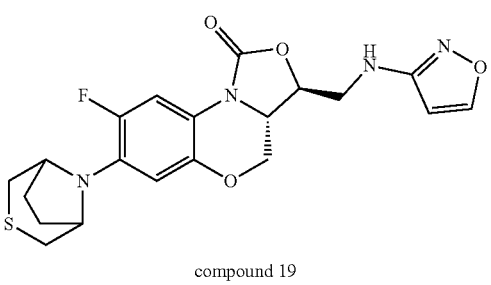

compound 16

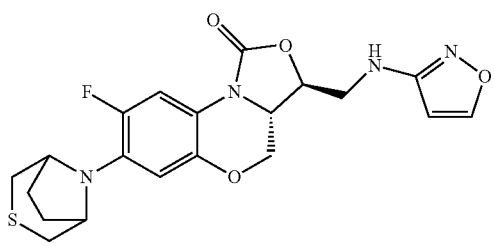 [SMILES: O=C1O[C@@H](CNc2ccon2)[C@@H]2COc3cc(N4C5CCC4CSC5)c(F)cc3N12]

compound 19

To a solution of N-Boc-3-aminoisoxazole (0.041 g, 0.22 mmol) in anhydrous DMF (2 mL) cooed with ice-water bath was added NaH (60%, 11 mg, 0.26 mmol). After stirring for 10 minutes, intermediate 16 (0.11 g, 0.22 mmol) was added and reacted at 70° C. for 1.5 hours. After cooling, water (10 mL) was added, and the mixture was extracted with ethyl acetate for twice. The combined organic phases were washed with brine, dried over anhydrous sodium sulfate, filtered and concentrated. The residue was purified by silica gel column chromatography (petroleum ether/ethyl acetate=85/15) to give a pale pink oil.

To a solution of the above oil in dichloromethane (2 mL) was added methanol solution of hydrogen chloride (5 N, 4 mL), stirred at room temperature overnight. The solvent was evaporated, water (3 mL) was added, and the pH was adjusted to alkalinity using saturated sodium bicarbonate. The solid was precipitated, and filtered. The filter cake was washed with water until neutral, dried to afford compound 19 (65 mg, 68.4% for two steps) as a pale pink solid. Mp. 180-182° C.

$^1$H NMR (400 MHz, CDCl$_3$) δ: 8.08 (s, 1H), 7.70 (d, J=14.0 Hz, 1H), 6.45 (d, J=7.8 Hz, 1H), 5.89 (s, 1H), 4.58 (brs, 1H), 4.53-4.46 (m, 1H), 4.42-4.31 (brs, 2H), 4.06-3.98 (m, 1H), 3.87 (t, J=10.0 Hz, 1H), 3.81-3.65 (m, 2H), 3.44-3.34 (m, 2H), 2.22-2.02 (m, 6H). HR-MS (ESI): m/z [M+H]$^+$ calcd for C$_{20}$H$_{22}$FN$_4$O$_4$S: 433.1340; found: 433.1321.

Example 20

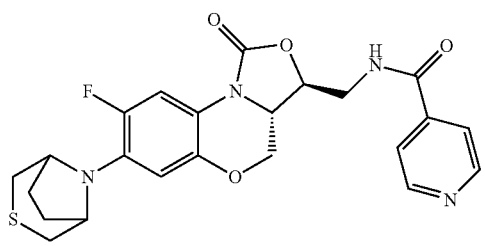 [SMILES: O=C(NC[C@@H]1OC(=O)N2c3cc(F)c(N4C5CCC4CSC5)cc3OC[C@@H]12)c1ccncc1]

N-(((3S,3aS)-7-((1R,5S)-3-thia-8-azabicyclo[3.2.1]
octan-8-yl)-8-fluoro-1-oxo-3a,4-dihydro-1H,3H-
benzo[b]oxazolo[3,4-d][1,4]oxazin-3-yl)methyl)
isonicotinamide (compound 20)

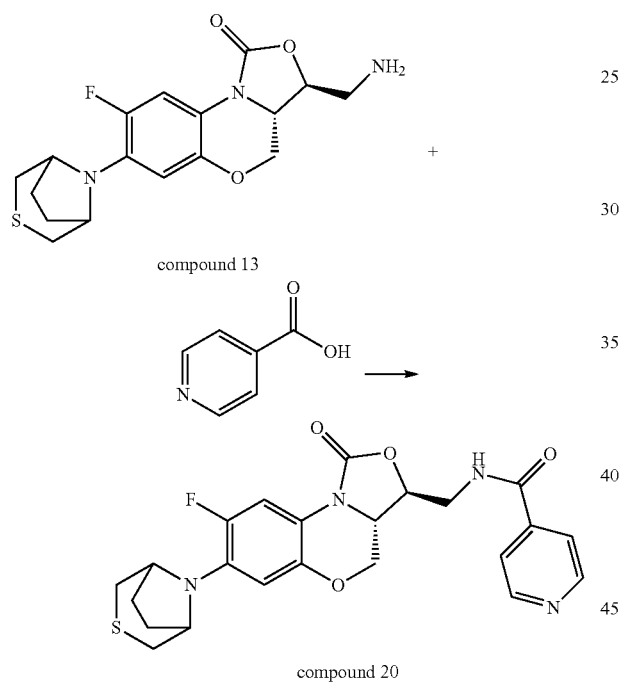

Compound 13 (62 mg, 0.17 mmol), isonicotinic acid (25 mg, 0.2 mmol), EDCI (38 mg, 0.2 mmol), HOBt (27 mg, 0.2 mmol) and triethylamine (0.072 mL, 0.51 mmol) were added to a 5 mL flask. DMF (2 mL) was added and stirred overnight at room temperature. A solid was precipitated by adding ice water and filtered. The obtained solid was dissolved in dichloromethane and purified by silica gel (200-300 mesh) column chromatography (dichloromethane/methanol/ammonium hydroxide=100/1.5/1) to obtain compound 20 (54 mg, 67.5%) as a white solid. Mp. 149-150° C.

$^1$H NMR (400 MHz, CDCl$_3$) δ: 8.78 (dd, J=4.4, 1.6 Hz, 2H), 7.68 (dd, J=4.4, 1.6 Hz, 2H), 7.63 (d, J=14.2 Hz, 1H), 7.17 (d, J=6.0 Hz, 1H), 6.41 (d, J=8.0 Hz, 1H), 4.58-4.48 (m, 2H), 4.35 (brs, 2H), 4.04-3.95 (m, 2H), 3.94-3.82 (m, 1H), 3.36-3.27 (m, 2H), 2.21-2.00 (m, 6H). HR-MS (ESI): m/z [M+H]$^+$ calcd for C$_{23}$H$_{24}$FN$_4$O$_4$S: 471.1497; found: 471.1479.

Example 21

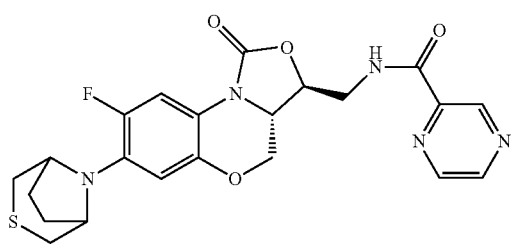 [SMILES: O=C(NC[C@@H]1OC(=O)N2c3cc(F)c(N4C5CCC4CSC5)cc3OC[C@@H]12)c1cnccn1]

N-(((3S,3aS)-7-((1R,5S)-3-Thia-8-azabicyclo[3.2.1]
octan-8-yl)-8-fluoro-1-oxo-3a,4-dihydro-1H,3H-
benzo[b]oxazolo[3,4-d][1,4]oxazin-3-yl)methyl)
pyrazine-2-carboxamide (compound 21)

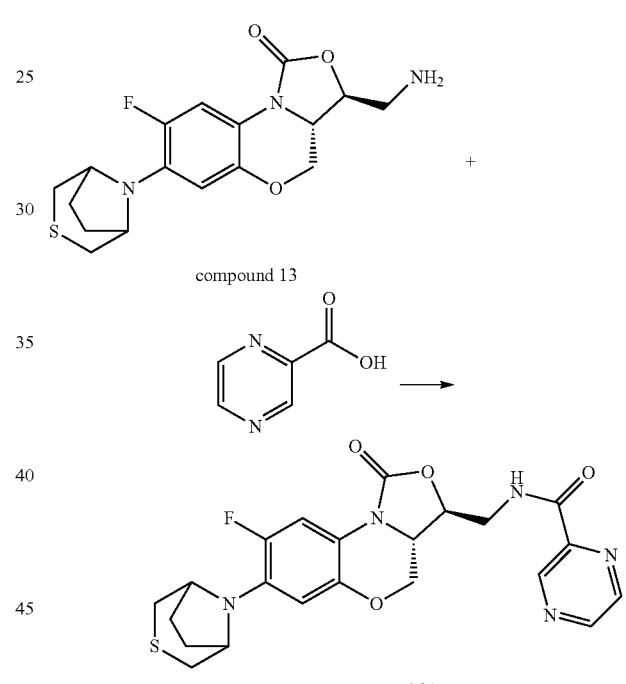

Compound 13 (62 mg, 0.17 mmol), 2-pyrazinecarboxylic acid (25 mg, 0.2 mmol), EDCI (38 mg, 0.2 mmol), HOBt (27 mg, 0.2 mmol) and triethylamine (0.072 mL, 0.51 mmol) were added to a 5 mL flask. DMF (2 mL) was added and then the mixture was stirred overnight at room temperature. A solid was precipitated by adding ice water, filtered and dissolved with dichloromethane, and then purified by silica gel (200-300 mesh) column chromatography (dichloromethane/methanol=99/1) to obtain compound 21 (64 mg, 80.0%) as a pale-yellow solid. Mp. >250° C.

$^1$H NMR (400 MHz, CDCl$_3$) δ: 9.39 (s, 1H), 8.80 (d, J=2.4 Hz, 1H), 8.58-8.55 (m, 1H), 8.28 (t, J=6.2 Hz, 1H), 7.67 (dd, J=4.4, 1.6 Hz, 1H), 6.41 (d, J=7.2 Hz, 1H), 4.56-4.46 (m, 2H), 4.34 (brs, 2H), 4.05-3.83 (m, 4H), 3.38-3.26 (m, 2H), 2.20-1.99 (m, 6H). HR-MS (ESI): m/z [M+H]$^+$ calcd for C$_{22}$H$_{23}$FN$_5$O$_4$S: 472.1449; found: 472.1430.

Example 22

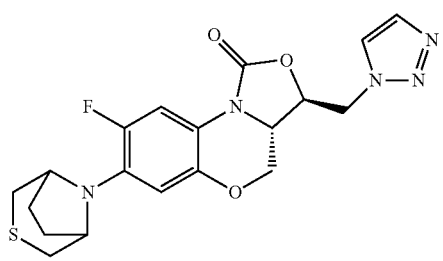 [SMILES: O=C1O[C@@H](Cn2ccnn2)[C@@H]2COc3cc(N4C5CCC4CSC5)c(F)cc3N12]

(3S,3aS)-3-((1H-1,2,3-Triazol-1-yl)methyl)-7-((1R, 5S)-3-thia-8-azabicyclo[3.2.1]octan-8-yl)-8-fluoro-3a,4-dihydro-1H,3H-benzo[b]oxazolo[3,4-d][1,4]oxazin-1-one (compound 22)

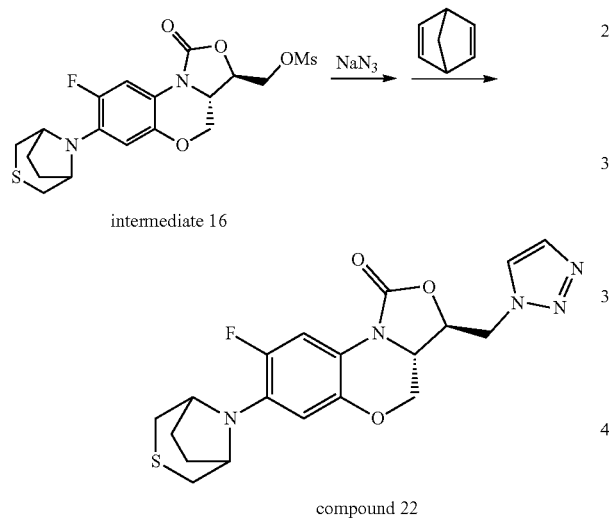

Intermediate 16 (135 mg, 0.26 mmol) was dissolved in DMF (5 mL). Sodium azide (34 mg, 0.4 mmol) was added to the solution. The reaction mixture was heated at 80° C. overnight and cooled to room temperature. After adding ice water (10 mL), a solid was precipitated, filtered, washed with water, and dried under infrared lamp to give an off-white solid (100 mg, 98.0%).

The obtained solid was dissolved in 1,4-dioxane (3 mL), and dicycloheptadiene (0.26 mL, 2.6 mmol) was added. The reaction mixture was refluxed overnight, and the solvent was evaporated. The resulting residue was purified by silica gel (200-300 mesh) column chromatography (dichloromethane/methanol=99/1) to give compound 22 (70 mg, 65.4%) as an off-white solid. Mp. 225-227° C.

$^1$H NMR (400 MHz, CDCl$_3$) δ: 7.79 (d, J=0.8 Hz, 1H), 7.78 (d, J=1.2 Hz, 1H), 7.58 (d, J=14.0 Hz, 1H), 6.39 (d, J=8.0 Hz, 1H), 4.86-4.81 (m, 2H), 4.72-4.66 (m, 1H), 4.44 (dd, J=10.4, 3.0 Hz, 1H), 4.39-4.30 (m, 2H), 4.07-3.99 (m, 1H), 3.86 (t, J=10.2 Hz, 1H), 3.37-3.26 (m, 2H), 2.20-2.00 (m, 6H). HR-MS (ESI): m/z [M+H]$^+$ calcd for C$_{19}$H$_{21}$FN$_5$O$_3$S: 418.1344; found: 418.1324.

Example 23

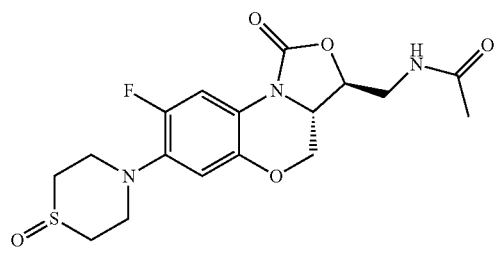 [SMILES: CC(=O)NC[C@@H]1OC(=O)N2c3cc(F)c(N4CCS(=O)CC4)cc3OC[C@@H]12]

N-(((3S,3aS)-8-Fluoro-1-oxo-7-(1-oxidothiomorpholino)-3a,4-dihydro-1H,3H-benzo[b]oxazolo[3,4-d][1,4]oxazin-3-yl)methyl)acetamide (compound 23)

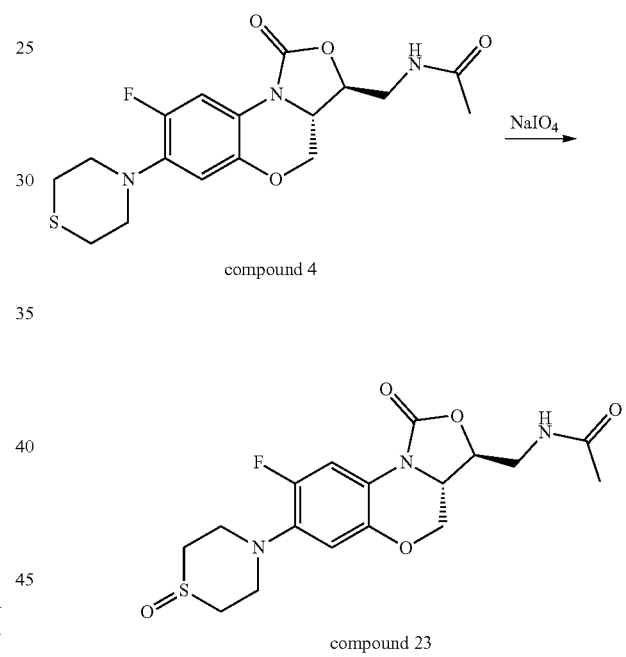

A mixture of compound 4 (0.1 g, 0.26 mmol) and sodium periodate (0.11 g, 0.52 mmol) was placed in a 25 mL single-necked flask. Methanol (4 mL) and water (1.5 mL) were added to the mixture and then the resulting mixture was stirred overnight at room temperature. The solvent was evaporated, and the residue was dissolved with methanol. The insoluble substance was filtered off and the filtrate was purified by silica gel column chromatography (ethyl acetate/methanol=96/4) to obtain compound 23 (74 mg, 71.8%) as a white solid. Mp. 214-216° C.

$^1$H NMR (400 MHz, CDCl$_3$) δ: 7.76 (d, J=12.8 Hz, 1H), 6.68 (d, J=7.8 Hz, 1H), 6.04 (t, J=6.0 Hz, 1H), 4.52 (dd, J=10.4, 3.0 Hz, 1H), 4.43-4.37 (m, 1H), 3.96-3.89 (m, 1H), 3.83 (t, J=10.2 Hz, 1H), 3.79-3.63 (m, 4H), 3.31-3.20 (m, 2H), 3.06-2.93 (m, 4H), 2.05 (s, 3H). HR-MS (ESI): m/z [M+H]$^+$ calcd for C$_{17}$H$_{21}$FN$_3$O$_5$S: 398.1180; found: 398.1162.

Example 24

N-(((3S,3aS)-8-Fluoro-1-oxo-7-(2-oxa-6-azaspiro[3.3]heptan-6-yl)-3a,4-dihydro-1H,3H-benzo[b]oxazolo[3,4-d][1,4]oxazin-3-yl)methyl)acetamide (compound 24)

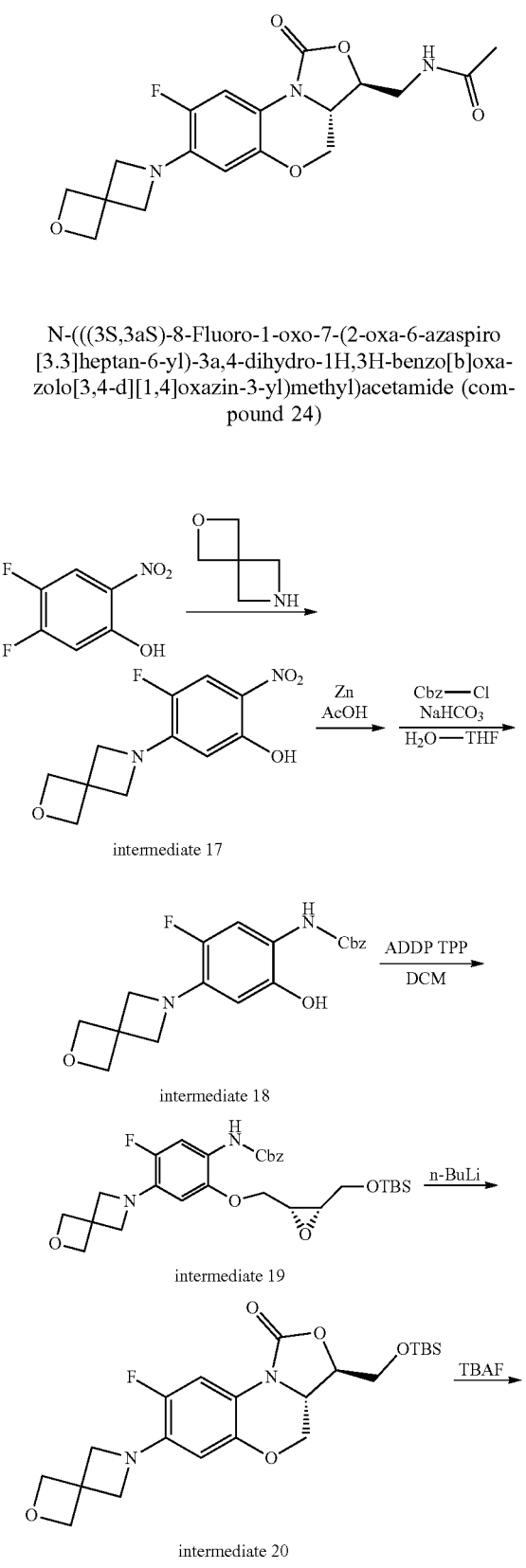

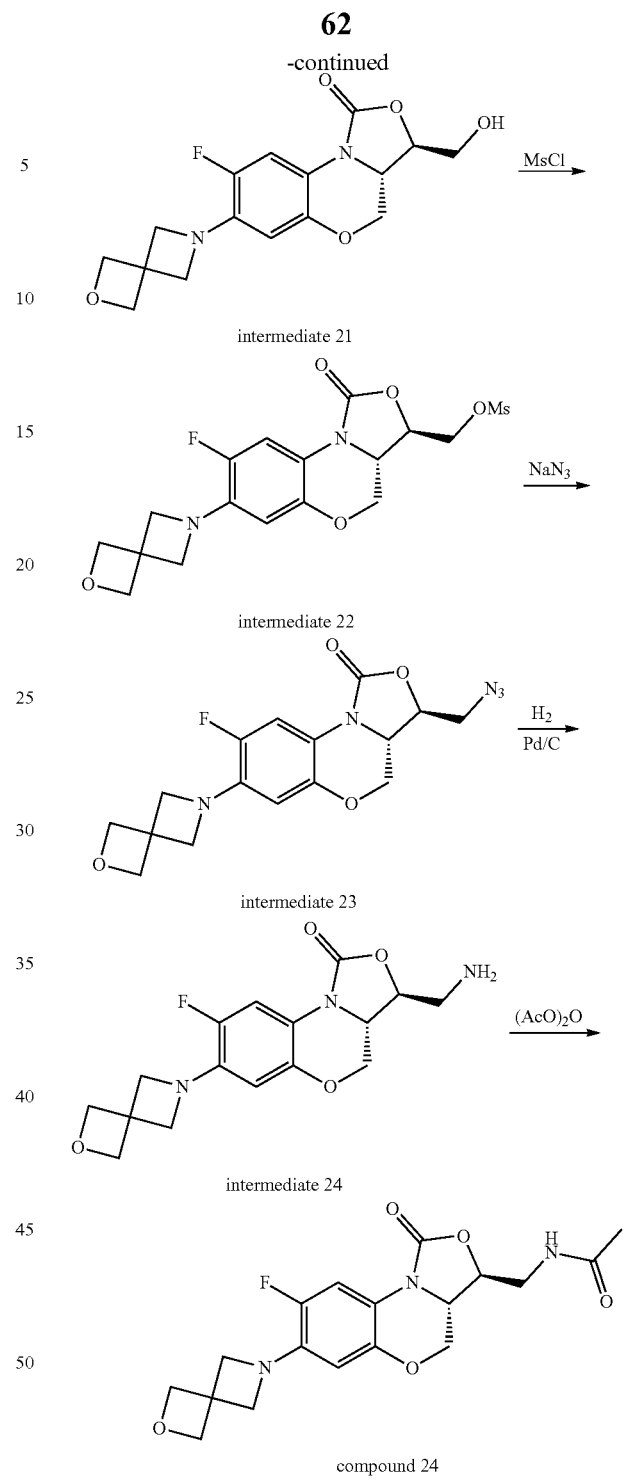

Step 1 Preparation of 4-fluoro-2-nitro-5-(2-oxa-6-azaspiro[3.3]heptan-6-yl)phenol (intermediate 17)

To a solution of 4,5-difluoro-2-nitrophenol (1.2 g, 6.9 mmol) in acetonitrile (5 mL) was added N-methylmorpholine (1.5 mL), followed by 2-oxa-6-azaspiro[3.3]heptane (1 g, 10 mmol), and they were reacted at 80° C. for 3 hrs before cooling. After adding water (20 mL), a solid was precipitated, filtered, washed with water, and dried under infrared lamp to give intermediate 17 (2.53 g, 77.7%) as a yellow solid.

Step 2 Preparation of benzyl (5-fluoro-2-hydroxy-4-(2-oxa-6-azaspiro[3.3]heptan-6-yl)phenyl)carbamate (intermediate 18)

To a suspension of intermediate 17 (3.8 g, 15 mmol) in tetrahydrofuran (80 mL) was added active Zn dust (3.9 g, 60 mmol) under the protection of argon. Acetic acid (4.3 mL, 75 mmol) was added dropwise and the temperature was maintained at 30-40° C. After the reaction was complete by TLC monitoring, the reaction solution was filtered into a flask containing sodium bicarbonate (3.8 g, 45 mmol) and water (40 mL) under the protection of argon. Benzyl chloroformate (2 mL, 15 mmol) was added under ice bath and stirred for 20 minutes with temperature unchanged. The solvent was evaporated, water was added, and the mixture was extracted with EtOAc for three times. The combined organic phases were washed with brine, dried over anhydrous sodium sulfate, filtered and concentrated to afford a red solid. The solid was purified by silica gel column chromatography (dichloromethane/ethyl acetate=80/20) to give intermediate 18 (1.5 g, 27.8%) as a red solid.

Step 3 Preparation of benzyl (2-(((2R,3S)-3-(((tert-butyldimethylsilyl)oxy)methyl)oxiran-2-yl)methoxy)-5-fluoro-4-(2-oxa-6-azaspiro[3.3]heptan-6-yl)phenyl)carbamate (intermediate 19)

To a 50 mL two-necked flask were added intermediate 18 (1 g, 2.8 mmol), intermediate 1 (0.8 g, 3.64 mmol), triphenylphosphine (1.47 g, 5.6 mmol) and anhydrous dichloromethane (20 mL), and then ADDP (1.4 g, 5.6 mmol) was added in two batches. After the reaction was complete by TLC monitoring, n-hexane was added for dilution, the reaction was filtered, and the filtrate was concentrated. The crude product was purified by silica gel column chromatography eluted with petroleum ether/ethyl acetate=80/20 to give intermediate 19 (0.7 g, 44.9%) as a pale-yellow oil which solidified at room temperature.
LC-MS (ESI): m/z [M+H]$^+$ 559.8687.

Step 4 Preparation of (3R,3aS)-3-(((tert-butyldimethylsilyl)oxy)methyl)-8-fluoro-7-(2-oxa-6-azaspiro[3.3]heptan-6-yl)-3a,4-dihydro-1H,3H-benzo[b]oxazolo[3,4-d][1,4]oxazin-1-one (intermediate 20)

To a solution of intermediate 19 (0.93 g, 1.67 mmol) in anhydrous tetrahydrofuran (18 mL) under the protection of argon at −78° C. was added n-BuLi (1.6 M in n-hexane 1.2 mL, 1.8 mmol) dropwise. After addition, the resulting mixture was stirred for 1 h with temperature unchanged, then warmed to room temperature and stirred overnight. Saturated ammonium chloride (2 mL) was added to quench the reaction. The solvent was evaporated, and ethyl acetate and water were added. The organic phase was separated and the aqueous phase was extracted with ethyl acetate again. The combined organic phases were washed with brine, dried over anhydrous sodium sulfate, filtered and concentrated. The residue was purified by silica gel column chromatography (petroleum ether/ethyl acetate=75/25) to give intermediate 20 (0.67 g, 89.2%) as a pale-yellow foam solid.
$^1$H NMR (400 MHz, CDCl$_3$) δ: 7.62 (dd, J=12.8, 0.4 Hz, 1H), 6.03 (d, J=8.2 Hz, 1H), 4.81 (s, 4H), 4.37 (dd, J=10.4, 3.2 Hz, 1H), 4.22 (m, 1H), 4.02 (m, 5H), 3.93-3.78 (m, 3H), 0.88 (s, 9H), 0.09 (2s, 6H). LC-MS (ESI): m/z [M+H]$^+$ 451.8929.

Step 5 Preparation of (3R,3aS)-8-fluoro-3-(hydroxymethyl)-7-(2-oxa-6-azaspiro[3.3]heptan-6-yl)-3a,4-dihydro-1H,3H-benzo[b]oxazolo[3,4-d][1,4]oxazin-1-one (intermediate 21)

To a solution of intermediate 20 (0.64 g, 1.4 mmol) in tetrahydrofuran (10 mL) under ice bath was added tetrabutylammonium fluoride (1.7 mL, 1.7 mmol, 1 M in tetrahydrofuran). After stirring for 0.5 hours, most solvent was evaporated and a solid was precipitated by adding water. The solid was filtered and the filter cake was washed with water, dried to afford intermediate 21 (0.41 g, 86.6%) as an off-white solid.

Step 6 Preparation of ((3R,3aS)-8-fluoro-1-oxo-7-(2-oxa-6-azaspiro[3.3]heptan-6-yl)-3a,4-dihydro-1H,3H-benzo[b]oxazolo[3,4-d][1,4]oxazin-3-yl)methyl-methanesulfonate (intermediate 22)

To a solution of intermediate 21 (0.4 g, 1.2 mmol) in dichloromethane (10 mL) cooled to 0° C. with ice-water bath was added N-methylmorpholine (0.26 mL, 2.4 mmol), and then methanesulfonyl chloride (0.11 mL, 1.4 mmol) was added. The reaction mixture was stirred for 5.5 hrs at room temperature, and concentrated to give a solid. The residue was added with water and filtered to give intermediate 22 (0.49 g, 99.4%) as a light yellow solid.
LC-MS (ESI): m/z [M+H]$^+$ 415.7708.

Step 7 Preparation of (3S,3aS)-3-(azidomethyl)-8-fluoro-7-(2-oxa-6-azaspiro[3.3]heptan-6-yl)-3a,4-dihydro-1H,3H-benzo[b]oxazolo[3,4-d][1,4]oxazin-1-one (intermediate 23)

To a solution of intermediate 22 (384 mg, 0.93 mmol) in DMF (10 mL) was added sodium azide (120 mg, 1.86 mmol). The reaction mixture was heated at 70° C. for 3 hours and cooled to room temperature. After adding ice water (10 mL), a solid was precipitated, filtered, washed with water, and dried to give intermediate 23 (285 mg, 84.8%) as an off-white solid.
LC-MS (ESI): m/z [M+H]$^+$ 362.7897.

Step 8 Preparation of N-(((3S,3aS)-8-fluoro-1-oxo-7-(2-oxa-6-azaspiro[3.3]heptan-6-yl)-3a,4-dihydro-1H,3H-benzo[b]oxazolo[3,4-d][1,4]oxazin-3-yl)methyl)acetamide (compound 24)

To a solution of intermediate 23 (70 mg, 0.19 mmol) in tetrahydrofuran (5 mL) was added Pd/C (10%, 10 mg). The reaction was carried out in hydrogen atmosphere for 2 hours. The reaction mixture containing intermediate 24 was filtered into a 25 mL flask. Pyridine (0.031 mL, 0.38 mmol) was added. After the reaction mixture was cooled in ice bath, acetic anhydride (0.029 mL, 0.3 mmol) was added dropwise and the resulting mixture was stirred overnight at room temperature. The mixture was diluted with dichloromethane. The organic phase was washed sequentially with 0.5 N aqueous hydrochloric acid and brine, dried over anhydrous sodium sulfate, filtered, concentrated. The residue was purified by silica gel column chromatography (dichloromethane/methanol=98/2) to give compound 24 (42 mg, 58.3%) as an off-white solid. Mp. 105-107° C.
$^1$H NMR (400 MHz, CDCl$_3$) δ: 7.63 (d, J=12.8 Hz, 1H), 6.05 (d, J=8.2 Hz, 1H), 5.96 (t, J=5.8 Hz, 1H), 4.82 (s, 4H), 4.50-4.43 (m, 1H), 4.39-4.33 (m, 1H), 4.06 (d, J=2.0 Hz, 4H), 3.92-3.77 (m, 2H), 3.76-3.61 (m, 2H), 2.04 (s, 3H). HR-MS (ESI): m/z [M+H]+ calcd for $C_{18}H_{21}FN_3O_5$: 378.1460; found: 378.1449.

Example 25

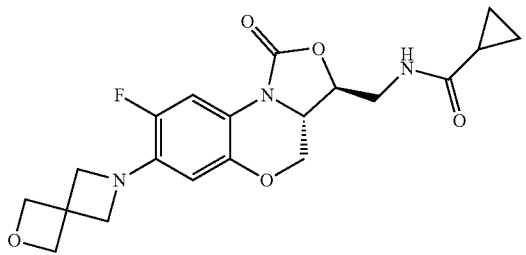 [SMILES: O=C(NC[C@@H]1OC(=O)N2c3cc(F)c(N4CC5(COC5)C4)cc3OC[C@@H]12)C1CC1]

N-(((3S,3aS)-8-Fluoro-1-oxo-7-(2-oxa-6-azaspiro [3.3]heptan-6-yl)-3a,4-dihydro-1H,3H-benzo[b]oxa-zolo[3,4-d][1,4]oxazin-3-yl)methyl)cyclopropan-ecarboxamide (compound 25)

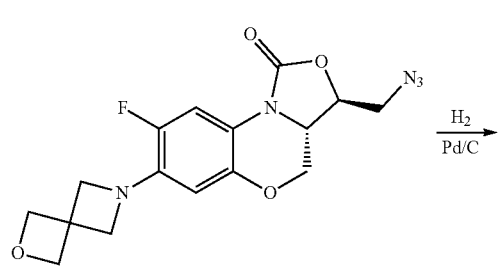

intermediate 23

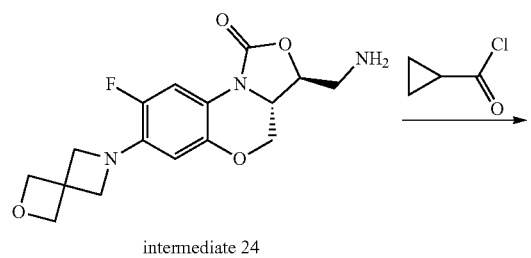

intermediate 24

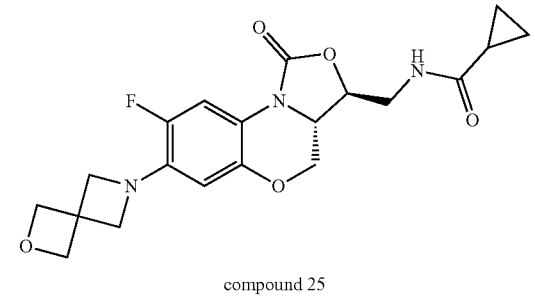

compound 25

To a solution of intermediate 23 (70 mg, 0.19 mmol) in tetrahydrofuran (5 mL) was added Pd/C (10%, 10 mg). The reaction was carried out in hydrogen atmosphere for 3 hours. The reaction mixture containing intermediate 24 was filtered into a 25 mL flask. Triethylamine (0.054 mL, 0.38 mmol) was added. After the reaction mixture was cooled in ice bath, cyclopropanecarbonyl chloride (0.025 mL, 0.27 mmol) was added dropwise, and the resulting mixture was stirred for 1 h at room temperature. The solvent was evaporated and the residue was purified by silica gel column chromatography (dichloromethane/methanol=99/1) to give compound 25 (45 mg, 58.4%) as an off-white solid. Mp. 181-183° C.

$^1$H NMR (400 MHz, CDCl$_3$) δ: 7.65 (d, J=12.8 Hz, 1H), 6.10 (t, J=6.0 Hz, 1H), 6.04 (d, J=8.2 Hz, 1H), 4.82 (s, 4H), 4.45 (dd, J=10.0, 2.8 Hz, 1H), 4.40-4.34 (m, 1H), 4.05 (d, J=2.0 Hz, 4H), 3.93-3.72 (m, 3H), 3.72-3.63 (m, 1H), 1.45-1.35 (m, 1H), 1.02-0.95 (m, 2H), 0.84-0.76 (m, 2H). HR-MS (ESI): m/z [M+H]+ calcd for $C_{20}H_{23}FN_3O_5$: 404.1616; found: 4040.1608.

Example 26

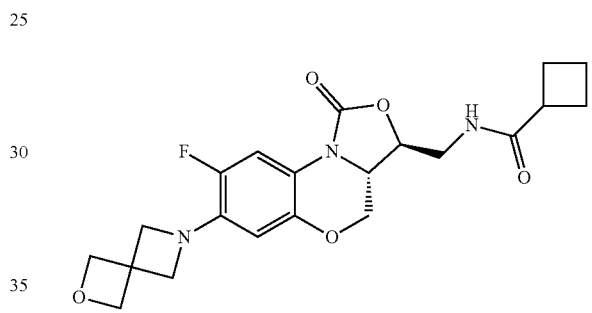

N-(((3S,3aS)-8-Fluoro-1-oxo-7-(2-oxa-6-azaspiro [3.3]heptan-6-yl)-3a,4-dihydro-1H,3H-benzo[b]oxa-zolo[3,4-d][1,4]oxazin-3-yl)methyl)cyclobutanecar-boxamide (compound 26)

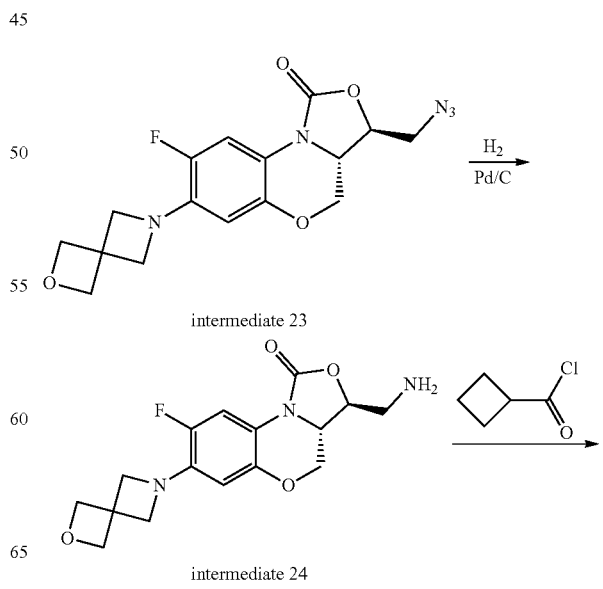

intermediate 23 intermediate 24

-continued

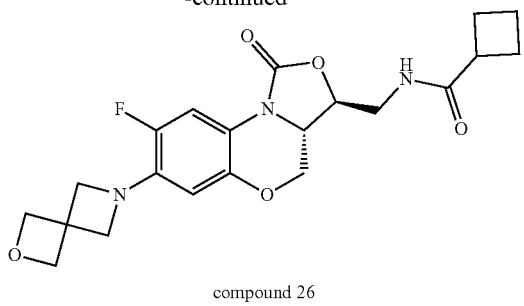

compound 26

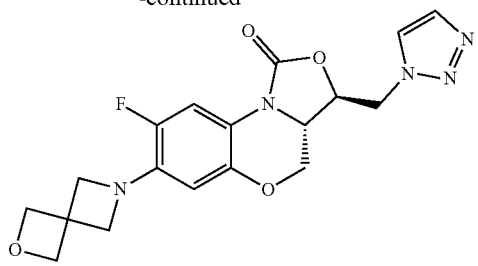

compound 27

To a solution of intermediate 23 (70 mg, 0.19 mmol) in tetrahydrofuran (5 mL) was added Pd/C (10%, 10 mg). The reaction was carried out in hydrogen atmosphere for 3 hours. The reaction mixture containing intermediate 24 was filtered into a 25 mL flask. Triethylamine (0.054 mL, 0.38 mmol) was added. After the reaction mixture was cooled in ice bath, cyclobutanecarbonyl chloride (0.026 mL, 0.27 mmol) was added dropwise, and the resulting mixture was stirred for 1 h at room temperature. The solvent was evaporated and the residue was purified by silica gel column chromatography (dichloromethane/methanol=99/1) to give compound 26 (44 mg, 55.7%) as an off-white solid. Mp. 118-120° C.
$^1$H NMR (400 MHz, CDCl$_3$) δ: 7.60 (d, J=12.8 Hz, 1H), 6.03 (d, J=8.2 Hz, 1H), 5.81 (t, J=6.2 Hz, 1H), 4.81 (s, 4H), 4.44 (dd, J=10.0, 2.6 Hz, 1H), 4.38-4.32 (m, 1H), 4.04 (d, J=2.0 Hz, 4H), 3.91-3.76 (m, 2H), 3.76-3.68 (m, 1H), 3.67-3.59 (m, 1H), 3.08-2.95 (m, 1H), 2.32-2.10 (m, 4H), 2.05-1.78 (m, 2H). HR-MS (ESI): m/z [M+H]$^+$ calcd for C$_{21}$H$_{25}$FN$_3$O$_5$: 418.1773; found: 418.1762.

Example 27

To a solution of intermediate 23 (70 mg, 0.19 mmol) in 1,4-dioxane (3 mL) was added dicycloheptadiene (0.19 mL, 1.9 mmol). The mixture was refluxed overnight. The solvent was evaporated and the residue was purified by silica gel (200-300 mesh) column chromatography (dichloromethane/methanol=98/2) to give compound 27 (42 mg, 56.8%) as an off-white solid. Mp. 219-221° C.
$^1$H NMR (400 MHz, CDCl$_3$) δ: 7.79-7.78 (d, J=0.8 Hz, 1H), 7.78-7.77 (d, J=0.8 Hz, 1H), 7.53 (d, J=12.8 Hz, 1H), 6.03 (d, J=8.2 Hz, 1H), 4.85-4.80 (m, 6H), 4.69-4.63 (m, 1H), 4.42 (dd, J=10.4, 3.0 Hz, 1H), 4.05 (d, J=2.0 Hz, 4H), 4.04-3.97 (m, 1H), 3.82 (t, J=10.2 Hz, 1H). HR-MS (ESI): m/z [M+H]$^+$ calcd for C$_{18}$H$_{19}$FN$_5$O$_4$: 388.1416; found: 388.1405.

Example 28

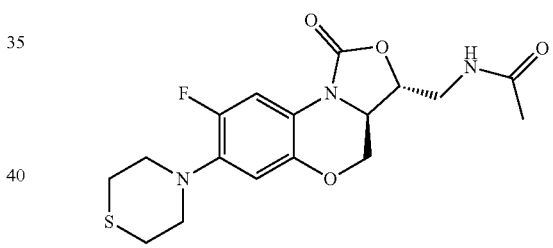

N-(((3R,3aR)-8-Fluoro-1-oxo-7-thiomorpholino-3a,4-dihydro-1H,3H-benzo[b]oxazolo[3,4-d][1,4]oxazin-3-yl)methyl)acetamide (compound 28)

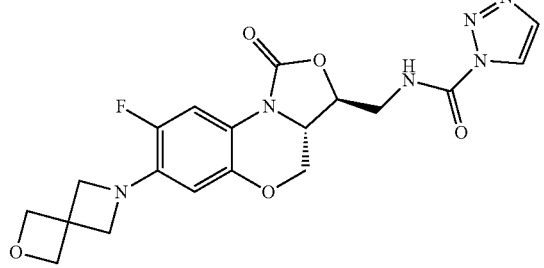

(3S,3aS)-3-((1H-1,2,3-Triazol-1-yl)methyl)-8-fluoro-7-(2-oxa-6-azaspiro[3.3]heptan-6-y 1)-3a,4-dihydro-1H,3H-benzo[b]oxazolo[3,4-d][1,4]oxazin-1-one (compound 27)

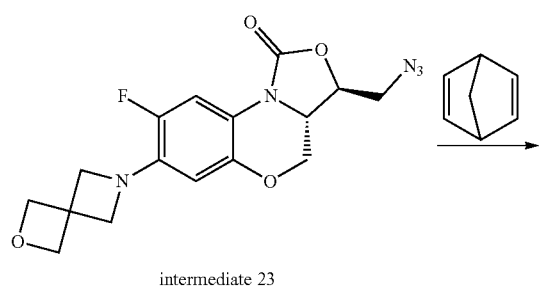

intermediate 23

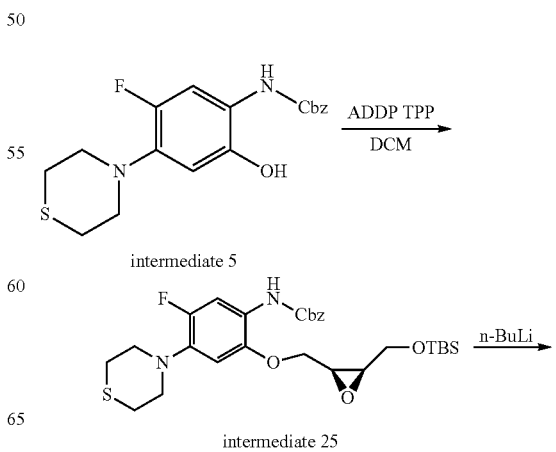

intermediate 5 intermediate 25

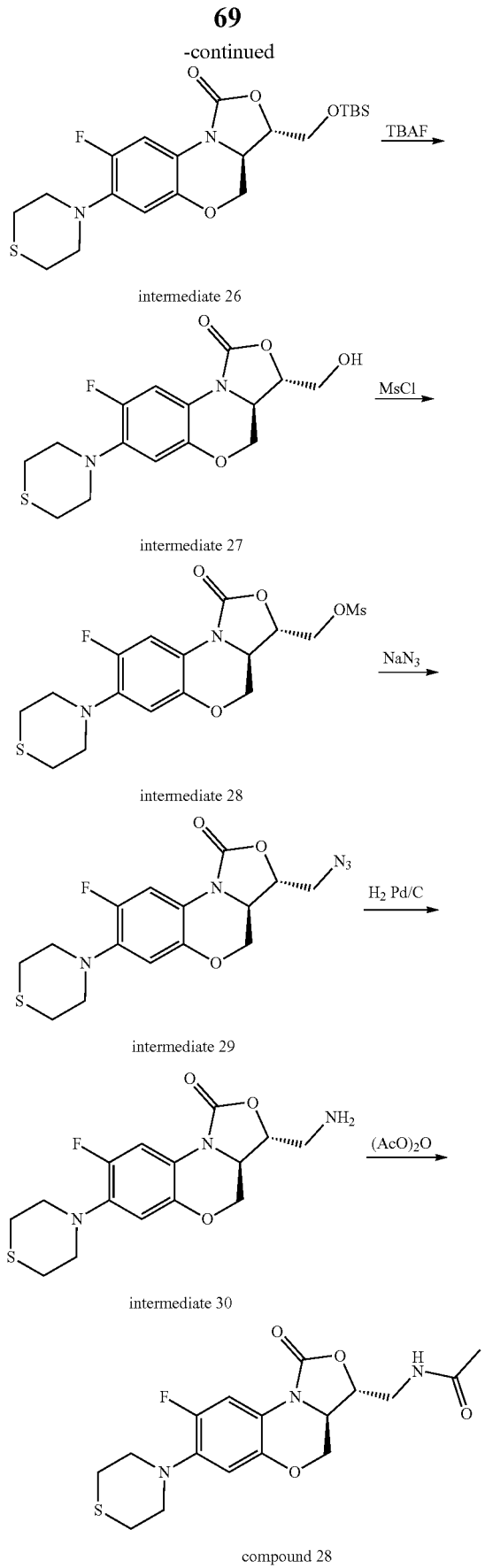

Step 1 Preparation of benzyl (2-(((2S,3R)-3-(((tert-butyldimethylsilyl)oxy)methyl)oxiran-2-yl)methoxy)-5-fluoro-4-thiomorpholinophenyl)carbamate (intermediate 25)

To a 50 mL two-necked flask were added intermediate 5 (1 g, 2.76 mmol), intermediate 2 (0.78 g, 3.59 mmol), triphenylphosphine (1.45 g, 5.52 mmol) and anhydrous dichloromethane (20 mL), and then ADDP (1.39 g, 5.52 mmol) was added in two batches. After the reaction was complete by TLC monitoring, n-hexane was added for dilution, the mixture was filtered, and the filtrate was concentrated. The crude product was purified by silica gel column chromatography eluted with petroleum ether/ethyl acetate=90/10 to give intermediate 25 (1.14 g, 73.5%) as an off-white solid.

$^1$H NMR (400 MHz, CDCl$_3$) δ: 7.93 (d, J=12.8 Hz, 1H), 7.44-7.31 (m, 5H), 7.20 (brs, 1H), 6.65 (brs, 1H), 5.20 (s, 2H), 4.32 (dd, J=11.4, 3.0 Hz, 1H), 4.05 (dd, J=11.4, 7.0 Hz, 1H), 3.91-3.79 (m, 2H), 3.40-3.20 (m, 6H), 2.83 (brs, 4H), 0.90 (s, 9H), 0.10 (s, 3H), 0.09 (s, 3H). LC-MS (ESI): m/z [M+H]$^+$ 563.8978.

Step 2 Preparation of (3S,3aR)-3-(((tert-butyldimethylsilyl)oxy)methyl)-8-fluoro-7-thiomorpholino-3a,4-dihydro-1H,3H-benzo[b]oxazolo[3,4-d][1,4]oxazin-1-one (intermediate 26)

To a solution of intermediate 25 (1.07 g, 1.9 mmol) in anhydrous tetrahydrofuran (20 mL) under the protection of argon at −78° C. was added n-BuLi (1.6 M in n-hexane 1.3 mL, 2.1 mmol) dropwise. After addition, the resulting mixture was stirred for 1.5 hrs with temperature unchanged, then warmed to room temperature and stirred overnight. Saturated ammonium chloride (2 mL) was added to quench the reaction. The solvent was evaporated, and ethyl acetate and water were added. The organic phase was separated, and the aqueous phase was extracted with ethyl acetate again. The combined organic phases were washed with brine, dried over anhydrous sodium sulfate, filtered, and concentrated in vacuum to give light purple solid. The residue was triturated with n-hexane and filtered to give intermediate 26 (0.79 g, 91.5%) as a light purple solid.

$^1$H NMR (400 MHz, CDCl$_3$) δ: 7.73 (d, J=13.0 Hz, 1H), 6.62 (d, J=6.6 Hz, 1H), 4.42 (dd, J=10.4, 3.2 Hz, 1H), 4.28-4.22 (m, 1H), 4.09-4.02 (m, 1H), 3.97-3.79 (m, 3H), 3.28 (m, 4H), 2.82 (t, J=4.8 Hz, 4H), 0.90 (s, 9H), 0.11 (s, 3H), 0.10 (s, 3H). LC-MS (ESI): m/z [M+H]$^+$ 455.9834.

Step 3 Preparation of (3S,3aR)-8-fluoro-3-(hydroxymethyl)-7-thiomorpholino-3a,4-dihydro-1H,3H-benzo[b]oxazolo[3,4-d][1,4]oxazin-1-one (intermediate 27)

To a solution of intermediate 26 (0.75 g, 1.65 mmol) in THF (10 mL) placed in ice-water bath was added tetrabutylammonium fluoride (2 mL, 2 mmol, 1 M in tetrahydrofuran). After stirring for 1 hour, the most solvent was evaporated, and a solid was precipitated by adding water. The solid was filtered and the filter cake was washed with water, dried to afford light purple solid, which was triturated with a mixture of n-hexane and diethyl ether (1:1) and filtered to give intermediate 27 (0.54 g, 95.7%) as an off-white solid.

Step 4 Preparation of ((3S,3aR)-8-fluoro-1-oxo-7-thiomorpholino-3a,4-dihydro-1H,3H-benzo[b]oxazolo[3,4-d][1,4]oxazin-3-yl)methylmethanesulfonate (intermediate 28)

To a suspension of intermediate 27 (0.52 g, 1.54 mmol) in dichloromethane (8 mL) was added N-methylmorpholine (0.34 mL, 3.08 mmol) and cooled to 0° C. with ice-water bath. Methanesulfonyl chloride (0.18 mL, 2.3 mmol) was added, the insoluble solid was dissolved gradually and then precipitated in the course of addition. After the reaction was complete by TLC monitoring, the solvent was evaporated to dryness to afford solid which was added with water and filtered to give intermediate 28 (0.63 g, 97.5%) as a light pink solid.

LC-MS (ESI): m/z [M+H]$^+$ 419.7741.

Step 5 Preparation of (3R,3aR)-3-(azidomethyl)-8-fluoro-7-thiomorpholino-3a,4-dihydro-1H,3H-benzo[b]oxazolo[3,4-d][1,4]oxazin-1-one (intermediate 29)

To a solution of intermediate 28 (490 mg, 1.17 mmol) in DMF (12 mL) was added sodium azide (152 mg, 2.34 mmol). The reaction mixture was heated at 80° C. for 3 hours and cooled to room temperature. Adding ice water (10 mL), a solid was precipitated, filtered, washed with water, and dried to give intermediate 29 (400 mg, 93.7%) as a light pink solid.

$^1$H NMR (400 MHz, CDCl$_3$) δ: 7.75 (dd, J=12.8, 1.8 Hz, 1H), 6.64 (d, J=7.0 Hz, 1H), 4.49-4.42 (m, 1H), 4.40-4.32 (m, 1H), 4.05-3.96 (m, 1H), 3.88-3.80 (m, 1H), 3.79-3.66 (m, 2H), 3.35-3.21 (m, 4H), 2.83 (brs, 4H).

Step 6 Preparation of N-(((3R,3aR)-8-fluoro-1-oxo-7-thiomorpholino-3a,4-dihydro-1H,3H-benzo[b]oxazolo[3,4-d][1,4]oxazin-3-yl)methyl)acetamide (compound 28)

To a solution of intermediate 29 (120 mg, 0.33 mmol) in tetrahydrofuran (6 mL) was added Pd/C (10%, 20 mg). The reaction was carried out in hydrogen atmosphere for 7 hours. The reaction mixture containing intermediate 29 was filtered into a 25 mL flask. Pyridine (0.053 mL, 0.66 mmol) was added. After the reaction mixture was cooled in ice bath, acetic anhydride (0.047 mL, 0.5 mmol) was added dropwise, and the resulting mixture was stirred for 1 h. The mixture was diluted with dichloromethane. The organic phase was washed with 0.5 N aqueous hydrochloric acid and brine, dried over anhydrous sodium sulfate, filtered, concentrated. The residue was purified by silica gel column chromatography (dichloromethane/methanol=98/2) to give compound 28 (86 mg, 68.2%) as an off-white solid. Mp. 210-212° C.

$^1$H NMR (400 MHz, CDCl$_3$) δ: 7.73 (d, J=13.0 Hz, 1H), 6.74 (brs, 1H), 6.27 (brs, 1H), 4.52 (dd, J=10.2, 2.8 Hz, 1H), 4.45-4.37 (m, 1H), 3.97-3.88 (m, 1H), 3.83 (t, J=10.2 Hz, 1H), 3.77-3.64 (m, 2H), 3.32 (brs, 4H), 2.86 (brs, 4H), 2.06 (s, 3H). HR-MS (ESI): m/z [M+H]$^+$ calcd for $C_{17}H_{21}FN_3O_4S$: 382.1231; found: 382.1224.

Example 29

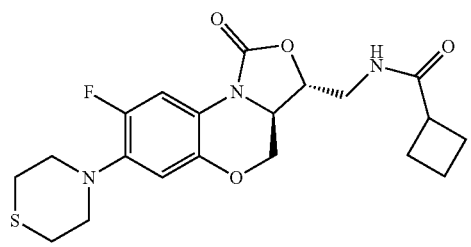 [SMILES: O=C(NC[C@H]1OC(=O)N2c3cc(F)c(N4CCSCC4)cc3OC[C@H]12)C1CCC1]

N-(((3R,3aR)-8-Fluoro-1-oxo-7-thiomorpholino-3a,4-dihydro-1H,3H-benzo[b]oxazolo[3,4-d][1,4]oxazin-3-yl)methyl)cyclobutane carboxamide (compound 29)

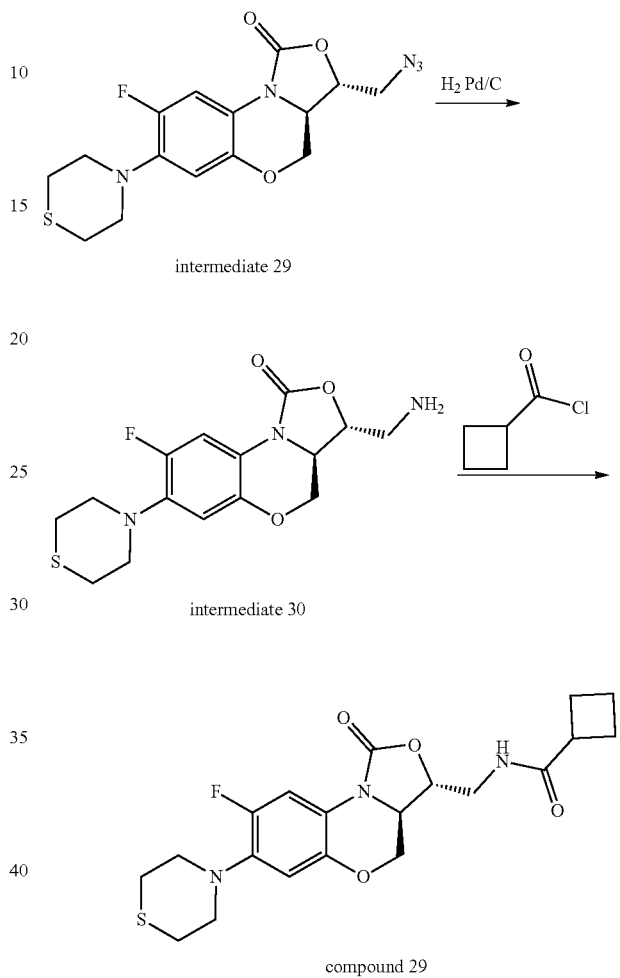

To a solution of intermediate 29 (120 mg, 0.33 mmol) in tetrahydrofuran (6 mL) was added Pd/C (10%, 20 mg). The reaction was carried out in hydrogen atmosphere for 7 hours. The reaction mixture containing intermediate 30 was filtered into a 25 mL flask. Pyridine (0.053 mL, 0.66 mmol) was added. After the reaction mixture was cooled in ice bath, cyclobutanecarbonyl chloride (0.042 mL, 0.43 mmol) was added dropwise, and the resulting mixture was stirred for 1 h at room temperature. The mixture was diluted with dichloromethane, and washed with water and saturated brine, dried over anhydrous sodium sulfate, filtered, concentrated. The residue was purified by silica gel column chromatography (dichloromethane/methanol=99/1) to obtain compound 29 (92 mg, 66.2%) as a white solid. Mp. 183-185° C.

$^1$H NMR (400 MHz, CDCl$_3$) δ: 7.71 (d, J=12.8 Hz, 1H), 6.65 (d, J=7.2 Hz, 1H), 5.86 (t, J=6.0 Hz, 1H), 4.50 (dd, J=10.2, 2.8 Hz, 1H), 4.42-4.35 (m, 1H), 3.95-3.87 (m, 1H), 3.82 (t, J=10.2 Hz, 1H), 3.79-3.62 (m, 2H), 3.37-3.23 (m, 4H), 3.11-2.98 (m, 1H), 2.89-2.77 (m, 4H), 2.34-2.11 (m, 4H), 2.06-1.81 (m, 2H). HR-MS (ESI): m/z [M+H]$^+$ calcd for $C_{20}H_{25}FN_3O_4S$: 422.1544; found: 422.1534.

Example 30

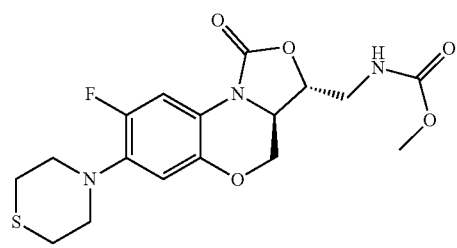 [SMILES: COC(=O)NC[C@H]1OC(=O)N2c3cc(F)c(N4CCSCC4)cc3OC[C@H]12]

Methyl (((3R,3aR)-8-fluoro-1-oxo-7-thiomor-
pholino-3a,4-dihydro-1H,3H-benzo[b]oxazolo[3,4-
d][1,4]oxazin-3-yl)methyl)carbamate (compound
30)

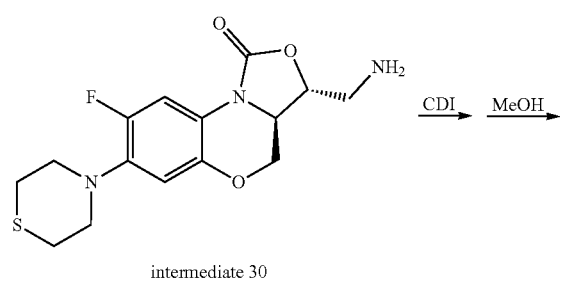

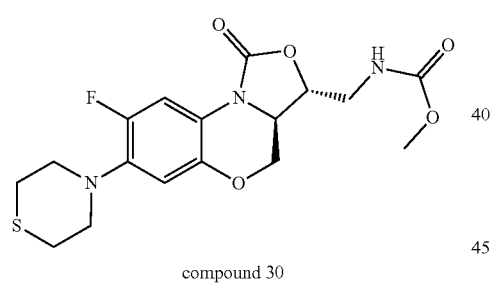

compound 30

To a solution of intermediate 30 (0.11 g, 0.33 mmol) in tetrahydrofuran (9 mL) was added 1,1'-carbonyldiimidazole (CDI, 0.80 g, 5 mmol) and stirred at room temperature for 50 mins. Anhydrous methanol (3 mL) was added and stirred overnight at room temperature. The solvent was evaporated and the mixture was diluted with dichloromethane. The resulting mixture was washed with saturated ammonium chloride and saturated brine, dried over anhydrous sodium sulfate, filtered, and concentrated to dryness. The residue was purified by silica gel column chromatography (petroleum ether/ethyl acetate=60/40) to obtain compound 30 (60 mg, 45.8%) as an off-white solid. Mp. 158-160° C.

$^1$H NMR (400 MHz, CDCl$_3$) δ: 7.74 (d, J=12.8 Hz, 1H), 6.66 (d, J=6.0 Hz, 1H), 5.12 (brs, 1H), 4.49 (dd, J=10.4, 3.0 Hz, 1H), 4.41-4.34 (m, 1H), 4.00-3.91 (m, 1H), 3.84 (t, J=10.2 Hz, 1H), 3.69 (s, 3H), 3.68-3.56 (m, 2H), 3.38-3.23 (m, 4H), 2.83 (t, J=4.8 Hz, 4H). HR-MS (ESI): m/z [M+H]$^+$ calcd for C$_{17}$H$_{21}$FN$_3$O$_5$S: 398.1180; found: 398.1176.

Example 31

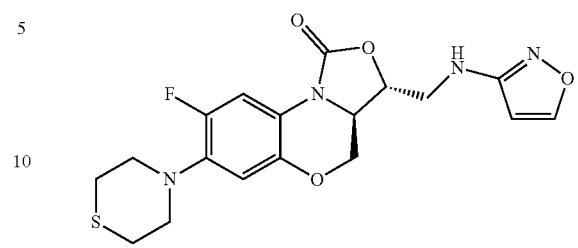

(3R,3aR)-8-Fluoro-3-((isoxazol-3-ylamino)methyl)-
7-thiomorpholino-3a,4-dihydro-1H, 3H-benzo[b]
oxazolo[3,4-d][1,4]oxazin-1-one (compound 31)

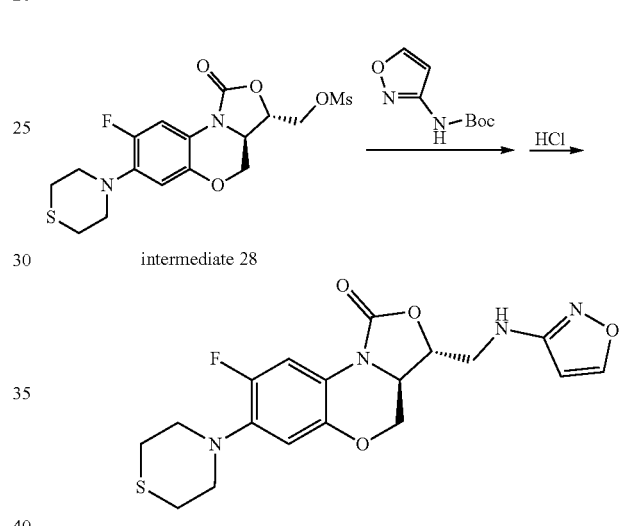

compound 31

To a solution of N-Boc-3-aminoisoxazole (0.048 g, 0.26 mmol) in anhydrous DMF (2 mL) cooled in ice-water bath was added NaH (60%, 12 mg, 0.29 mmol). After stirring for 10 minutes, intermediate 28 (0.13 g, 0.31 mmol) was added and reacted at 70° C. for 3 hours. After cooling, ice-water (10 mL) was added. The mixture was extracted with dichloromethane twice. The combined organic phases were washed with brine, dried over anhydrous sodium sulfate, filtered and concentrated. The residue was purified by silica gel column chromatography (petroleum ether/ethyl acetate=85/15) to give an oil (80 mg, 60.6%).

To a solution of the above obtained oil in ethyl acetate (2 mL) was added methanol solution of hydrogen chloride (5 N, 4 mL), stirred at room temperature for 30 minutes. The solvent was evaporated, water (3 mL) was added, and the pH was adjusted to alkalinity using saturated sodium bicarbonate. A solid was precipitated, and filtered. The filter cake was washed with water until neutral, dried to afford compound 31 (53 mg, 82.8%) as an off-white solid. Mp. 149-150° C.

$^1$H NMR (400 MHz, CDCl$_3$) δ: 8.10-8.06 (m, 1H), 7.76 (dd, J=12.8, 4.4 Hz, 1H), 6.69 (s, 1H), 5.95-5.80 (m, 1H), 4.67-4.43 (m, 2H), 4.34 (s, 1H), 4.01 (d, J=3.0 Hz, 1H), 3.94-3.61 (m, 3H), 3.31 (s, 4H), 2.84 (s, 4H). HR-MS (ESI): m/z [M+H]$^+$ calcd for C$_{18}$H$_{20}$FN$_4$O$_4$S: 407.1184; found: 407.1175.

Example 32

N-(((3S,3aS)-7-(4,4-Difluoropiperidin-1-yl)-8-fluoro-1-oxo-3a,4-dihydro-1H,3H-benzo[b]oxazolo[3,4-d][1,4]oxazin-3-yl)methyl)acetamide (compound 32)

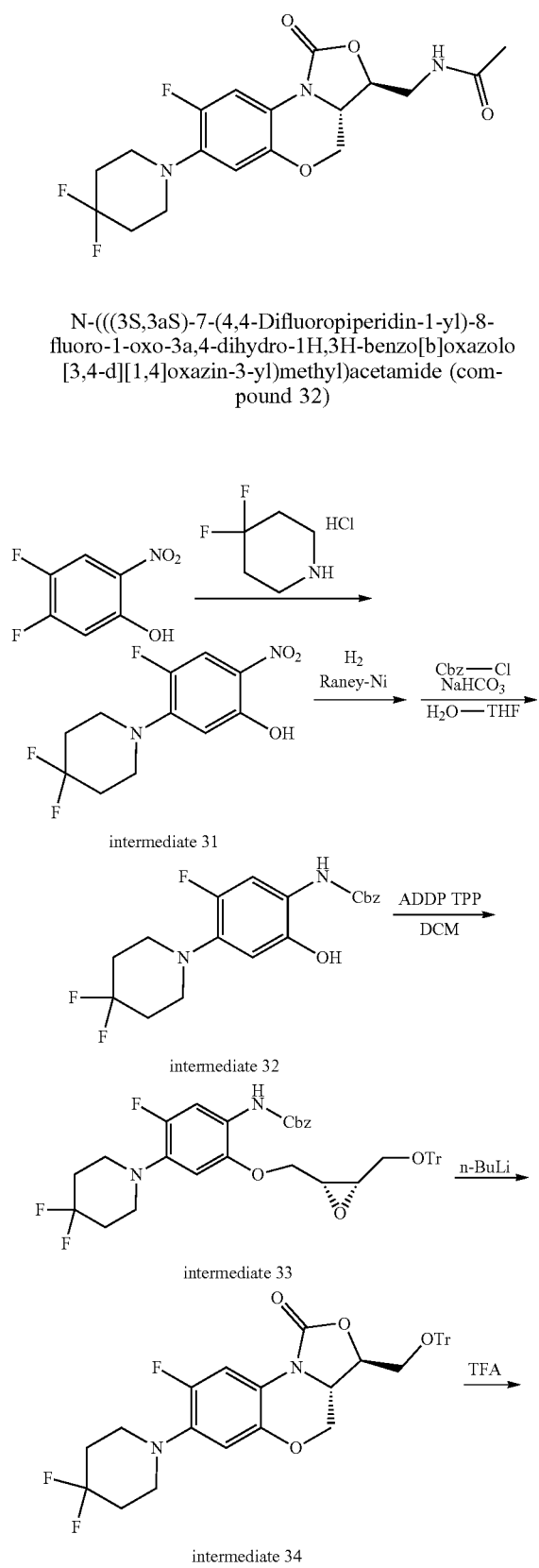

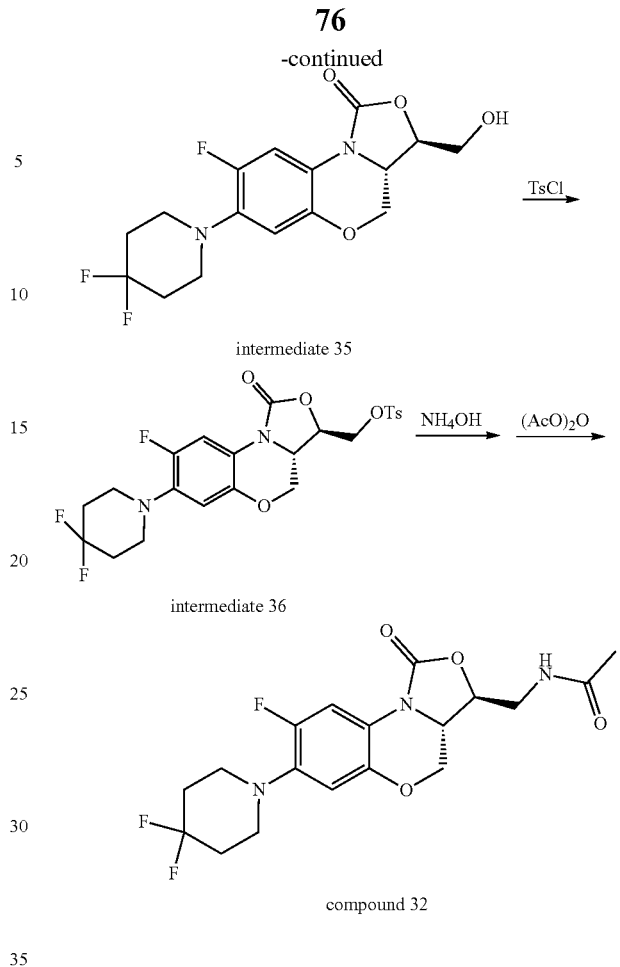

Step 1 Preparation of 5-(4,4-difluoropiperidin-1-yl)-4-fluoro-2-nitrophenol (intermediate 31)

To a solution of 4,5-difluoro-2-nitrophenol (2.8 g, 16 mmol) in acetonitrile (15 mL) was added N-methylmorpholine (4 mL) and 4,4-difluoropiperidine hydrochloride (3.5 g, 22 mmol). The reaction was carried out at 80° C. for 4 hours. After cooling, water was added (15 mL) and the reaction stood and layered overnight and then the reaction was filtered. The obtained solid was purified by silica gel column chromatography (petroleum ether/dichloromethane=80/20) to obtain intermediate 31 (3 g, 68.2%) as a yellow solid.

$^1$H NMR (400 MHz, CDCl$_3$) δ: 10.83 (s, 1H), 7.75 (d, J=13.2 Hz, 1H), 6.47 (d, J=7.7 Hz, 1H), 3.47 (t, J=5.6 Hz, 4H), 2.22-2.07 (m, 4H).

Step 2 Preparation of benzyl (4-(4,4-difluoropiperidin-1-yl)-5-fluoro-2-hydroxyphenyl)carbamate (intermediate 32)

To a solution of intermediate 31 (3 g, 10.87 mmol) in tetrahydrofuran (30 mL) was added Raney nickel (1 g). The reaction mixture was hydrogenated at medium pressure for 2 hours. The reaction mixture was filtered into a flask containing sodium bicarbonate (1.6 g, 19.2 mmol) and water (20 mL), protected by argon. Benzyl chloroformate (1.48 mL, 10.87 mmol) was added dropwise under ice bath, and stirred for 20 minutes with temperature unchanged. The solvent was evaporated, and water was added. The resulting mixture was extracted with ethyl acetate for twice. The combined organic phases were washed with brine, dried over anhydrous sodium sulfate, filtered and concentrated to give red solid. The residue was purified by silica gel column chromatography eluted with petroleum ether/ethyl acetate=80/20 to give intermediate 32 (4.7 g, 77.0%) as a light pink solid.

$^1$H NMR (400 MHz, CDCl$_3$) δ: 7.49-7.30 (m, 5H), 7.01 (brs, 1H), 6.87-6.55 (m, 2H), 5.22 (s, 2H), 3.18 (brs, 4H), 2.17 (s, 4H). LC-MS (ESI): m/z[M+H]$^+$: 381.2007.

Step 3 Preparation of benzyl (4-(4,4-difluoropiperidin-1-yl)-5-fluoro-2-(((2R,3S)-3-((trityloxy)methyl)oxiran-2-yl)methoxy)phenyl)carbamate (intermediate 33)

To a 100 mL three-necked flask were added intermediate 32 (1.6 g, 4.2 mmol), intermediate 3 (1.87 g, 5.4 mmol), triphenylphosphine (2.2 g, 8.4 mmol) and anhydrous dichloromethane (30 mL), and then ADDP (2.1 g, 8.4 mmol) was added in three batches. After the reaction was complete by TLC monitoring, n-hexane was added for dilution, the mixture was filtered, and the filtrate was concentrated. The crude product was purified by silica gel column chromatography eluted with petroleum ether/dichloromethane/ethyl acetate=80/10/10 to give intermediate 33 (2.2 g, 76.3%) as a pale-yellow oil.

Step 4 Preparation of (3R,3aS)-7-(4,4-difluoropiperidin-1-yl)-8-fluoro-3-((trityloxy)methyl)-3a,4-dihydro-1H,3H-benzo[b]oxazolo[3,4-d][1,4]oxazin-1-one (intermediate 34)

To a solution of intermediate 33 (4.5 g, 6.36 mmol) in anhydrous tetrahydrofuran (65 mL) under the protection of argon at −78° C. was added n-BuLi (1.6 M in n-hexane 4.7 mL, 7.63 mmol) dropwise. After addition, the resulting mixture was stirred for 1.5 hrs with temperature unchanged, then warmed to room temperature and stirred overnight. Saturated ammonium chloride (2 mL) was added to quench the reaction. The solvent was evaporated, and dichloromethane and water were added. The organic phase was separated and the aqueous phase was extracted with dichloromethane once again. The combined organic phases were washed with brine, dried over anhydrous sodium sulfate, filtered and concentrated. The residue was purified by silica gel column chromatography eluted with petroleum ether/dichloromethane/ethyl acetate=80/10/10 to give intermediate 34 (2.97 g, 77.7%) as a light pink solid.

Step 5 Preparation of (3R,3aS)-7-(4,4-difluoropiperidin-1-yl)-8-fluoro-3-(hydroxymethyl)-3a,4-dihydro-1H,3H-benzo[b]oxazolo[3,4-d][1,4]oxazin-1-one (intermediate 35)

To a solution of intermediate 34 (2.9 g, 4.83 mmol) in dichloromethane (50 mL) was added trifluoroacetic acid (5 mL) under ice bath, and stirred overnight at room temperature. The reaction mixture was adjusted to alkalinity with a solution of sodium bicarbonate, and extracted with dichloromethane for three times. The combined organic phases were washed with brine, dried over anhydrous sodium sulfate, filtered and concentrated. The residue was purified by silica gel column chromatography (dichloromethane/methanol=98/2) to obtain intermediate 35 (1.5 g, 88.2%) as an off-white solid.

$^1$H NMR (400 MHz, CDCl$_3$) δ: 7.78 (d, J=13.0 Hz, 1H), 6.75 (d, J=7.6 Hz, 1H), 4.47 (dd, J=10.6, 3.2 Hz, 1H), 4.37-4.33 (m, 1H), 4.18-4.11 (m, 1H), 4.03 (dd, J=12.4, 3.8 Hz, 1H), 3.92-3.83 (m, 2H), 3.28-3.13 (m, 4H), 2.28-2.14 (m, 4H).

Step 6 Preparation of N-(((3S,3aS)-7-(4,4-difluoropiperidin-1-yl)-8-fluoro-1-oxo-3a,4-dihydro-1H,3H-benzo[b]oxazolo[3,4-d][1,4]oxazin-3-yl)methyl)acetamide (compound 32)

A solution of intermediate 35 (0.4 g, 1.12 mmol) in dichloromethane (15 mL) was cooled to 0° C. with ice-water bath. Triethylamine (0.24 mL, 1.68 mmol) was added and then p-methylbenzenesulfonyl chloride (0.26 g, 1.34 mmol) was added in portions. The reaction mixture was stirred at room temperature for 4 hrs. The mixture was washed sequentially with water and saturated brine, dried over anhydrous sodium sulfate, filtered and concentrated to give intermediate 36 as a foam solid, which was directly used in next step without further purification.

The above obtained solid was dissolved in tetrahydrofuran (8 mL) and added with ammonium hydroxide (6 mL). The reaction mixture was heated in a sealed tube for 5 hours at 100° C. and then cooled. Tetrahydrofuran was evaporated and water was added. The mixture was extracted with ethyl acetate for three times. The combined organic phases were washed with saturated brine, dried over anhydrous sodium sulfate, filtered and concentrated to give a solid (330 mg, 82.5% yield in two steps).

To a suspension of the above solid (112 mg, 0.31 mmol) in dichloromethane (5 mL), was added pyridine (0.050 mL, 0.62 mmol), followed by acetic anhydride (0.039 mL, 0.41 mmol). The mixture was stirred for 1 h at room temperature and diluted with dichloromethane. The mixture was washed with water, 0.5 N aqueous hydrochloric acid and saturated brine, dried over anhydrous sodium sulfate, filtered and concentrated. The residue was purified by silica gel column chromatography (dichloromethane/methanol=98.5/1.5) to give compound 32 (95 mg, 76.6%) as a pale yellow solid. Mp. 230-232° C.

$^1$H NMR (400 MHz, CDCl$_3$) δ: 7.74 (d, J=13.0 Hz, 1H), 6.63 (d, J=7.8 Hz, 1H), 6.03 (t, J=6.2 Hz, 1H), 4.51 (dd, J=10.2, 2.8 Hz, 1H), 4.43-4.36 (m, 1H), 3.95-3.88 (m, 1H), 3.83 (t, J=10.2 Hz, 1H), 3.78-3.63 (m, 2H), 3.23-3.09 (m, 4H), 2.23-2.10 (m, 4H), 2.05 (s, 3H). HR-MS (ESI): m/z [M+H]$^+$ calcd for C$_{18}$H$_{21}$F$_3$N$_3$O$_4$: 400.1479; found: 400.1458.

Example 33

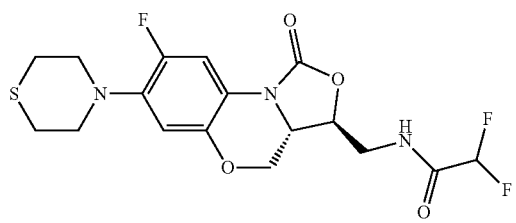 [SMILES: O=C(NC[C@@H]1OC(=O)N2c3cc(F)c(N4CCSCC4)cc3OC[C@@H]12)C(F)F]

2,2-Difluoro-N-(((3S,3aS)-8-fluoro-1-oxo-7-thiomorpholino-3a,4-dihydro-1H,3H-benzo [b]oxazolo[3,4-d][1,4]oxazin-3-yl)methyl)acetamide (compound 33)

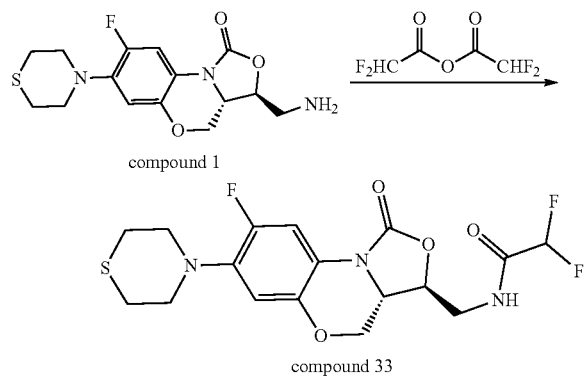

To a solution of compound 1 (174 mg, 0.52 mmol) in dichloromethane (8 mL) was added pyridine (0.084 mL, 1.04 mmol). After cooling with ice bath, difluoroacetic anhydride (0.070 mL, 0.56 mmol) was added dropwise, and then the mixture was stirred at room temperature for 40 minutes. The resulting mixture was concentrated. The residue was purified by silica gel column chromatography (dichloromethane/methanol=99/1) to obtain compound 33 (181 mg, 83.4%) as an off-white solid. Mp. 200-202° C.

$^1$H NMR (400 MHz, CDCl$_3$) δ: 7.71 (d, J=12.8 Hz, 1H), 6.92 (brs, 1H), 6.65 (s, 1H), 5.95 (t, J=54.0 Hz, 1H), 4.51 (dd, J=10.0, 2.4 Hz, 1H), 4.47-4.40 (m, 1H), 3.95-3.81 (m, 3H), 3.77-3.68 (m, 1H), 3.36-3.23 (m, 4H), 2.89-2.73 (m, 4H). HR-MS (ESI): m/z [M+H]$^+$ calcd for C$_{17}$H$_{19}$F$_3$N$_3$O$_4$S: 418.1043; found: 418.1039.

Example 34

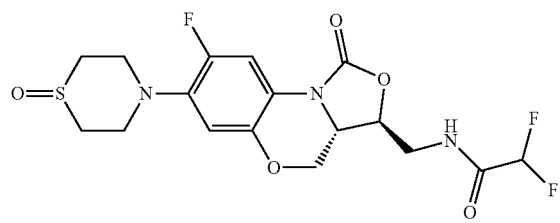 [SMILES: O=C(NC[C@@H]1OC(=O)N2c3cc(F)c(N4CCS(=O)CC4)cc3OC[C@@H]12)C(F)F]

2,2-Difluoro-N-(((3S,3aS)-8-fluoro-7-(1-oxidothiomorpholino)-1-oxo-3a,4-dihydro-1H, 3H-benzo[b]oxazolo[3,4-d][1,4]oxazin-3-yl)methyl)acetamide (compound 34)

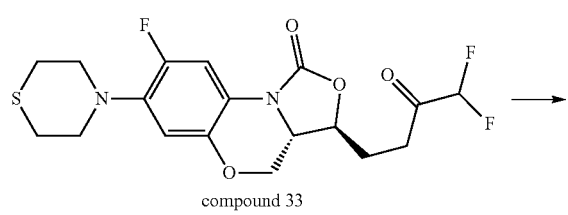

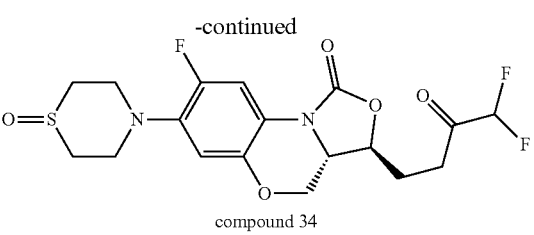

Compound 33 (0.11 g, 0.26 mmol) and sodium periodate (0.068 g, 0.32 mmol) were placed in a 25 mL flask, methanol (1 mL) and water (0.7 mL) were added. The resulting mixture was stirred overnight at room temperature and then concentrated. The residue was dissolved in methanol and insoluble solid was filtered off. The filtrate was purified by silica gel column chromatography (ethyl acetate/methanol=97/3) to give compound 34 (55 mg, 48.7%) as a white solid. Mp: 190-192° C.

$^1$H NMR (500 MHz, DMSO-d$_6$) δ: 9.18 (t, J=5.4 Hz, 1H), 7.60 (d, J=13.2 Hz, 1H), 6.78 (d, J=8.2 Hz, 1H), 6.28 (t, J=53.6 Hz, 1H), 4.61-4.46 (m, 2H), 4.04-3.92 (m, 2H), 3.65 (t, J=5.2 Hz, 2H), 3.49 (t, J=12.0 Hz, 2H), 3.24-3.12 (m, 2H), 3.01 (t, J=12.2 Hz, 2H), 2.89-2.77 (m, 2H). HR-MS (ESI): m/z [M+H]$^+$ calcd for C$_{17}$H$_{19}$F$_3$N$_3$O$_5$S: 434.0992; found: 434.0991.

Example 35

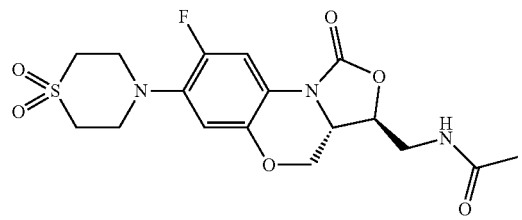 [SMILES: CC(=O)NC[C@@H]1OC(=O)N2c3cc(F)c(N4CCS(=O)(=O)CC4)cc3OC[C@@H]12]

N-(((3S,3aS)-7-(1,1-dioxidothiomorpholino)-8-fluoro-1-oxo-3a,4-dihydro-1H,3H-benzo [b]oxazolo[3,4-d][1,4]oxazin-3-yl)methyl)acetamide (compound 35)

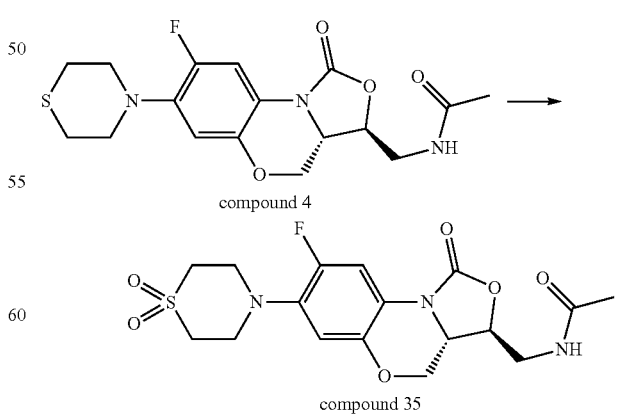

Compound 4 (0.5 g, 1.3 mmol) and sodium periodate (0.41 g, 1.95 mmol) were added to a 25 mL flask. Methanol (20 mL) and water (2 mL) were added. The mixture was stirred overnight at room temperature and then concentrated in a water bath at 50° C. The residue was dissolved in methanol and insoluble solid was filtered off. The filtrate was purified by silica gel column chromatography (ethyl acetate/methanol=96/3) to obtain compound 35 (102 mg, 29.0%) as a white solid. Mp. 226-228° C.

$^1$H NMR (400 MHz, CDCl$_3$) δ: 7.77 (d, J=12.6 Hz, 1H), 6.60 (d, J=7.8 Hz, 1H), 6.04 (t, J=6.0 Hz, 1H), 4.52 (dd, J=10.4, 3.0 Hz, 1H), 4.44-4.37 (m, 1H), 3.96-3.89 (m, 1H), 3.83 (t, J=10.2 Hz, 1H), 3.79-3.63 (m, 2H), 3.59-3.52 (m, 4H), 3.23-3.16 (m, 4H), 2.05 (s, 3H). HR-MS (ESI): m/z [M+H]$^+$ calcd for C$_{17}$H$_{21}$FN$_3$O$_6$S: 414.1130; found: 414.1126.

Example 36

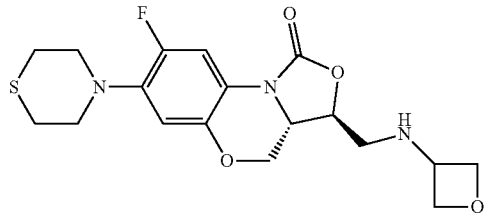 [SMILES: O=C1O[C@@H](CNC2COC2)[C@@H]2COc3cc(N4CCSCC4)c(F)cc3N12]

(3S,3aS)-8-Fluoro-3-((oxetan-3-ylamino)methyl)-7-thiomorpholino-3a,4-dihydro-1H,3H-benzo[b]oxazolo[3,4-d][1,4]oxazin-1-one (compound 36)

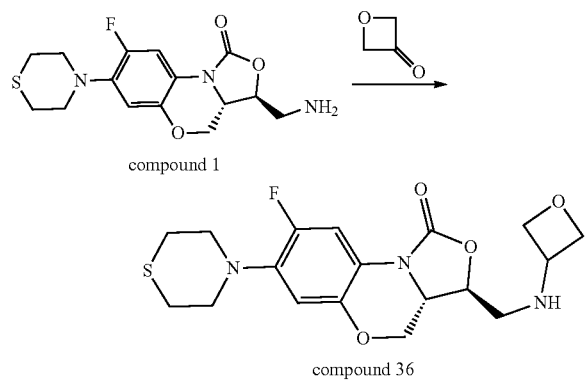

Compound 1 (0.1 g, 0.29 mmol), 3-oxetanone (0.031 g, 0.44 mmol) and sodium triacetoxyborohydride (184 mg, 0.87 mmol) were added to a 25 mL flask. Dichloromethane (4 mL) and a drop of acetic acid were added to the mixture and stirred overnight at room temperature. Saturated sodium bicarbonate (2 mL) was added and the mixture was stirred vigorously for 5 minutes, and diluted with dichloromethane. The organic phase was separated, washed with brine, dried over anhydrous sodium sulfate, filtered, and concentrated to give brown oil. The residue was purified by silica gel column chromatography (dichloromethane/methanol/ammonium hydroxide=100/2/1) to afford compound 36 (31 mg, 25.8%) as an off-white solid. Mp: 162-164° C.

$^1$H NMR (400 MHz, CDCl$_3$) δ: 7.75 (d, J=12.8 Hz, 1H), 6.55 (d, J=7.8 Hz, 1H), 4.84 (dd, J=7.4, 6.4 Hz, 2H), 4.54-4.35 (m, 3H), 4.35-4.28 (m, 1H), 4.10-3.97 (m, 2H), 3.85 (t, J=10.4 Hz, 1H), 3.32-3.21 (m, 4H), 3.04 (dd, J=13.0, 4.4 Hz, 1H), 2.94 (dd, J=13.0, 5.4 Hz, 1H), 2.83-2.76 (m, 4H), 2.05 (s, 1H). HR-MS (ESI): m/z [M+H]$^+$ calcd for C$_{18}$H$_{23}$FN$_3$O$_4$S: 396.1388; found: 396.1390.

Biological Activity Test

Example 1. Anti-Tuberculosis Activity Test In Vitro

Method: The method of Microplate Alamar Blue Assay (MABA) was used to determine the anti-tuberculosis activity in vitro.

Principle of experiment: Alamar Blue can be used as a redox indicator when added to the culture medium. The color changes from blue to red, reflecting the consumption of oxygen molecules by the microorganisms studied. The color changes of Alamar Blue can be measured by a photometer with an emission wavelength of 590 nm.

Experimental procedure: On a sterile 96-well plate (Falcon 3072; Becton Dickinson, Lincoln Park, N.J.), the experimental compound was dissolved in DMSO to prepare the initial solution with a concentration of 5 mg/mL. The hole with the highest concentration was added with 199 μL of 7H9 medium and 1 μL of the initial solution of the compound. After mixing, the mixture was added to the remaining hole in turn using the method of two-fold dilution. The final concentration of the compound was 25, 12.5, 6.25, 3.125, 1.56, 0.78, 0.39, 0.2, 0.1, 0.05, 0.025 g/mL. The suspension of Mycobacterium tuberculosis H$_{37}$Rv cultured for 2-3 weeks was inoculated into 7H9 medium containing 0.05% Tween 80 and 10% ADC. The suspension was cultured at 37° C. for 1-2 weeks. When the turbidity was McFarland 1 (equivalent to 10$^7$ CFU/mL), 100 μL of the suspension was added to every hole, to make the final concentration of the suspension 10$^6$ CFU/mL after dilution at 1:20. Two growth control holes without antimicrobial agents were set on each plate, and the 96-well plate was incubated at 37° C. After 7 days, the growth control holes were incubated with a mixture of 20 μL of 10×Alamar Blue and 50 μL of 5% Tween80 for 24 hours. During 24-hour incubation at 37° C., if the color changed from blue to pink, the above amount of mixture of Alamar Blue and Tween80 was added into each hole of experimental drug group. The color of each hole was recorded in 24-hour incubation at 37° C. The fluorescence value was determined by microplate reader at 590 nm and then MIC$_{90}$ was calculated.

TABLE 1

In vitro antituberculosis activity of the compounds in the present invention

| compound | MIC (μg/mL) |
|---|---|
| Compound 1 | 0.029 |
| Compound 4 | 0.044 |
| Compound 5 | 0.095 |
| Compound 6 | 0.034 |
| Compound 7 | 0.030 |
| Compound 8 | 0.031 |
| Compound 9 | 0.025 |
| Compound 10 | 0.160 |
| Compound 11 | 0.115 |
| Compound 12 | 0.227 |
| Compound 13 | 0.609 |
| Compound 14 | 0.918 |
| Compound 16 | 0.976 |
| Compound 17 | 0.974 |
| Compound 23 | 0.442 |

TABLE 1-continued

In vitro antituberculosis activity of
the compounds in the present invention

| compound | MIC (μg/mL) |
|---|---|
| Compound 28 | 0.232 |
| Compound 29 | 0.219 |
| Compound 30 | 0.208 |
| Compound 31 | 0.123 |
| Compound 32 | 0.908 |
| Compound 33 | 0.100 |
| Compound 34 | 0.492 |
| Compound 35 | 0.480 |
| Compound 36 | 0.237 |
| Linezoid | 0.294 |
| Sutezolid | 0.078 |
| Compound VII | 1.546 |

According to the data in Table 1, it can be seen that the compounds of the present invention have excellent in vitro anti-*Mycobacterium tuberculosis* activity.

Example 2. Cytotoxicity Test

Method: The Method of MTT

Principle of experiment: Active cells reduce 3-(4,5-dimethylthiazole-2-yl)-2,5-diphenyl tetrazolium bromide (trade name: thiazole blue)/MTT [3-(4,5-dimethylthiazo-2-yl)-2,5-diphenyl tetrazolium bromide] to insoluble blue formazan by mitochondrial dehydrogenase (e.g. succinate dehydrogenase). After the mixture was dissolved in DMSO, the activity of cells can be measured due to the amount of transformation was positively correlated with the number of living cells.

Experimental procedure: 1. Preparation of cell suspension. Vero cells cultured to logarithmic growth stage were digested with 0.25% trypsin for 2-3 minutes, then the lysis solution was removed and the appropriate amount of culture medium was added. After mixing, 20 μL of the mixture was counted under the microscope with a hematology counter, and the appropriate concentration of cell suspension was prepared for later use. Meanwhile, MTT solution (5 g/L) was prepared with PBS (phosphate buffered solution) and then filtered to remove bacteria, for later use. 2. Preparation of drug and cytotoxicity test. The tested compound was dissolved in DMSO and diluted for 50 times with the culture medium to obtain the highest concentration of the compound. Then the solution was diluted using culture medium at 1:3 on 96-well plate. Each compound had six concentrations, the highest concentration was 64 μg/mL, and each concentration had six parallel holes and 50 μL/hole. The prepared cell suspension was inoculated into 96-well plate at 50 μL/hole with a cell concentration of $4\times10^5$ cells/mL. At the same time, cell control hole without drug and blank control hole in culture medium without drug were set up. After 48 hours of incubation, MTT was added at 10 μL/hole and the culture was continued for 4 hours. The culture plate was taken out, the culture medium was carefully discarded, 100 μL of DMSO was added to each hole, and plate was oscillated until the formazan granules were completely dissolved. The optical density ($OD_{570}$) was measured by ELISA at 570 nm. 3. Data processing. The percentage of cell inhibition (%)=[(the control group $OD_{570}$ value–the drug group $OD_{570}$ value)/(The control group $OD_{570}$ value–the blank $OD_{570}$ value)]×100%. The dose-response curve was fitted with Origin 7.0 software and the concentration of various compounds at 50% cell inhibition rate ($IC_{50}$) was calculated.

TABLE 2

Cytotoxicity of compounds in the present invention

| compound | $IC_{50}$ (μg/mL) | compound | $IC_{50}$ (μg/mL) |
|---|---|---|---|
| compound 1 | 36.05 | compound 18 | >64 |
| compound 2 | 46.54 | compound 19 | >64 |
| compound 3 | >64 | compound 20 | >64 |
| compound 4 | >64 | compound 22 | >64 |
| compound 5 | >64 | compound 23 | >64 |
| compound 6 | >64 | compound 24 | >64 |
| compound 7 | >64 | compound 25 | >64 |
| compound 8 | >64 | compound 26 | >64 |
| compound 9 | >64 | compound 27 | >64 |
| compound 10 | >64 | compound 28 | >64 |
| compound 11 | 40.69 | compound 29 | >64 |
| compound 12 | >64 | compound 30 | >64 |
| compound 14 | 58.5 | compound 31 | >64 |
| compound 15 | >64 | compound 32 | >64 |
| compound 16 | >64 | compound 35 | >64 |
| compound 17 | 34.67 | compound 36 | >64 |
| compound 33 | 61.58 | Linezolid | >64 |
| compound 34 | >64 | | |

From Table 2, it can be seen that the cytotoxicity of the compounds in the present invention is weak, which shows that the compounds are very safe.

Example 3. Activity of Inhibiting Mitochondrial Protein Synthesis

The experimental steps were carried out according to the literature (Antimicrobial Agents and Chemotherapy, 2006, 50 (6), 2042-2049).

TABLE 3

Activity of inhibiting mitochondrial protein synthesis
by the compounds in the present invention

| compound | $IC_{50}$ (μg/mL) |
|---|---|
| compound 1 | 75.51 |
| compound 4 | 99.39 |
| compound 5 | >100 |
| compound 6 | >100 |
| compound 7 | 53.69 |
| compound 8 | >100 |
| compound 9 | >100 |
| compound 10 | >100 |
| compound 11 | >100 |
| compound 12 | >100 |
| compound 23 | 60.57 |
| compound 28 | >100 |
| compound 29 | >100 |
| compound 31 | >100 |
| Linezolid | 8.71 |
| Sutezolid | 7.98 |
| compound VII | 35.82 |

According to the data showed in Table 3, the inhibitory effect of the compounds in the present invention on mitochondrial protein synthesis is very weak, which are significantly superior to that of linezolid and sutezolid, that is, the possibility of bone marrow toxicity caused by the compounds in the present invention is very low.

4. In Vitro Activity of Compounds Against Drug Resistant Tuberculosis

The specific experimental method refers to the screening method of $H_{37}Rv$ strain of example 1 in the present invention.

TABLE 4

In vitro activity of the compounds in the present invention against drug resistant tuberculosis

| compound | MIC (μg/mL) | |
| --- | --- | --- |
| | 12525 | Linezolid-resistant strain |
| compound 4 | <0.016 | 0.246 |
| compound 23 | 0.053 | — |
| compound 28 | 0.047 | 3.016 |
| compound VII | 0.119 | 21.59 |
| linezolid | 0.138 | 3.999 |
| isoniazid | >40 | 0.032 |
| rifampicin | 22.423 | 0.073 |

According to the data in Table 4, the compounds of the present invention have robust anti-tuberculosis activity against clinically isolated 12525 strains (rifampicin- and isoniazid-resistant strains) and are superior to compound VII. In addition, compound 4 and compound 28 showed even better anti-tuberculosis activity against linezolid-resistant strain than compound VII. Especially, compound 4 is very effective against linezolid-resistant strain.

Although examples of the present invention have been shown and described above, it is understood that the above examples are illustrative and cannot be construed as limitations to the present invention, and that those skilled in the art may change, alter, replace and modify the above examples within the scope of the present invention.

The invention claimed is:

1. A compound represented by formula (I), stereoisomers thereof or a pharmaceutically acceptable salt thereof;

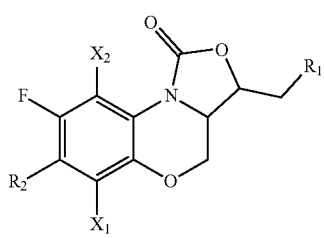
(I)

wherein,
$X_1$ and $X_2$ are each independently selected from H or F;
$R_1$ is —$OR_3$, —$NHR_3$, —$NHCOR_3$, —$NHCSR_3$, —$NHSO_2R_3$, —$NHCOOR_3$, —$NHCSOR_3$, —$NHCONHR_3$, —$NHCSNHR_3$, substituted or unsubstituted 5- to 6-membered heteroaryl;
$R_3$ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl, substituted or unsubstituted phenyl;
said substituted or unsubstituted 5- to 6-membered heteroaryl in $R_1$ or $R_3$ and substituted or unsubstituted 3- to 6-membered heterocyclic group in $R_3$ contain at least one heteroatom selected from N, O or S;
substituents on $R_1$ or $R_3$ are each independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino;

$R_2$ is substituted or unsubstituted

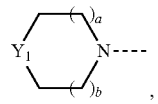

substituted or unsubstituted

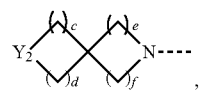

substituted or unsubstituted

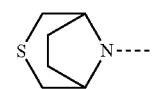

or substituted or unsubstituted

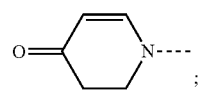
;

$Y_1$ is —S—, —S(=O)—, —S(O_2)—, —C(HF)—, —C(F_2)— or —C(=O)—;
$Y_2$ is —O—, —S—, —S(=O)—, —S(O_2)—, —C(HF)—, —C(F_2)— or —C(=O)—;
a and b are each 0, 1 or 2;
c and d are each 0, 1 or 2, and c and d are not 0 at the same time;
e and f are each 1 or 2;
substituents on $R_2$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

2. The compound, stereoisomers thereof or a pharmaceutically acceptable salt thereof according to claim 1, wherein the compound is represented by formula (II),

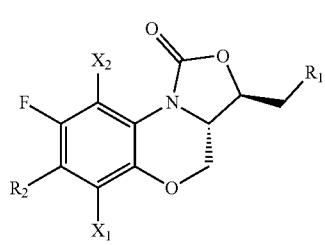
(II)

wherein,
$X_1$, $X_2$, $R_1$ and $R_2$ are the same as those defined in claim 1.

3. The compound, stereoisomers thereof or a pharmaceutically acceptable salt thereof according to claim 1, wherein the compound is represented by formula (III), (III)

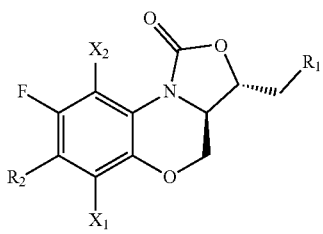

wherein,
X₁, X₂, R₁ and R₂ are the same as those defined in claim 1.

4. The compound, stereoisomers thereof or a pharmaceutically acceptable salt thereof according to claim 2, wherein,
X₁ and X₂ are each H;
R₁ is —NHR₃, —NHCOR₃, —NHSO₂R₃, —NHCOOR₃ or substituted or unsubstituted 5- to 6-membered heteroaryl;
R₃ is independently selected from the group consisting of hydrogen, substituted or unsubstituted C₁-C₄ alkyl, substituted or unsubstituted 3- to 6-membered cycloalkyl, substituted or unsubstituted 3- to 6-membered heterocyclic group, substituted or unsubstituted 5- to 6-membered heteroaryl;
said substituted or unsubstituted 5- to 6-membered heteroaryl in R₁ or R₃ and substituted or unsubstituted 3- to 6-membered heterocyclic group in R₃ contain at least one heteroatom selected from N, O or S;
substituents on R₁ or R₃ are independently selected from the group consisting of F, Cl, Br, hydroxyl, amino, nitro, cyano, trifluoromethyl, trifluoromethoxy, C₁-C₃ alkyl, halogenated C₁-C₃ alkyl, C₁-C₃ alkoxy and C₁-C₃ alkyl amino;
R₂ is substituted or unsubstituted

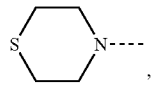

substituted or unsubstituted

substituted or unsubstituted

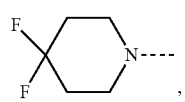

substituted or unsubstituted

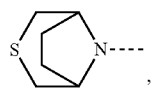

substituted or unsubstituted

substituted or unsubstituted

or substituted or unsubstituted

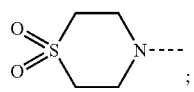

substituents on R₂ are independently selected from the group consisting of F, Cl, Br, hydroxyl, amino, nitro, cyano, trifluoromethyl, trifluoromethoxy, C₁-C₃ alkyl, halogenated C₁-C₃ alkyl, C₁-C₃ alkoxy and C₁-C₃ alkyl amino.

5. The compound, stereoisomers thereof or a pharmaceutically acceptable salt thereof according to claim 3, wherein,
X₁ and X₂ are each H;
R₁ is —NHR₃, —NHCOR₃, —NHSO₂R₃, —NHCOOR₃, substituted or unsubstituted 5- to 6-membered heteroaryl;
R₃ is independently selected from the group consisting of hydrogen, substituted or unsubstituted C₁-C₄ alkyl, substituted or unsubstituted 3- to 6-membered cycloalkyl, substituted or unsubstituted 3- to 6-membered heterocyclic group, substituted or unsubstituted 5- to 6-membered heteroaryl;
said substituted or unsubstituted 5- to 6-membered heteroaryl in R₁ or R₃ and substituted or unsubstituted 3- to 6-membered heterocyclic group in R₃ contain at least one heteroatom selected from N, O or S;
substituents on R₁ or R₃ are independently selected from the group consisting of F, Cl, Br, hydroxyl, amino, nitro, cyano, trifluoromethyl, trifluoromethoxy, C₁-C₃ alkyl, halogenated C₁-C₃ alkyl, C₁-C₃ alkoxy and C₁-C₃ alkyl amino;
R₂ is substituted or unsubstituted

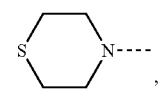

substituted or unsubstituted

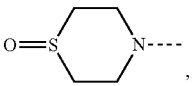

substituted or unsubstituted

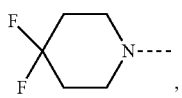

substituted or unsubstituted

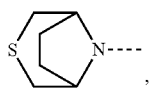

substituted or unsubstituted

substituted or unsubstituted

or substituted or unsubstituted

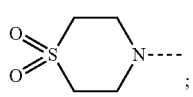

substituents on $R_2$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

6. The compound, stereoisomers thereof or a pharmaceutically acceptable salt thereof according to claim 2, wherein the compound is represented by formula (II-A),

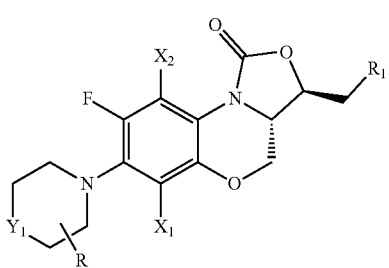

(II-A)

$X_1$ and $X_2$ are each H;
$Y_1$ is S, S=O, $CF_2$, $SO_2$;
$R_1$ is —$NHR_3$, —$NHCOR_3$, —$NHSO_2R_3$, —$NHCOOR_3$ or substituted or unsubstituted 5- to 6-membered heteroaryl;
$R_3$ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl;
said substituted or unsubstituted 5- to 6-membered heteroaryl in $R_1$ or $R_3$ and substituted or unsubstituted 3- to 6-membered heterocyclic group described in $R_3$ contain at least one heteroatom selected from N, O or S;
substituents on $R_1$ or $R_3$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino;
R represents one or more substituents, which are the same or different, and which are each independently selected from the group consisting of H, F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

7. The compound, stereoisomers thereof or a pharmaceutically acceptable salt thereof according to claim 2, wherein the compound is represented by formula (II-B),

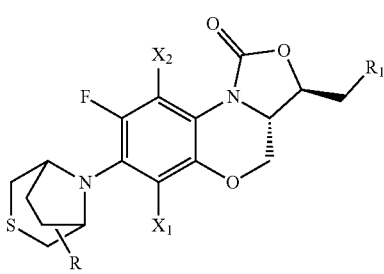

(II-B)

$X_1$ and $X_2$ are each H;
$R_1$ is —$NHR_3$, —$NHCOR_3$, —$NHSO_2R_3$, —$NHCOOR_3$ or substituted or unsubstituted 5- to 6-membered heteroaryl;
$R_3$ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl;
said substituted or unsubstituted 5- to 6-membered heteroaryl in $R_1$ or $R_3$ and substituted or unsubstituted 3- to 6-membered heterocyclic group in $R_3$ contain at least one heteroatom selected from N, O or S;
substituents on $R_1$ or $R_3$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino;
R represents one or more substituents, which are the same or different, and which are each independently selected from the group consisting of H, F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

8. The compound, stereoisomers thereof or a pharmaceutically acceptable salt thereof according to claim 2, wherein the compound is represented by formula (II-C),

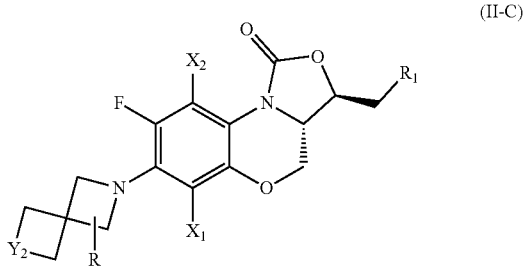

(II-C)

$X_1$ and $X_2$ are each H;
$Y_2$ is O or S;
$R_1$ is —$NHR_3$, —$NHCOR_3$, —$NHSO_2R_3$, —$NHCOOR_3$ or substituted or unsubstituted 5- to 6-membered heteroaryl;
$R_3$ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl;
said substituted or unsubstituted 5- to 6-membered heteroaryl in $R_1$ or $R_3$ and substituted or unsubstituted 3- to 6-membered heterocyclic group in $R_3$ contain at least one heteroatom selected from N, O or S;
substituents on $R_1$ or $R_3$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino;
R represents one or more substituents, which are the same or different, and which are each independently selected from the group consisting of H, F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

9. The compound, stereoisomers thereof or a pharmaceutically acceptable salt thereof according to claim 3, wherein the compound is represented by formula (III-A),

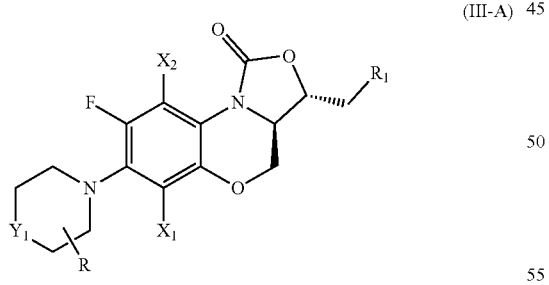

(III-A)

$X_1$ and $X_2$ are each H;
$Y_1$ is S, S=O, $CF_2$, $SO_2$;
$R_1$ is —$NHR_3$, —$NHCOR_3$, —$NHSO_2R_3$, —$NHCOOR_3$, substituted or unsubstituted 5- to 6-membered heteroaryl;
$R_3$ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl;
said substituted or unsubstituted 5- to 6-membered heteroaryl in $R_1$ or $R_3$ and substituted or unsubstituted 3- to 6-membered heterocyclic group in $R_3$ contain at least one heteroatom selected from N, O or S;
substituents on $R_1$ or $R_3$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino;
R represents one or more substituents, which are the same or different, and which are each independently selected from the group consisting of H, F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

10. The compound, stereoisomers thereof or a pharmaceutically acceptable salt thereof according to claim 3, wherein the compound is represented by formula (III-B),

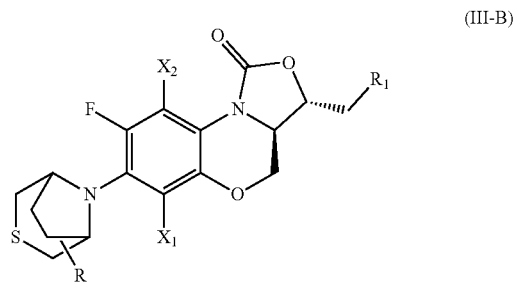

(III-B)

$X_1$ and $X_2$ are each H;
$R_1$ is —$NHR_3$, —$NHCOR_3$, —$NHSO_2R_3$, —$NHCOOR_3$ or substituted or unsubstituted 5- to 6-membered heteroaryl;
$R_3$ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl;
said substituted or unsubstituted 5- to 6-membered heteroaryl in $R_1$ or $R_3$ and substituted or unsubstituted 3- to 6-membered heterocyclic group in $R_3$ contain at least one heteroatom selected from N, O or S;
substituents on $R_1$ or $R_3$ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino;
R represents one or more substituents, which are the same or different, and which are each independently selected from the group consisting of H, F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

11. The compound, stereoisomers thereof or a pharmaceutically acceptable salt thereof according to claim 3, wherein the compound is represented by formula (III-C), (III-C)

X₁ and X₂ are each H;
Y₂ is O or S;
R₁ is —NHR₃, —NHCOR₃, —NHSO₂R₃, —NHCOOR₃, substituted or unsubstituted 5- to 6-membered heteroaryl;
R₃ is independently selected from the group consisting of hydrogen, substituted or unsubstituted $C_1$-$C_4$ alkyl, substituted or unsubstituted 3- to 6-membered cycloalkyl, substituted or unsubstituted 3- to 6-membered heterocyclic group, substituted or unsubstituted 5- to 6-membered heteroaryl;
said substituted or unsubstituted 5- to 6-membered heteroaryl in R₁ or R₃ and substituted or unsubstituted 3- to 6-membered heterocyclic group in R₃ contain at least one heteroatom selected from N, O or S;
substituents on R₁ or R₃ are independently selected from the group consisting of F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino;
R represents one or more substituents, which are the same or different, and which are each independently selected from the group consisting of H, F, Cl, Br, hydroxyl, amino, nitro, cyano, trifluoromethyl, trifluoromethoxy, $C_1$-$C_3$ alkyl, halogenated $C_1$-$C_3$ alkyl, $C_1$-$C_3$ alkoxy and $C_1$-$C_3$ alkyl amino.

12. The compound, stereoisomers thereof or a pharmaceutically acceptable salt thereof according to claim 1, wherein,
X₁ is H;
X₂ is H;
R₁ is —NH₂, —NHCH₃, R₂ is

13. The compound, stereoisomers thereof or a pharmaceutically acceptable salt thereof according to claim 1, wherein the compound of general formula (I) is selected from the following compounds:

Compound 1

Compound 2

Compound 3

-continued
Compound 4
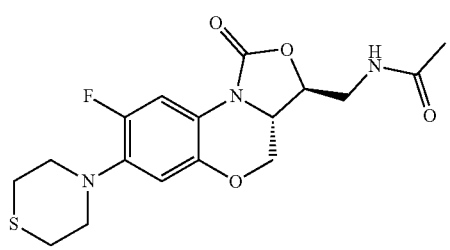
Compound 5
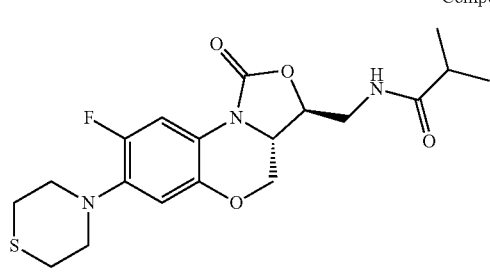
Compound 6
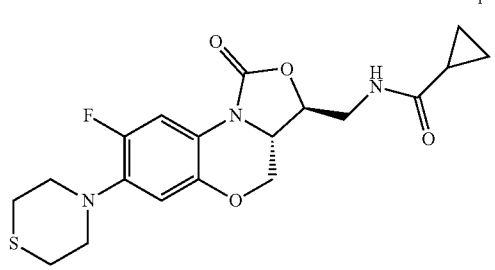
Compound 7
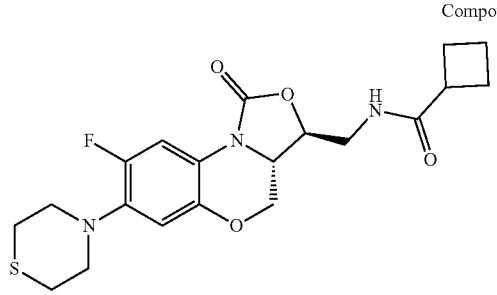
Compound 8
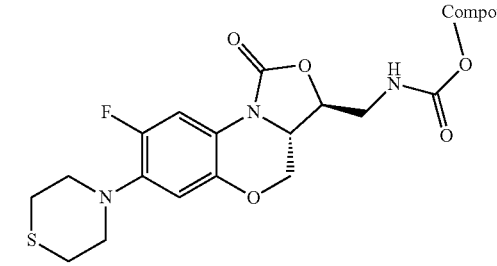
Compound 9
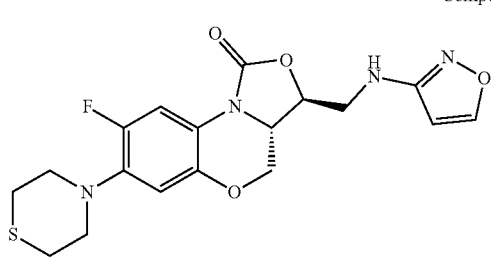
-continued
Compound 10
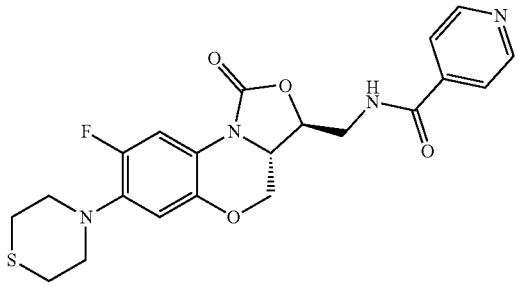
Compound 11
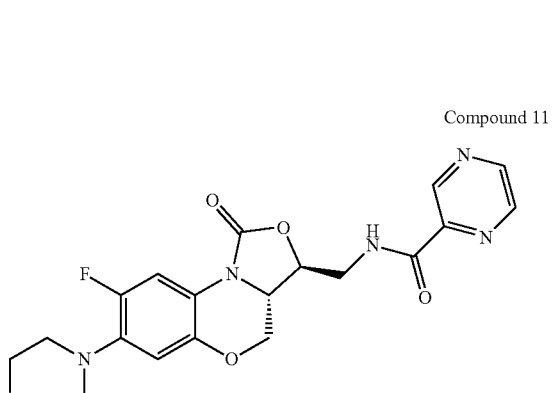
Compound 12
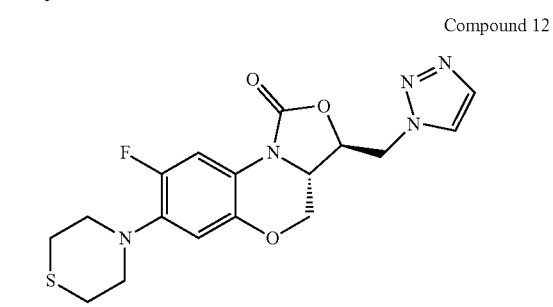
Compound 13
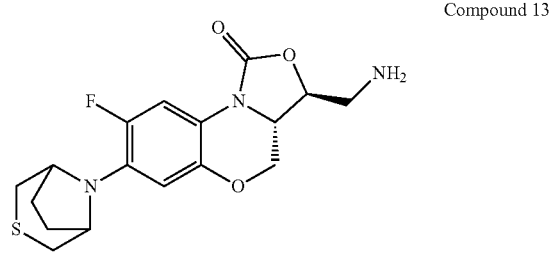
Compound 14
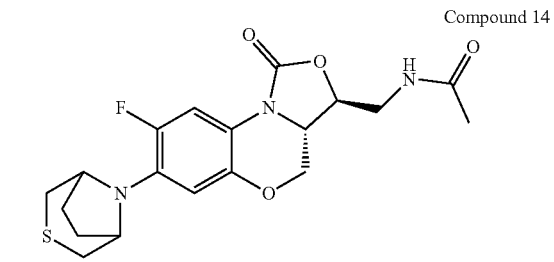

Compound 15
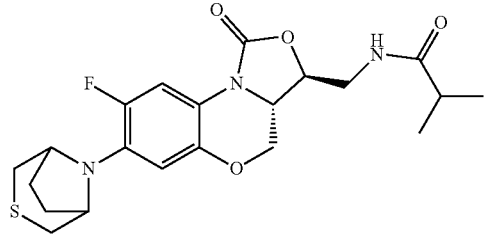
Compound 16
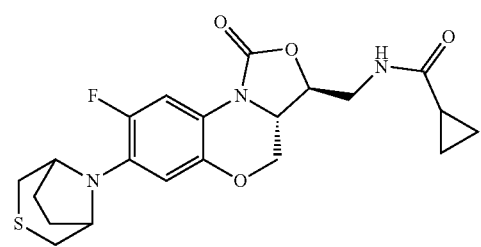
Compound 17
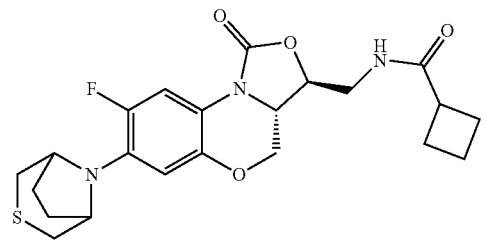
Compound 18
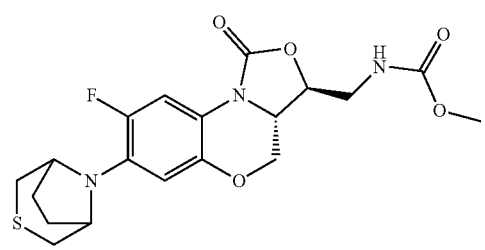
Compound 19
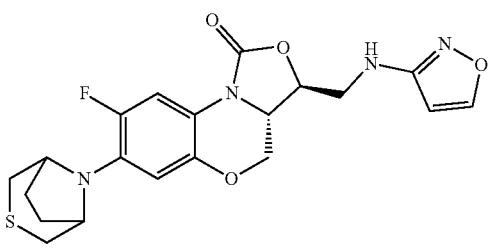
Compound 20
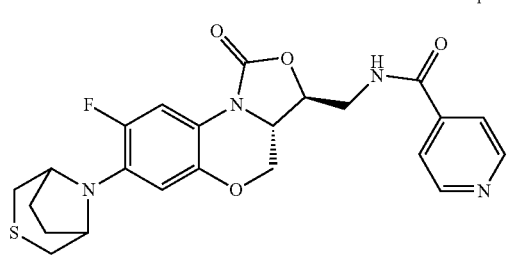
Compound 21
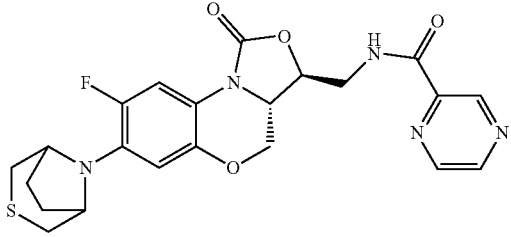
Compound 22
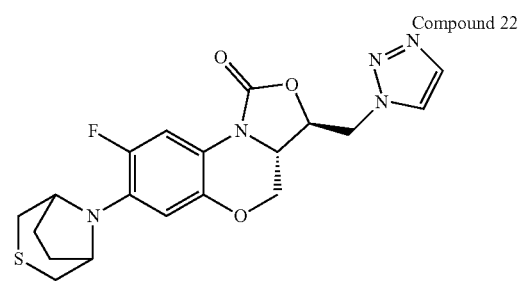
Compound 23
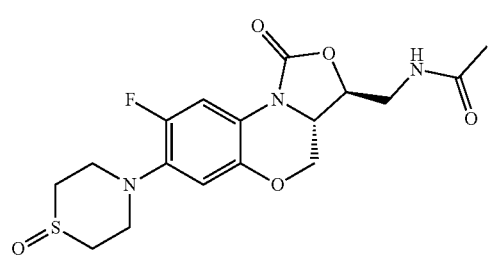
Compound 24
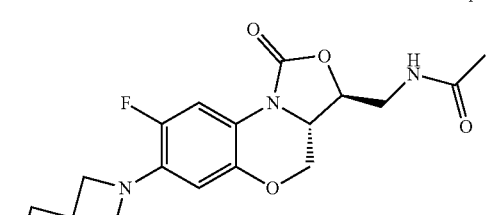
Compound 25
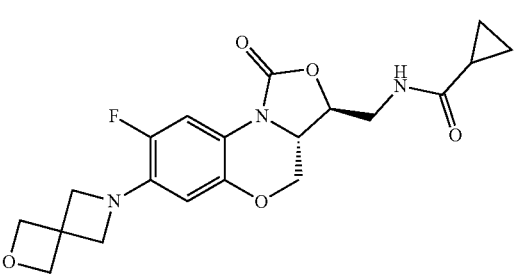

Compound 26
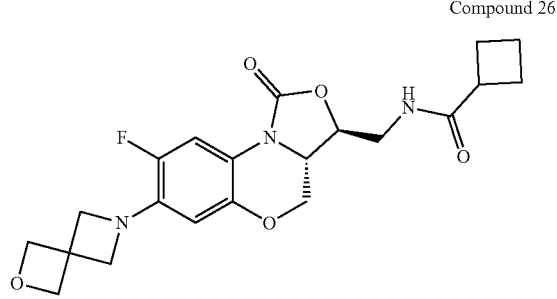
Compound 27
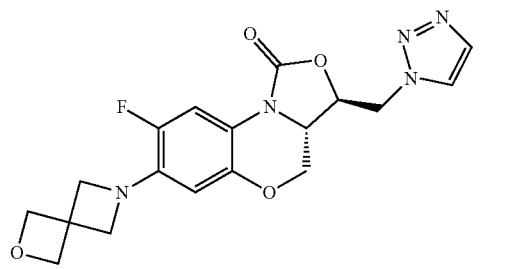
Compound 28
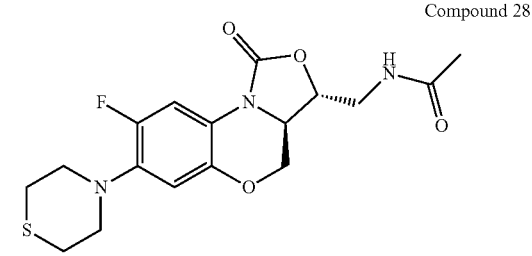
Compound 29
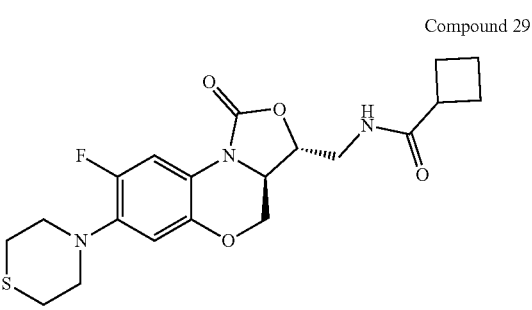
Compound 30
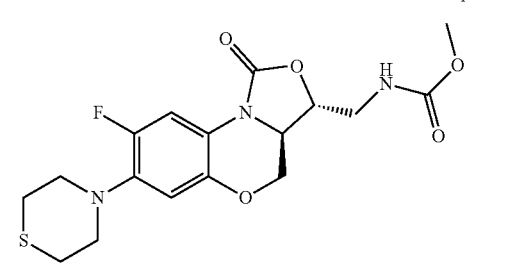
Compound 31
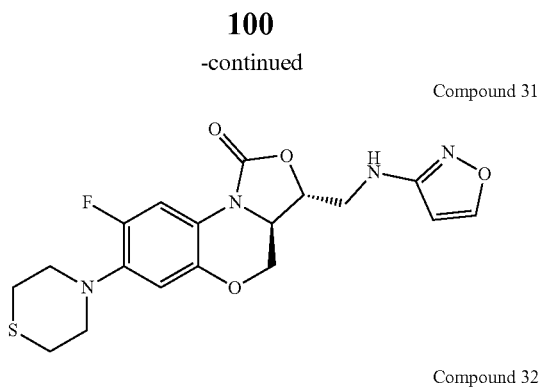
Compound 32
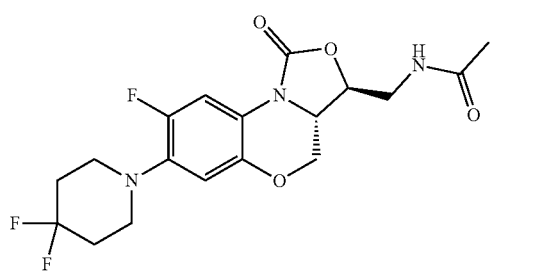
Compound 33
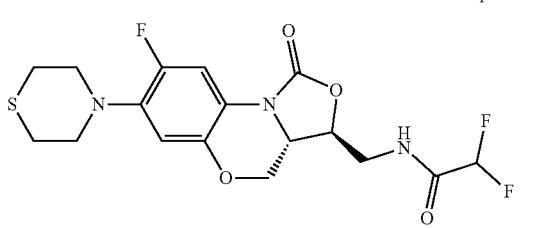
Compound 34
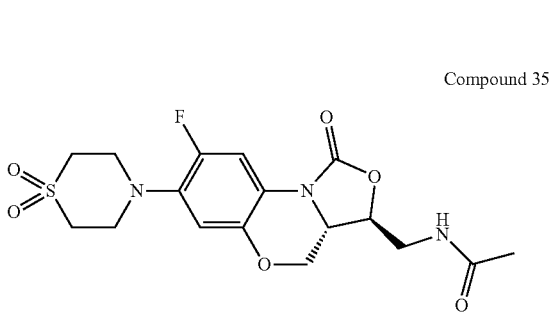
Compound 35
Compound 36

14. A method for preparation of the compounds according to claim 1, which comprises the following steps:

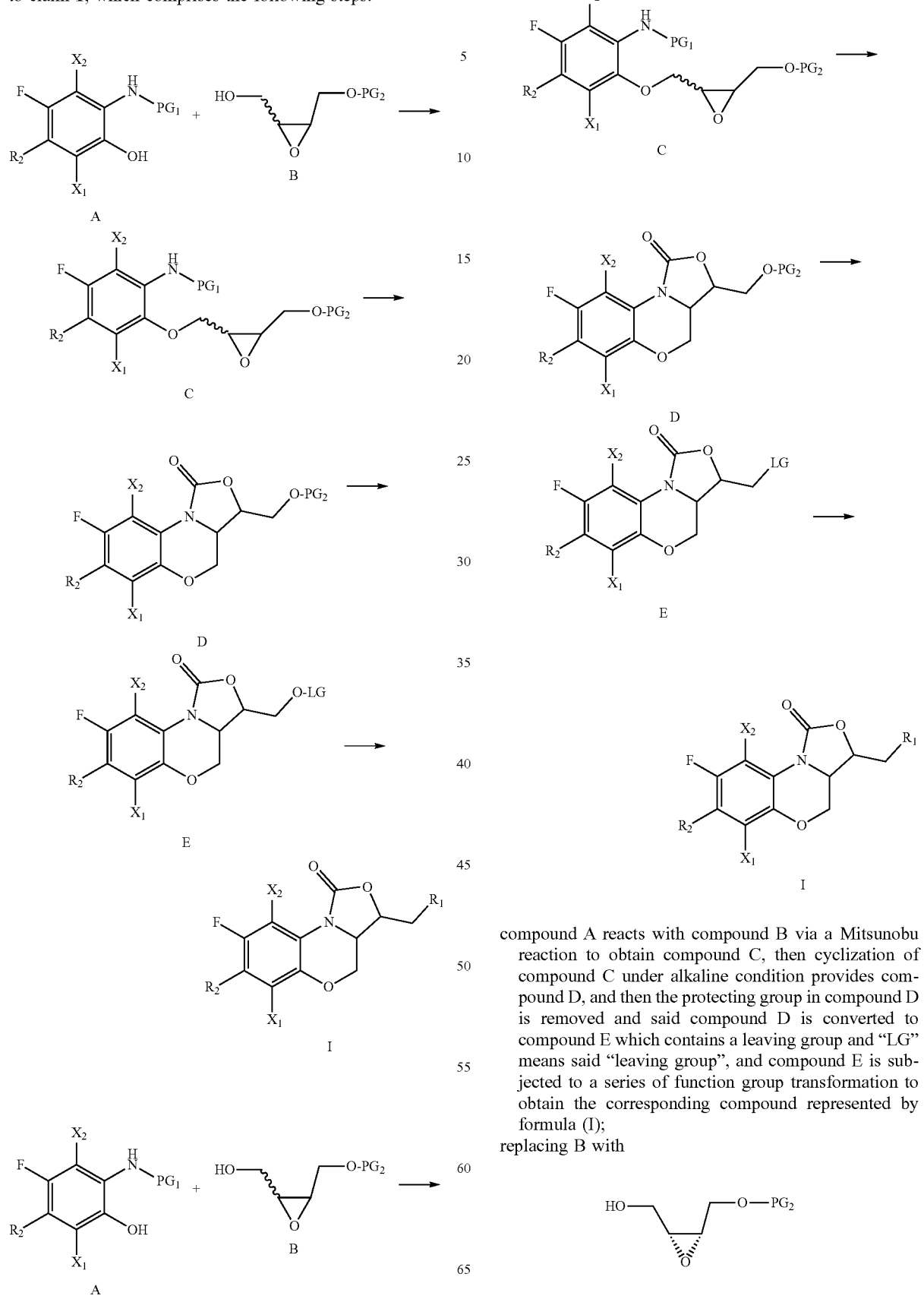

compound A reacts with compound B via a Mitsunobu reaction to obtain compound C, then cyclization of compound C under alkaline condition provides compound D, and then the protecting group in compound D is removed and said compound D is converted to compound E which contains a leaving group and "LG" means said "leaving group", and compound E is subjected to a series of function group transformation to obtain the corresponding compound represented by formula (I);

replacing B with

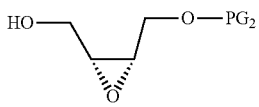

in the above synthetic steps gives the corresponding compound represented by formula (II);

replacing B with

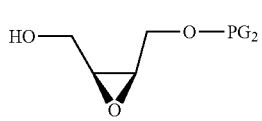

in the above synthetic steps gives the corresponding compound represented by formula (III);

wherein, $PG_1$ is a protective group of amino; $PG_2$ is a protective group of hydroxyl; $X_1$, $X_2$, $R_1$ and $R_2$ are the same as those defined in claim 1.

15. A pharmaceutical composition comprising a therapeutically and/or prophylactically effective amount of the compound, stereoisomers thereof or a pharmaceutically acceptable salt thereof according to claim 1, and one or more pharmaceutically acceptable adjuvant.

16. A method for treating and/or preventing microbial infectious diseases caused by *Mycobacterium tuberculosis*, comprising administrating the compound, stereoisomers thereof or a pharmaceutically acceptable salt thereof according to claim 1 to the subject in need thereof.

17. A method for treating and/or preventing microbial infectious diseases caused by *Mycobacterium tuberculosis*, comprising administrating the pharmaceutical composition according to claim 15 to the subject in need thereof.

* * * * *